United States Patent
Gros et al.

(10) Patent No.: US 6,551,781 B1
(45) Date of Patent: Apr. 22, 2003

(54) METHODS OF SCREENING FOR COMPOUNDS THAT REGULATE THE LEVEL OF NRAMP

(75) Inventors: Philippe Gros, St-Lambert (CA); Emil Skamene, Montréal (CA); Danielle Malo, Montréal (CA); Silvia Vidal, Ottawa (CA)

(73) Assignee: McGill University, Montreal (CA)

( * ) Notice: Subject to any disclaimer, the term of this patent is extended or adjusted under 35 U.S.C. 154(b) by 0 days.

(21) Appl. No.: 09/614,957

(22) Filed: Jul. 12, 2000

Related U.S. Application Data

(63) Continuation of application No. 08/637,823, filed as application No. PCT/CA94/00621 on Nov. 8, 1994, now Pat. No. 6,184,031, which is a continuation-in-part of application No. 08/235,405, filed on Apr. 28, 1994, now abandoned, which is a continuation-in-part of application No. 08/148,481, filed on Nov. 8, 1993, now abandoned.

(51) Int. Cl.[7] .......................... C12Q 1/68; C07H 21/02; C07H 21/04
(52) U.S. Cl. ................ 435/6; 435/4; 435/7.1; 435/69.1; 435/71.1; 435/455; 435/471; 536/23.5; 536/24.31
(58) Field of Search .................. 435/4, 6, 7.1, 69.1, 435/71.1, 455, 471; 536/23.5, 24.33, 24.31

(56) References Cited

PUBLICATIONS

Kriegler, Gene Transfer and Expression: A Lab. Manual, 1990, p 23–61.
Bairoch, 1991, Nucl. Acids Res. 19:2241–2245.
Binford et al., 1982, J. Am. Med. Assoc. 247:2283–2292.
Blackwell et al., 1991, Immunol. Lett. 30:241–248.
Buckler et al., 1991, Proc. Natl. Acad. Sci. USA 88:4005–4009.
Burke et al. 1991, Mammalian Genome 1:65.
Buschman et al., 1989, Res. Immunol. 140:793–797.
Crocker et al., 1984, Infect. Immun. 43:1033–1040.
Denis et al., 1988, J. Immunol. 140:2395–2400.
Denis et al., 1988, J. Immunol. 141:3988–3993.
Denis et al., 1990, J. Leukoc. Biol. 47:25–30.
Epstein et al., 1991, Cell 67:767–774.
Goto et al., 1989, Immunogenetics 30:218–221.
Gros et al., 1983, J. Immunol. 131:1966–1972.
Gros et al., 1986, Nature 323:728–731.
Gros and Buschman, 1992, Int. Rev. Cytology 137C:169–197.
Kerppola and Ames, 1992, J. Biol. Chem. 267:2329–2336.
Kyte and Doolittle, 1982, J. Mol. Biol. 157:105–132.
Lissner et al., 1983, J. Immumol. 131:3006–3013.
Malo et al., 1993, Genomics 16:655–663.
Malo et al., 1993, Genomics 17:667–675.
Marchuk et al., 1991, Nucl. Acids Res. 19:1154.
Meltzer et al., 1975, JNCI, 54:1177–1184.
Rommens et al., 1993, Hum. Mol. Genet. 2:901–907.
Rossi et al., 1992, Proc. Natl. Acad. Sci. USA 89:2456–2460.
Schurr et al., 1991, Am. J. Trop. Med. Hyg. 44:4–11.
Skamene, 1985, Prog. Leukoc. Biol. 3:111–559.
Skamene and Pietrangeli, 1991, Curr. Opin. Immunol. 3:511–517.
Stach et al., 1984, J. Immunol. 132:888–892.
Vidal et al., 1993, Cell 73:469–485.
Wilkes et al., 1991, Genomics 9:90–95.
Woodget et al., 1986, Eur. J. Biochem. 161:177–184.
Worthen et al., 1987, Am. Rev. Resp. Dis. 136:19–28.
Bonthron et al., 1986, Nature 324: 270–273.
Gruenheid et al., 1995, Genomics 25:514–525.
Vidal et al., 1992, Genomics 14:32–37.
Rommens et al., 1989, Science 245:1059–1065.
Casteels et al., 1989, EMBO J. 8:2387–2391.

*Primary Examiner*—Carla J. Myers
(74) *Attorney, Agent, or Firm*—Klauber & Jackson

(57) ABSTRACT

The present invention relates to mouse and human cDNAs for a gene family designated Nramp (natural resistance-associated macrophage protein), involved in macrophage function and responsible for the natural resistance to infection with intracellular parasites, and to the isolation of Nramp sequences from other animal sources. The nucleotide sequences of the mouse and human cDNAs are disclosed, as are the amino sequences of the encoded products. The cDNAs can be expressed in expression constructs. These expression constructs and the proteins produced therefrom can be used for a variety of purposes including diagnostic and therapeutic methods.

21 Claims, 9 Drawing Sheets

```
CAGCAAACCAATGAGGAGGCGTTCAACATCTGTGCCAACAGCCTCCAACTGCAAACTATGCTAAGATCTTCCCAGGACACAATAACACTGTGTCAGTGGATATTTATCAAGGAGGTGTGATC    1320
 Q  Q  T  N  E  E  A  F  N  I  C  A  N  S  S  L  Q  N  Y  A  K  I  F  P  R  D  N  N  T  V  S  V  D  I  Y  Q  G  G  V  I        284

CTAGCGTGTCTCTTTGGCCTGTCTGGGCCCTCTACATCTGCTACCGGCAGCGGGCCAGTAGTCTCCTGGCAGTTCTACTATGACCGGCCACTATGCAGGACAGTTCTGTAGCAGGGTTCCTT    1440
 L  G  C  L  F  G  P  A  A  L  Y  I  W  A  V  G  L  L  A  A  G  Q  S  T  M  T  G  T  Y  A  G  Q  F  V  N  E  G  F  L           324

AAGCTCCGGTGCTGCCCCTTCCGGTCGTCCTTCCTCACCCGCCGCTCTTGGGCCATCGTCTGCCAGAGACCTGTCTCCGAGACCTGAAGGACCTGTCCGGCCTCAACGATCTACTC        1560
 K  L  R  W  S  R  F  A  R  V  L  L  T  R  S  C  A  I  L  P  T  V  L  V  A  V  F  R  D  L  K  D  L  S  G  L  N  D  L  L        364

AATGTTCTGCAGAGTCTACTGCTGCCCTTCGCTGTCCTGCCCATTTTGACTTTCACCAGCATGCCAGCTGTGATGCAGGAGTTTGCCAACGGCCGATGAGCAAAGCCATCACTCTGC        1680
 N  V  L  Q  S  L  L  L  P  F  A  V  L  P  I  L  T  F  T  S  M  P  A  V  M  Q  E  F  A  N  G  R  W  S  K  A  I  T  S  C        404

ATCATGGCGGCTAGTCTGCGCCATCAACCTGTACTTTGTGATCAGCTACTTGCCCTCGTTGCCTCTGTTGGCCTCTGTTGGCAATAGGTTACTTGGGCCTGACT        1800
 I  M  A  L  V  C  A  I  N  L  Y  F  V  I  S  Y  L  P  S  L  P  H  P  A  Y  F  G  L  V  A  L  F  A  I  G  Y  L  G  L  T        444

GCTTATCTGGCCTGGACCTGTTGCATCGCCCACGGAGCCACTTTCCTGACCCACAGCTCCCACAAGCACTTCCTCTACGGCCTCCCTAACGAGGAGGAGGCCTGCAGGGTTCCGGG        1920
 A  Y  L  A  W  T  C  C  I  A  H  G  A  T  F  L  T  H  S  S  H  K  H  F  L  Y  G  L  P  N  E  E  E  G  G  V  Q  G  S  G        484

TGACCGCGGCATCCAGCAAGCAAAGAGGCAACAGGGCCAACAATTGGAGGTCCCCTACGGCTTTCCTGGATTACCGGTTTCCAGTTTGGACAAGTCTTACCTCGGAAT 2040

AATGACACCATTCTTATCACCACCTAAGAGACTTAAAAACACAGTGCCTGGGGGCGAGACATGCCTCAGGTGCTGAAGAACACTAGCCACCCTTTCAGAAGATGCGATTCAATT 2160

CCCAGCTCATCAACGTGGTGCCTTCAACTGAACGTGACTCCCAGTTCCCAAGAACACCTCAAACAGAACCTCCATTGTCTCACTCCAGTCGTGGAAGATGAAGGAGGAGTCCT 2280

AAAGAGTTCTAGTCGGGTCTCTGGAGAGACGGCTCAGCTGCTCGTTAAGAGCACCGACTCTCTTCCAGAGGTCCTGAGTTCATTCCCAGCCAACCATGCCTCACAACCATCCATAA 2400

TGGATCCCCTCTTCTGTGTCTGAAGACAACAGTGTCCTCACATATAAAATAAATCTTAAAAAAAAAA 2480
```

| | (E,Q) | (S,T,A)/2 | 3x | | G | | 6x | | | (L,I,V,M,F,Y,A)/4 | 4x | (F,L,I,V)/(P,K) | |
|---|---|---|---|---|---|---|---|---|---|---|---|---|---|
| HisQ | E | A | T | A | F | F | T | H | G | Q | T | F | R | R | I | M | F | P |
| MalF | E | A | S | A | M | D | G | A | G | P | F | Q | N | F | K | I | T | L | P |
| PstA | E | A | Y | A | L | G | T | P | K | W | K | M | I | S | A | I | T | I | K |
| PstC | E | S | A | Y | G | I | G | C | T | T | W | E | V | I | W | R | I | T | L | P |
| ChlJ | Q | A | R | T | L | G | A | G | R | W | R | V | F | T | F | T | L | P |
| Nramp | Q | S | T | M | T | G | T | Y | A | G | Q | F | V | M | E | G | F | L | K |
| CrnA | Q | S | R | P | S | G | P | P | S | I | I | A | Y | A | I | P | D | V | Q |

| Strain | Ala32 | Gly/Asp105 | Phe234 | Lys325 | Bcg |
|---|---|---|---|---|---|
| LP/J | GCG | GGC | TTC | AAG | R |
| 129/J | GCG | GGC | TTC | AAG | R |
| C58/J | GCG | GGC | TTC | AAG | R |
| AKR/J | GCG | GGC | TTC | AAG | R |
| C57L/J | GCG | GGC | TTC | AAG | R |
| C57BR/cdJ | GCG | GGC | TTC | AAG | R |
| DBA2/J | GCG | GGC | TTC | AAG | R |
| RIIIs/J | GCG | GGC | TTC | AAG | R |
| P/J | GCG | GGC | TTC | AAG | R |
| BUB/BnJ | GCG | GGC | TTC | AAG | R |
| RF/J | GCG | GGC | TTC | AAG | R |
| PL/J | GCG | GGC | TTC | AAG | R |
| SJL/J | GCG | GGC | TTC | AAG | R |
| A/J | GCC | GGC | TTT | AAG | R |
| C3H/HeJ | GCC | GGC | TTT | AAG | R |
| NZB/B1NJ | GCC | GGC | TTT | AAG | R |
| CBA/J | GCC | GGC | TTT | AAG | R |
| NOD/Lt | GCC | GGC | TTC | AAA | R |
| Mus spretus | GCC | GGC | TTC | AAG | R |
| SWR/J | GCG | GGA | TTC | AAG | R |
| BALB/cJ | GCG | GAC | TTC | AAG | S |
| C57BL/6J | GCG | GAC | TTC | AAG | S |
| C57BL/10J | GCG | GAC | TTC | AAG | S |
| CE/J | GCG | GAC | TTC | AAG | S |
| SWV | GCG | GAC | TTC | AAG | S |
| DBA1/J | GCG | GAC | TTC | AAG | S |
| NZW/LacJ | GCG | GAC | TTC | AAG | S |

FIG. 6

TM2-Nramp

```
MOUSE   100 I P L W G G V L I T I V D T F F F L F L 119
CHICKEN  _ _ _ _ _ _ _ _ _ _ _ _ T _ _ L _ _ _ _ _
RAT      _ _ _ _ _ _ _ _ _ _ _ _ _ _ _ _ _ _ _ _
HUMAN    _ _ _ _ _ _ _ _ _ _ _ _ _ _ _ _ _ _ _ _
```

FIG. 8

```
NRAMP2                                                                    
Nramp2     mvldpkekmp ddgasgdhgd saslgainpa ysnsslphst gdseepftty
NRAMP1     .......... ..mtgdkgpq rlsgssygsi ssptsptspg pqqapprety
Nramp1     .......... ..misdkspp rlsrpsygsi s...slpgpa pqpapcrety
Consensus  ---------- ---------- ---------- ---------- ----------

Pkc         TM1
NRAMP2     1 .......gme eyscFSFRKL WAFTGPGFLM SIAYLDPGNI ESDLQsGAVA  43
Nramp2       fdekipipee eyscFSFRKL WAFTGPGFLM SIAYLDPGNI ESDLQsGAVA
NRAMP1       lsekipipdt kpgtFSLRKL WAFTGPGFLM SIAFLDPGNI ESDLQaGAVA
Nramp1       lsekipipsa dqgtFSLRKL WAFTGPGFLM SIAFLDPGNI ESDLQaGAVA
Consensus  ---------- ----FS-RKL WAFTGPGFLM SIA-LDPGNI ESDLQ-GAVA TM2
NRAMP2     44 GFKLLWILLI ATivGLLQR LAARLGVVTG IhLaEVCHrq YPKVPRviLW  93
Nramp2        GFKLLWVLLI ATivGLLQR LAARLGVVTG IhLaEVCHrq YPKVPRiiLW
NRAMP1        GFKLLWVLLw ATvIGLLcQR LAARLGVVTG kdLgEVCHly YPKVPRtvLW
Nramp1        GFKLLWVLLw ATvIGLLcQR LAARLGVVTG kdLgEVCHly YPKVPRiiLW
Consensus     GFKLLWVLL- AT--GLL-QR LAARLGVVTG --L-EVCH-- YPKVPR-LW TM3                      TM4
NRAMP2     94 LmVELAIIGS DMQEVIGsAI aiNLLSvGRI PIWGGVLITI aDTFvFLFLD  143
Nramp2        LmVELAIIGS DMQEVIGsAI aiNLLSaGRv PvWGGVLITI aDTFvFLFLD
NRAMP1        LtIELAIVGS DMQEVIGtAI afNLLSaGRI PIWGGVLITI vDTFfFLFLD
Nramp1        LtIELAIVGS DMQEVIGtAI sfNLLSaGRI PIWGGVLITI vDTFfFLFLD
Consensus     L---ELAI-GS DMQEVIG-AI --NLLS-GR- P-WGGVLITI -DTF-FLFLD TM5
NRAMP2    144 kYGLRKLEAF FGFLITIMAL TFGYEYVtvk PsQsqvLkGM fvPsCsGCrt  193
Nramp2        kYGLRKLEAF FGFLITIMAL TFGYEYItvk PsQsqvLrGM fvPsCpGCrt
NRAMP1        nYGLRKLEAF FGLLITIMAL TFGYEYVvar PeQgalLrGL flPsCpGCgh
Nramp1        nYGLRKLEAF FGLLITIMAL TFGYEYVvah PsQgalLkGL vlptCpGCgq
Consensus     -YGLRKLEAF FG-LITIMAL TFGYEYV--- P-Q---L-G- -P-C-GC---

TM6
NRAMP2    194 PqieQAVGIV GAVIMPHNmY LHSALVKSRq VnRnnkqEVR EANkYFFIEs  243
Nramp2        PqveQAVGIV GAVIMPHNmY LHSALVKSRq VnRankqEVR EANkYFFIEs
NRAMP1        PellQAVGIV GAIIMPHNiY LHSALVKSRe IdRarraDIR EANmYFLIEa
Nramp1        PellQAVGIV GAIIMPHNiY LHSALVKSRe VdRtrrvDVR EANmYFLIEa
Consensus     P----QAVGIV GA-IMPHN-Y LHSALVKSR- V-R------VR EAN-YF-IE-
```

FIG. 7A

```
                      TM7                           Ψ
NRAMP2  244  cALfVSFII NvFVvsVFqe AFFgkTNeqv veVCtNtSsp h.AglFPkdN  292
Nramp2       cALfVSFII NvFVvsVFqe AFFekTNkqv veVCkNnSsp h.AdlFPsdN
NRAMP1       tIALsVSFII NIFVmaVFgq AFYqkTNqaa fnICqNsSh dyAkiFPmnN
Nramp1       tIALsVSFII NIFVmaVFgq AFYqqTNeea fnICqNsSq nyAkiFPrdN
Consensus    -IAL-VSFII N-FV--VF-- AF----TN--- --C-N-S- --A-FP--N Ψ                TM8
NRAMP2  293  sTlaVDIYkG GvVLGCyFGP AALYIWAVGi LAAGqSSTMT GTYsGQFVME  342
Nramp2       sTlaVDIYkG GvVLGCyFGP AALYIWAVGi LAAGqSSTMT GTYsGQFVME
NRAMP1       aTvaVDIYqG GvILGCIFGP AALYIWAIGI LAAGqSSTMT GTYaGQFVME
Nramp1       nTvsVDIYqG GvILGCIFGP AALYIWAVGI LAAGqSSTMT GTYaGQFVME
Consensus    -T--VDIY-G Gv-LGC-FGP AALYIWAVG- LAAGqSSTMT GTY-GQFVME TM9                                TM10
NRAMP2  343  GFLnLkWSRF ARvvLTRSIA IiPTILVAVF qDvehLtGMN DFLNVLQSLq  392
Nramp2       GFLnLkWSRF ARViLTRSIA IiPTILVAVF qDvehLtGMN DFLNVLQSLq
NRAMP1       GFLrLrWSRF ARVILTRScA IIPTvLVAVF rDIrdLsGLN DLLNVLQSLI
Nramp1       GFLkLrWSRF ARVILTRScA IIPTvLVAVF rDIkdLsGLN DLLNVLQSLI
Consensus    GFL-L-WSRF ARV-LTRS-A I-PT-LVAVF -D----L-G-N D-LNVLQSL- TM10                          TM11
NRAMP2  393  LPFAIiPILT FTyvrpvMsD FqNGIgwrib ggilvIiICs INMYFVVvYv  442
Nramp2       LPFAIiPILT FTsIrpvMsE FsNGigwrib ggilvIiVCs INMYFVVvYv
NRAMP1       LPFAvIPILT FTsmptIMqE FqNGIInkvv tssimvlVCa INLYFVVsYI
Nramp1       LPFAvIPILT FTsmpqvMqE FqNGrmskd tscimqlVCa INLYFVIsYI
Consensus    LPFA--PILT FT------M-E F-NG------ -------VC- IN-YFVV-Y-

TM12                         Ck2
NRAMP2  443  rdLgHvAlYv vaAvvsvqYL gFvfYLgWqC liAIGmsFLd cghtvsiskg  492
Nramp2       qeLgHvAlYv vaAvvsvqYL tFvfYLgWqC liAIGl sFLd cgrsyrlglt
NRAMP1       pslpHpAyFg laAllaqYL gLstYLvWtC clAhGqtFLq hsshhhf...
Nramp1       pslpHpAyFg lvAlfqigYL gLtqYLqWtC ciAhGqtFLt hsshkhf...
Consensus    --L-H-A--- --A-----YL ----YL-W-C --A-G--FL- -----------

NRAMP2  493  ......ILte eatrgyvk.. 504
Nramp2       qqpelyILnt vdqdsvvsr.
NRAMP1       ....IygLle edqkg.etsg
Nramp1       ....IygLpn eeqggvqgsg
Consensus    -------L-- -----------
```

FIG. 7B

METHODS OF SCREENING FOR COMPOUNDS THAT REGULATE THE LEVEL OF NRAMP

CROSS-REFERENCE TO RELATED APPLICATIONS

This application is continuation of U.S. Ser. No. 08/637,823 filed May 8, 1996, now U.S. Pat. No. 6,184,031, which is the National Stage application of PCT/CA94/00621 filed Nov. 8, 1994, which is a continuation in part of U.S. Ser. No. 08/235,405, filed Apr. 28, 1994, now abandoned, which is a continuation in part of U.S. Ser. No. 08/148,481, filed Nov. 8, 1993, now abandoned.

TECHNICAL FIELD

This invention relates to mouse and human Nramp cDNAs (natural resistance-associated macrophage protein), responsible for the natural resistance to infection with intracellular parasites, and to the isolation of Nramp sequences from other animal sources.

The cDNAs can be expressed in expression constructs. These expression constructs and the proteins produced therefrom can be used for a variety of purposes including diagnostic and therapeutic methods.

The ability of a host to resist infection with a wide range of viral, bacterial, and parasitic pathogens is strongly influenced by genetic factors (reviewed by Skamene, 1985, Prog. Leukoc. Biol. 3: 111–559; Skamene and Pietrangeli, 1991, Curr. Opin. Immunol. 3, 511–517). A clear manifestation of differential resistance or susceptibility of human populations in endemic areas of disease and during epidemics has been observed in the case of mycobacterial infections such as tuberculosis (*Mycobacterium tuberculosis*) and leprosy (*Mycobacterium leprae*). Epidemiological studies of tuberculosis provide evidence that resistance to tuberculosis in humans is genetically controlled. The problem of the extend to which genetic factors enter into susceptibility to tuberculosis is one of the oldest in human genetics (Neel et al., 1954, In Human Heredity, The University of Chicago Press, p. 292). Infection by *M. tuberculosis* results in a wide spectrum of clinical manifestations ranging from a change in skin test sensitivity to purified protein derivative to fully developed pulmonary disease which may cause death if the infection is left untreated. Although the specific genes involved have not been identified, recent studies suggest that the basis for this genetic distinction resides in a differential capacity of host macrophages to kill phagocytized tubercle bacilli. A similar situation exists for leprosy where increased prevalence among certain ethnic groups points to the role of genetic factors in susceptibility to leprosy (reviewed by Schurr et al., 1991, Am. J. Trop. Med. Hyg. 44: 4–11). Moreover, a two-stage model for genetic control of innate susceptibility to leprosy has been suggested: susceptibility to disease per se appears to be determined by the expression of a single recessive autosomal gene, while the progression of the disease and the type of leprosy ultimately developed (mild tuberculoid or severe lepromatous) are associated with genes of the major histocompatibility complex (Schurr et al., 1991, Am. J. Trop. Med. Hyg. 44: 4–11).

In the mouse, innate resistance or susceptibility to infection with several mycobacterial species such as *Mycobacterium lepraemurium, Mycobacterium bovis* (BCG), and *Mycobacterium intracellulare* is under remarkably similar genetic control (reviewed by Blackwell et al., 1991, Immunol. Lett. 30: 241–248; Skamene and Pietrangeli, 1991, Curr. Opin. Immunol. 3: 511–517). In inbred mouse strains, infection with BCG is biphasic, with an early non-immune phase (0–3 weeks) characterized by rapid proliferation of the bacteria in reticuloendothelium (RE) organs (liver and spleen) of susceptible strains and absence of bacterial growth in resistance strains. The late phase (3–6 weeks) is associated with specific immune response, leading either to complete clearance of the bacterial load or to persistent infection in the RE organs of the susceptible strains. While the late phase of infection is under the control of genes linked to the major histocompatibility complex, the difference in innate susceptibility detected in the early phase is controlled by the expression of a single dominant chromosome 1 gene designated Bcg, which is present in two allelic forms in inbred strains, $Bcg^r$ (resistant, dominant) and $Bcg^s$ (susceptible, recessive) (reviewed by Blackwell et al., 1991, Immunol. Lett. 30: 241–248; Skamene and Pietrangeli, 1991, Curr. Opin. Immunol. 3: 511–517). The Bcg locus is inseparable by genetic mapping from two other genes, known as Ity and Lsh, which together control natural resistance to infection with antigenitically and taxonomically unrelated intracellular parasites, including *Salmonella typhimurium* and *Leishmania donovani*.

The cellular compartment responsible for the phenotypic expression of the gene is bone marrow-derived and radio resistant and can be inactivated by chronic exposure to silica, a macrophage poison (Gros et al., 1983, J. Immunol. 131: 1966–1973). Moreover, explanted macrophages from $Bcg^r$ and $Bcg^s$ mice express a differential capacity to restrict the growth of ingested BCG (Stach et al., 1984, J. Immunol. 132: 888–892), *M. intracellulare* (Goto et al., 1989, Immunogenetics 30: 218–221), *Mycobacterium smegmatis* (Denis et al., 1990, J. Leukoc. Biol. 47: 25–30), *S. typhimurium* (Lissner et al., 1983, J. Immunol. 131: 3006–3013) and *L. donovani* (Crocker et al., 1984, Infect. Immunol. 43: 1033–1040) in vitro, indicating that this cell type expresses the genetic difference. The mechanism by which $Bcg^r$ macrophages exert enhanced cytocidal or cytostatic activity is not known, but they appear superior to $Bcg^s$ macrophages in the expression of surface markers (Ia and Acm-1 antigen) associated with the state of activation (Buschman et al., 1989, Res. Immunol. 140: 793–797) and the production of toxic oxygen and nitrogen radicals in response to secondary stimuli such as interferon γ and BCG infection, both in viva and in vitro (reviewed by Blackwell et al., 1991, Immunol. Lett. 30: 241–248; Skamene and Pietrangeli, 1991, Curr. Opin. Immunol. 3: 511–517).

Improper activation of the mononuclear phagocyte system can have profound deleterious consequences for the host, including the establishment of chronic infections, such as lepromatous leprosy and tuberculosis (Binford et al., 1982, J. Am. Med. Assoc. 247: 2283–2292). Additionally, $Bcg^r$ macrophages are more efficient in antigen presentation than their $Bcg^s$ counterparts (Denis et al., 1988, J. Immunol. 140: 2395–2400; ibid., 141: 3988–3993). Thus, through a more efficient presentation of self-antigens, $Bcg^r$ macrophages might thus be more likely to trigger an inflammatory response. Moreover, inappropriate regulation of activation, either by excess stimuli or insufficient suppression, can lead through inflammation, to extensive tissue damage such as in acute lung injury (Worthen et al., 1987, Am. Rev. Resp. Dis. 136: 19–28).

Although the mouse model has been instrumental in the elucidation of the intricacies of the immune system in humans, it does not serve as a good model for the study of tuberculosis and tuberculosis resistance in humans. Indeed, the mouse will only generally develop the pulmonary disease upon infection with very large doses (non physiological) of mycobacteria. At present the best animal models for tuberculosis are rabbits and hamsters.

The problems of sensitivity to infection by antigenically unrelated intracellular parasites, such as mycobacterium or Salmonella are not restricted to humans and mice. The meat and poultry industries, for example, suffer from recurrent infection problems linked to a number of such intracellular parasites. The major economical consequences derived from Salmonella infections in chicken is a case in point. Importantly, a genetic basis for the resistance/susceptibility phenotype to such intracellular parasites in a number of these other animal models has been suggested.

In spite of considerable interest in the study of natural resistance to infection with intracellular parasites its genetic basis remains unknown.

It would be highly desirable to identify the gene responsible for innate resistance to a wide variety of antigenically unrelated intracellular parasites including mycobacterial species, as well as to identify and characterize the protein encoded therefrom. It would also be highly desirable to identify the mouse Bcg gene and its encoded protein in order to understand the biochemical events leading to normal or aberrant macrophage activation, including acquisition of antimicrobial functions and the inflammatory response. It would still be highly desirable to identify the human gene and its encoded protein, responsible for this innate resistance.

It would further be desirable to obtain a mouse model for the study of tuberculosis.

In addition, it would be immensely useful to be able to identify individuals or animals which are susceptible to infection with antigenically unrelated intracellular parasites such as mycobacteria.

DISCLOSURE OF THE INVENTION

In humans, natural resistance or susceptibility to infection with mycobacteria such as *M. tuberculosis* and *M. leprae*, or *Leishmania donovani* and *Salmonella typhimurium*, have been shown to be under similar genetic control to that observed in inbred mice and directed by Bcg.

The present invention seeks to provide a nucleic acid segment isolated from an animal source comprising at least a portion of the gene responsible for natural resistance to infection with Mycobacteria and/or Leishmania and/or Salmonella (Nramp). The Nramp nucleic acid segment can be isolated using a method similar to those described herein, or using another method. In addition such nucleic acid can be synthesized chemically. Having the Nramp nucleic acid segment of the present invention, parts thereof or oligos derived therefrom, other Nramp sequences from other animal sources using methods described herein or other methods can be isolated.

The invention also seeks to provide prokaryotic and eukaryotic expression vectors harboring the Nramp nucleic acid segment of the invention in an expressible from, and cells transformed with same. Such cells can serve a variety of purposes such as in vitro models for the function of Nramp as well as for screening pharmaceutical compounds that could regulate the expression of the gene or the activity of the protein encoded therefrom. For example, such a cell, expressing a DNA sequence encoding a protein involved in macrophage function could serve to screen for pharmaceutical compounds that regulate macrophage function, and wherein the macrophage function comprises response to infection, killing of extracellular or intracellular targets and inflammatory response.

An expression vector harboring the Nramp nucleic acid segment or part thereof, can be used to obtain substantially pure protein. Well-known vectors can be used to obtain large amounts of the protein which can then be purified by standard biochemical methods based on charge, molecular weight, solubility or affinity of the protein or alternatively, the protein can be purified by using gene fusion techniques such as GST fusion, which permits the purification of the protein of interest on a gluthathion column. Other types of purification methods or fusion proteins could also be used.

Antibodies both polyclonal and monoclonal can be prepared from the protein encoded by the Nramp nucleic acid segment of the invention. Such antibodies can be used for a variety of purposes including affinity purification of the Nramp protein and diagnosis of the susceptibility/resistance predisposition to infection with a wide range of antigenically unrelated intracellular parasites.

The Nramp nucleic acid segment, parts thereof or oligonucleotides derived therefrom, can further be used to identify differences between individuals or animals that are susceptible or resistant to Mycobacterium species and the like. These nucleic acids can be additionally used to study the potentiation of macrophage resistance in an animal model, whether mouse or otherwise, following infection or challenge with Mycobacterium species and the like. The Nramp sequences can further be used to obtain animal models for the study of tuberculosis and the like. The functional activity of the Nramp protein encoded by these nucleic acids, whether native or mutated, can be tested in interspecies in vitro or in vivo models.

More specifically, the invention seeks to provide human Nramp and mouse Nramp nucleic acids and sequences hybridizing thereto under high stringency conditions. The human Nramp can be used in a DNA-based diagnostic assay to identify these individuals in the population who are at risk for the above mentioned types of infections. The human Nramp-1 DNA-based diagnostic assay can be used to identify individuals innately susceptible or resistant to BCG infection in populations where vaccination programs using BCG recombinant vaccines and prophylaxis of the above mentioned diseases are planned.

Further, the present invention seeks to provide the use of the Nramp protein as a pharmacological target for modulating macrophage function, including nonspecific host defense against infectious (intracellular) and tumor (extracellular) targets.

In general, the present invention relates to the determination that natural resistance to infection with intracellular parasites is conferred in mice by a gene, designated Nramp, in which mutations are associated with susceptibility to infectious diseases, such as tuberculosis, leprosy, salmonellosis and leshmaniasis in mice. The Nramp gene has been shown to regulate the growth of *Mycobacterium bovis* (BCG) and other taxonomically and antigenically infectious agents in the mouse. The sequence of the 2.48 Kb mouse Nramp cDNA clone, as is its deduced amino acid sequence are disclosed herein.

In addition, the mouse Nramp cDNA clone was used to probe a human cDNA library under non-stringent conditions, and surprisingly, permitted to show that not one, but at least two Nramp genes are expressed in humans. More particularly, one of these two human Nramp cDNA clones, was shown to be the homolog of mouse Nramp, and designated human Nramp-1. The sequence of the human Nramp-1 cDNA clone, as is its deduced amino acid sequence are also disclosed herein. The second members (Nramp-2) of mouse Nramp and human Nramp families have now been identified and characterized. Their nucleic acid sequences and deduced amino acid sequences are disclosed herein. It has now been surprisingly recognized that the Nramp genes are highly conserved between human and mouse. Further, this homology has now been unexpectedly shown to also be found with Nramp genes of other animals like rabbit, swine and even to chicken. Consequently, the present invention also relates to the isolation of Nramp genes from different animals, through the use of the nucleic acid sequences and the methods of the present invention.

Although the mouse model is not a very good animal model for tuberculosis in man, it has been traditionally used and continues to be used for immunological studies in general, and is a very important and relevant model for human mechanisms of defense based on the RE organs ("The cellular Basis of the immune response, An approach to immunology" Second Edition, 1981 E. S. Golub (Ed.), Sinaeur Associates Inc.). That the mouse model could serve as a valid model for human mechanisms of defense has been substantiated by the present invention. For example, according to the invention, the expression of Nramp-1 in mice is restricted to RE organs and further restricted to the macrophage compartment. The expression of human Nramp-1 is also restricted to RE organs and enriched in macrophage populations derived from these tissues. In addition, a very high sequence homology is observed between human and mouse Nramp (93% homology at the amino acid level for Nramp-1), strongly suggesting that these two Nramp proteins share the same function. Further, Nramp gene families are present in both mouse and human, the different Nramp genes identified are located on synthenic or homologous chromosomes, and they are surrounded by the same markers. Thus, according to the present invention the mouse model can serve as an animal model for tuberculosis in man.

In particular, the invention relates to a nucleic acid segment isolated from an animal source comprising a sequence encoding Nramp-1, a transmembrane protein displaying homology to nitrate transporters, involved in macrophage function, wherein macrophage function comprises response to infection, killing of extracellular or intracellular targets and inflammatory response.

The invention further relates to a substantially pure animal protein involved in macrophage function, wherein said macrophage function comprises response to infection, killing of extracellular or intracellular targets and inflammatory response.

More particularly, the invention relates to a method for identifying an alteration in a Nramp sequence encoding a protein conferring innate susceptibility or resistance to antigenically unrelated intracellular parasites wherein said determination of the presence of the alteration comprises hybridization of a sample of DNA or RNA from said animal with at least one sequence-specific oligonucleotide.

The identification of a difference between a resistant or a susceptible animal, such as a polymorphism, can be instrumental in the pinpointing of a specific alteration such as a point mutation. The identification of a point mutation associated with susceptibility can lead to a diagnostic assay to screen large populations in endemic areas of disease.

Moreover, the invention relates to a method for the isolation of a cDNA or gene using a positional cloning approach, wherein said gene product is unknown and a reliable in vitro assay for gene function is unavailable.

The designation Nramp as used in the present specification and claims refers to Nramp cDNAs or genes in animals in general. It is to be understood that the Nramp designation refers to genes encoding proteins which are homologous but not necessarily involved directly in natural resistance to infection to antigenically unrelated parasites. The numbering of the nucleotide and amino acid sequences and of the transmembrane domains and other landmarks of the proteins are based on the original sequences. Due to the identification of a further exon in mouse Nramp-1 for example, TK2 should actually be TX4 and $Gly^{105}$ should actually be $Gly^{169}$. As intended herein, humans are understood as being generally covered by the term animal. Nramp is intended to cover for example the NRAMP and Nramp designations, generally used for human and mouse, respectively. The designation functional variant is to be interpreted as meaning that the variant retains the biological activity of the protein from which it might originate.

As used herein in the specifications and appended claims, the term "oligonucleotide" includes both oligomers of ribonucleotides and oligomers of deoxyribonucleotides.

The term high stringency hybridization conditions, as used herein and well known in the art, includes, for example: 5×SSPE (1×SSPE is 10 mM Na-phosphate, pH 7.0; 0.18 M NaCl; 1 mM $Na_2$ EDTA), 5×Denhardt's solution (from a 100×solution containing 2% BSA, 2% Ficoll, 2% polyvinyl pyrollidone), 0.1% SDS, and 0,5 mg/ml denatured salmon sperm DNA, at 65° C. Other conditions considered stringent include the use of formamide. An example of washing conditions for the blot includes, as a final stringency wash, an incubation of the blot at 65° C. in 0.1×SSPE, 0.1% SDS for 1 hour.

In the specifications and appended claims, it is to be understood that absolute complementarity between the primers and the template is not required. Any oligonucleotide having a sufficient complementarity with the template, so that a stable duplex is formed, is suitable. Since the formation of a stable duplex depends on the sequence and length of the oligonucleotide and its complementarity to the template it hybridizes to, as well as the hybridization conditions, one skilled in the art may readily determine the degree of mismatching that can be tolerated between the oligonucleotide and its target sequence for any given hybridization condition.

Other features and advantages of the invention will be apparent from the description of the preferred embodiments invention, and from the claims.

BRIEF DESCRIPTION OF THE DRAWINGS

Figures 2A, 2B, 2C, 2D, 2E, 2F:
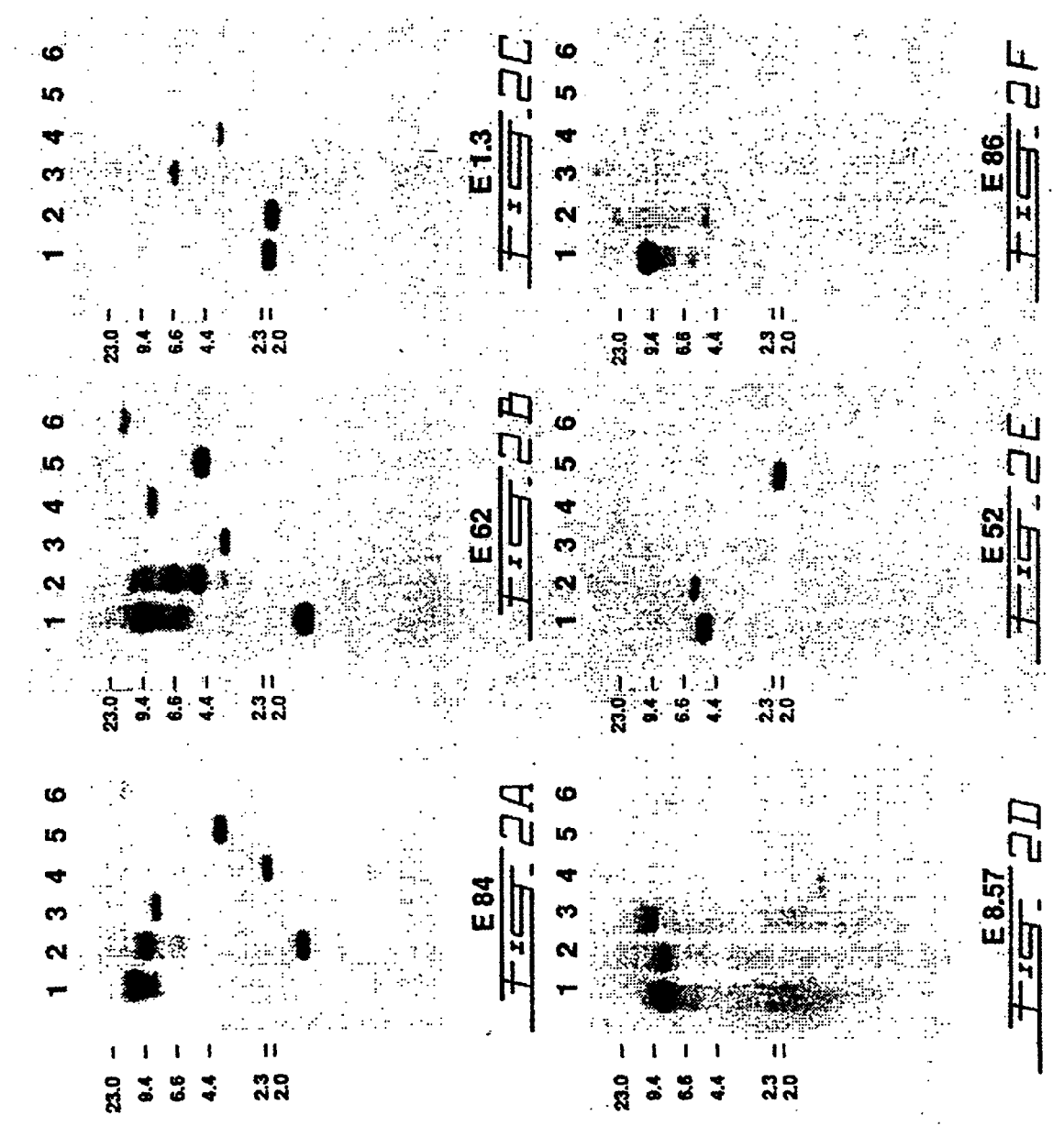

FIGS. 2A–F are Southern blots of genomic DNA from distantly related species ("Zoo blots") probed with different mouse exon probes (E).

FIGS. 3A, C, E, and G are Northern blots containing cellular RNA from normal mouse tissues and mouse cell populations probed with different mouse exon probes (E);

FIGS. 3B, D, F, and H are Northern blots containing cellular RNA from cultured cells from different mouse tissue types probed with different mouse exon probes (E);

FIGS. 3I and J are the ethidium bromide staining of the gels corresponding to the autoradiograms shown on their left;

FIG. 4 shows the nucleotide sequence and the deduced amino acid sequence of the cDNA clone encoding the mouse Nramp transcript and the Nramp protein;

FIG. 5 shows an alignment of the consensus transport sequence alignment detected in bacterial and eukaryotic transporters and shared by the mouse Nramp.

FIG. 6 summarises the results of nucleic acid sequence analysis of Nramp cDNA clones isolated from a series of 27 different Bcg$^r$ and Bcg$^s$ mouse strains.

FIG. 7 shows the sequence alignment between mouse and human Nramp-1 and Nramp-2 proteins.

FIG. 8 shows the protein sequence homology between the TM$_2$ region of Nramp-1 between mouse, chicken, rat and human.

MODES FOR CARRYING OUT THE INVENTION

Figure 1A:
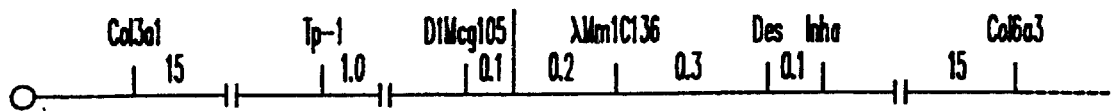
FIG. 1A is a summary of the genetic map of the mouse chromosome 1 segment harboring Bcg, from proximal marker Col3a1 to distal marker Col6a3.

In the absence of either a known gene product is or a reliable in vitro assay for gene function, a positional cloning approach to isolate the Bcg gene was chosen. Bcg maps on the proximal portion of mouse chromosome 1, close to the villin (Vil) gene (Malo et al., 1993, Genomics 16: 655–663). Using known marker loci and new anonymous probes obtained from a chromosome 1 micro-dissected library or generated by chromosome walking, a high resolution linkage map of mouse chromosome 1 was constructed (Malo et al., 1993, Genomics 16: 655–663). This mouse chromosome 1 segment of 30 cM overlapping Bcg, was found to be syntenic with a portion of human chromosome 2q in a segment delineated by loci COL3A1 (2q31–2q32.3) and COL6A3 (2q37) (Malo et al., 1993, Genomics 16: 655–663). After delineation of the maximal genetic and physical intervals defining the boundaries of the Bcg candidate gene region (Malo et al., 1993, Genomics 16: 655–663, and ibid 17: 667–675, respectively), a large segment of this domain was isolated in yeast artificial chromosomes (YAC), cosmid, and bacteriophage clones. This cloned genomic domain was analyzed for the presence of transcription units, and this eventually lead to the identification of a candidate gene for mouse Bcg.

Using the mouse Nramp cDNA (MNramp), it has been surprisingly discovered that at least two (2) Nramp genes are present and expressed, and thus, that in humans, a gene family of Nramp genes exists. Consequently, in order to identify the human counterpart of mouse Nramp, both potential human homologs of the mouse Nramp gene (HNramp-1 and HNramp-2) had to be analyzed. It now has been surprisingly discovered that mouse also contain at least two (2) Nramp genes. Furthermore, using mouse Nramp and/or human Nramp probes on Zoo blots under low stringency hybridization conditions (FIG. 2), that chicken and pig might contain a minimum of three (3) Nramp genes. The possibility that a third Nramp gene be identified in human and mouse thus remains and has been suggested by Dosik et al., 1994 (Mamm. Genome 5:458).

I. Genomic DNA Cloning in the Vicinity of Bcg

Figure 1B:
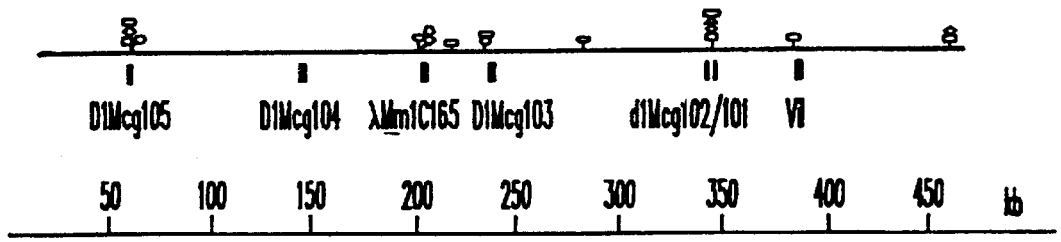
FIG. 1B is a physical map of the Bcg gene region obtained by pulse field gel electrophoresis of mouse genomic DNA digested with restriction enzymes NotI (○) , AscI (Δ), MluI (□), NruI (◎), BssHII (◯), and SacII (◇)

The linkage analysis in back-crossed mice and recombinant inbred strains was previously carried out and established at 0.3 cM the maximum genetic interval delineating Bcg (Malo et al., 1993, Genomics 16: 655–663). This interval includes the gene for the cytoskeleton protein villin (Vil) and the anonymous microdissected probe λMn1C165, neither of which shows recombination with Bcg in 1424 meioses tested. This maximum genetic interval was defined by single crossovers detected between D1Mcg105 and Bcg on the proximal side (1683 recombinants tested) and between λMm1C136 and Bcg on the distal side (575 recombinants tested; FIG. 1A). Pulse field gel electrophoresis (PFGE) and fluorescence in situ hybridization were then used to construct a long-range physical map of the Bcg region. The single copy probes used to construct the map are shown immediately below the map of FIG. 1B. The locus order and physical distances were found to be D1Mcg105-(160 kb)-λMm1-C165-(80 kb)-Vil-(800 kb)-λMm1C136, indicating a maximal physical interval for Bcg of 1.1 Mb (FIG. 1B). The size estimate of the minimal Bcg interval (D1Mcg105 to λMm1C136) obtained by physical mapping is superior to that predicted by recombination analysis, possibly owing to uneven distribution of crossovers on this part of the chromosome (Malo et al., 1993, Genomics 17: 667–675).

Figure 1C:
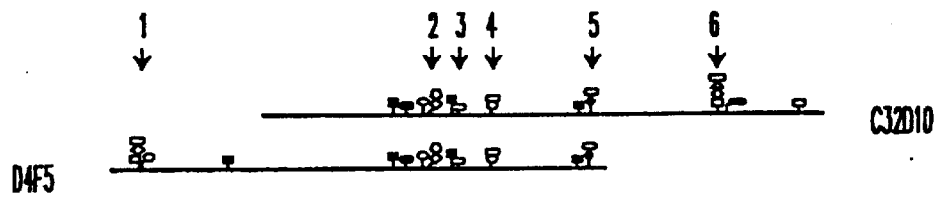
FIG. 1C shows the position of the two YAC clones C32D10 and D4F5, together with their restriction enzyme map for the series of enzyme shown in FIG. 1A.
Figure 1C:

To initiate the identification of candidate genes in the defined Bcg interval, the Princeton mouse YAC library (Burke et al., 1991, Genome 1: 65) was screened by a polymerase chain reaction (PCR)-based protocol (Rossi et al., 1992, Proc. Natl. Acad. Sci. USA 89: 2456–2460), using as entry probes the two tightly linked DNA markers Vil and λMm1C165. Primers Vil.1 (5'-TAGGAGGTTATGAGCCCGAAAGTG-3'; SEQ ID NO:7) and Vil.2 (5'-CTCAGGGAGAT-CCTCTACAGACTT-3'; SEQ ID NO:8) amplified a unique 120 bp Vil genomic DNA fragment, while primers 165.1 (5'-TGGTGCCCTGAGCATAGAGACTG-3'; SEQ ID NO:9) and 165.2 (5'-GTGGTATTTCGTGGTTGTCAGCCG-3'; SEQ ID NO:10) amplified a 110 bp λMm1C165 genomic DNA fragment. Parameters for the PCR amplification were 1 min at 94° C., 1 min at 65° C., and 1 min at 72° C. for 30 cycles, followed by a final extension period of 10 min at 72° C., under experimental conditions suggested by the supplier of Taq DNA polymerase (BIOCAN, Montréal). The PCR products amplified from complex or simple pools of YAC clones were analyzed by electrophoresis in 2% agarose gel, and specific products were visualized either by direct ethidium bromide staining or by Southern blotting and hybridization to sequence-specific probes (i.e., the corresponding $^{32}$P-labeled PCR amplification products obtained from cloned DNA using primers Vil.1–Vil.2 and 165.1–165.2). Single YAC clones corresponding to Vil (C32D10) and λMm1C165 (D4F5) were further purified and isolated by filter hybridization and expanded in culture using yeast S. cerevisiae strain AB1380 grown in selective medium lacking uracil and tryptophan (Vidal et al., 1993, Cell 73: 469–485). The two positive YAC clones, D4F5 and C32D10 are 240 kb and 280 kb, respectively (FIG. 1C). The restriction enzyme map of the two clones was established by PFGE for the enzymes previously used to construct a physical map of the Bcg genomic region.

Yeast chromosomes were prepared in agarose blocks. Agarose block slices (25 μl) were incubated with restriction enzymes NotI, MluI, NruI, BssHII, SacII, or AscI (New England Biolabs, Beverley, Mass.) under the conditions recommended by the supplier. The digested DNA fragments were separated by electrophoresis in a 1% agarose gel (SeaKem/FMC™, Rockland, Me.) containing 0.5×TBE (1×TBE is 0.1 M Tris, 0.1 M boric acid, 0.2 mM Na$_2$EDTA [pH 8.0]) using a contour-clamped homogeneous electric field (CHEF-DRII™, Bio-Rad) configuration. Electrophoresis was performed at 200 V for 20 hr at 15° C. with 15 s pulse times, allowing resolution of fragments in the range 20–400 kb. A oligomers (Pharmacia) and AB1380 yeast genomic DNA were used as size standards. Southern blots of these gels were prepared, and a physical map of the YAC DNA insert was determined after sequential hybridization of the blots to $^{32}$P-labeled individual single-copy probes from the region (Vil, D1Mcg101, D1Mcg102, D1Mcg103, D1Mcg104, and λMm1C165), to plasmid fragments specific to each YAC cloning arm, and to total genomic mouse DNA. The left end probe was the larger and the right end probe the smaller of the two fragments produced by double-digestion of pBR322 with PvuII and BamHI. The restriction maps of the genomic DNA region and the corresponding YAC clones, together with the positions of the hybridization probes used for mapping, are shown in FIGS. 1B and 1C. The two YAC clones span a 400 kb segment and have a 170 kb region of overlap, which includes one of the entry probes, λMm1C165 (FIG. 1C). A comparison of the composite restriction maps of the two overlapping YACs with that of genomic DNA shows concordance of both maps, suggesting that the two YAC clones carry non-chimeric inserts representative of the corresponding genomic DNA domain. Several additional rare-cutter sites were detected in both YACs that were absent in the genomic DNA (these sites are identified as closed symbols in FIG. 1C). The presence of newly accessible restriction enzyme sites in YAC clones has been previously documented (Wilkes et al., 1991, Genomics 9: 90–95) and has been attribued to the absence of DNA methylation of cytosines in yeast cells.

To study this region further, a contig of cosmid and bacteriophage clones was constructed from the genomic domain isolated in the two YAC clones. Total genomic DNA from yeast strains carrying the D4F5 and C32D10 YACs was used to create a cosmid and a bacteriophage library, respectively. High molecular weight genomic DNA was isolated from yeast cultures foolowing standard procedures. Total genomic DNA from the yeast clone carrying YAC D4F5 was partially digested with MboI, dephosphorylated with calf intestinal phosphatase (0.3 U/μg, Boehringer Mannheim), and size fractionated by centrifugation (200,000×g, 3 hr, 25° C.) on a continuous NaCl gradient (1.25–5 M). Fractions containing fragments larger than 30 kb were ligated into the BamHI cloning site of cosmid vector SuperCos™ (Stratagene), packaged in vitro (Gigapack II Gold™, Stratagene), and used to infect *Escherichia coli* strain DH5, which was subsequently plated on medium containing ampicillin (50 μg/ml). To identify mouse-specific clones, colonies were gridded in duplicate onto nylon filters (Hybond™, Amersham) followed by hybridization to a 32P-labeled total genomic mouse DNA. Approximately 10% of the library ($3 \times 10^4$ clones per pg of genomic DNA) was found to contain mouse-specific inserts by this approach. The DNA insert of YAC clone C32D10 was subcloned by a similar approach, except that it was introduced as a partial MboI digest into the BamHI site of the bacteriophage vector λEMBL3™ (Stratagene). Cloning efficiency was $1.2 \times 10^5$ pfu per μg of genomic insert DNA, and 3% of the clones were found to be mouse-specific. Cosmid and bacteriophage clones were expanded in culture and purified by standard protocols. A total of 40 cosmid and 30 phage clones hybridizing to total mouse DNA were isolated from these libraries; additional cosmid clones hybridizing to probes Vil, λMm1C165, and D1Mcg105 were obtained directly from a total mouse genomic library. Cosmid and phage clones were ordered by fingerprinting with enzymes EcoRI and HindIII and by hybridization to either total mouse DNA or single-copy probes from the region. This analysis allowed the construction of a cosmid and phage contig that spans approximately 400 kb and includes the two markers (Vil and λMm1C165) most tightly linked to the Bcg gene (FIG. 1C). The combined restriction maps of the YAC, cosmid, and phage clones from the region identified at least six CpG islands (numbered 1 to 6 in FIG. 1C), as defined by the clustering of two or more sites for enzymes with multiple CpG dinucleotides in their palindromic recognition sequences. Such CpG islands are often associated with the 5' end of transcribed genes and have been used as landmarks to identify coding sequences within large genomic DNA domains (Vidal et al., 1993, Cell 73: 469–485).

II. Exon Amplification in the Cloned Domain

The technique of exon amplification was used to initiate a systematic search for candidate transcription units within the cloned cosmid contig. This method is based on the functional screening for splicing competent exons within a cloned genomic DNA fragment. The screening for splicing competent exon could also be accomplished by exon trapping or gene tracking (Rommens et al., 1993, Hum. Mol. Genet. 2: 901–907). Exon amplification was performed exactly as described by (Buckler et al., 1991, Proc. Natl. Acad. Sci. USA 88: 4005–4009). Cosmid clones cosvil7, cosvil17, scos9.1, scos2.2, and scos21.1 were independently digested (4 hr, 37° C.) with restriction enzymes BamHI and BglII (Pharmacia) and subcloned as pools (one ligation per cosmid digest) into BamHI-digested and dephosphorylated pSPL1™ cloning vector, followed by transformation into *E. coli* strain DH5. The transformed cells were directly inoculated into 10 ml of LB broth containing ampicillin (50 μg/ml) and grown overnight, and plasmid DNA was isolated by the alkaline lysis method. Cloning efficiency was determined by parallel plating of transformed cells onto agar plates and was always superior to $2 \times 10^4$ colonies per μg of pSPL1™ plasmid. COS-7 monkey cells were transiently transfected by electroporation using 5–10 μg of each DNA pool, followed by incubation at 37° C. for 72 hr, at which point cytoplasmic RNA was isolated as described by (Buckler et al., 1991, Proc. Natl. Acad. Sci. USA 88: 4005–4009). For first-strand cDNA synthesis, 1–5 μg of cytoplasmic RNA was incubated with 20 pmol of pSPL1-specific oligonucleotide primer SA4 (5'-CCCGTCGACCACCTGAGGAGTGAATTGGTCG-3': SEQ ID NO:11) and incubated with 200 U of Moloney murine leukemia virus reverse transcriptase in a final reaction volume of 25 μl, under conditions suggested by the supplier of the enzyme (GIBCO-BRL). Trapped genomic exons were PCR amplified from the hybrid human immunodefiency virus tat cDNAs generated by the splice vector using tat-specific oligonucleotide primers SA4 and SD2 (5'-GTGAACTGCACTGTGACAAGCTGC-3'; SEQ ID NO:12). PCR-amplified exons were purified by gel electrophoresis and subjected to a second round of amplification using additional primers SA1 (5'-CCCGTCGACGTCGGGTCCCCTCGGGATTGG-3'; SEQ ID NO:13) and SD1 (5'-CCCGGATCCGCGACGAAGA, CCTCCTCAAGGC-3'; SEQ ID NO:14) immediately flanking the pSPL1 cloning site, using the PCR parameters and conditions described by (Buckler et al., 1991, Proc. Natl. Acad. Sci. USA 88: 4005–4009). Finally, amplified exons were purified by electrophoresis on low melting agarose gels and cloned directly into a dT-tailed (Marchuk et al., 1991, Nucl. Acids Res. 19: 1154) EcoRV-digested pBluescript II™ KS (+) plasmid vector (Stratagene). In this manner, a total of 22 putative exons ranging from 69 to 450 bp were recovered from these cosmids, and a summary of their characteristics is presented in Table 1.

In Table 1, (a) identifies individual cosmids derived from the cloned domain and used in exon amplification together with the names of individual exons derived from each of these cosmids; (b) the size of each exon was established by nucleotide sequencing; for the "Zoo blot" (c), evolutionary conservation of the cloned exons was determined by hybridization to Southern blots of genomic DNA from distantly related eukaryotes (see FIG. 3); (d) detection of corresponding mRNA transcripts was done by Northern blot analysis using total RNA from several normal mouse tissues and cell lines; (e) when indicated, cDNA clones corresponding to individual exons were isolated from two cDNA libraries constructed from the pre-B cell line 70/Z and normal rat brain; (f) common patterns of hybridization to cellular mRNAs detected in Northern blot analyses and/or cross-hybridization of cloned cDNAs to independent exons were used to order some of the identified exons into candidate (cd) transcription units (cd1 to cd6).

TABLE 1

Characteristics of Individual Exons Amplified from the Cloned Domain

| Cosmid[a] | Exon | Size[b] (bp) | Zoo Blot[c] | Northern Blot[d] | cDNA[e] | Transcript Specified[f] |
|---|---|---|---|---|---|---|
| cosvi17 | E5 | 85 | ND | ND | – | |
| | E32 | 163 | ND | + | ND | Vil |
| cosvi11 | E51 | 69 | ND | ND | – | |
| 7 | E37 | 89 | ND | – | – | |
| | E50 | 92 | ND | – | – | |
| | E45 | 187 | – | – | – | |
| | E52 | 186 | + | + | + | cd5 |
| | E59 | 400 | + | + | + | cd2 |
| | E62 | 450 | + | + | + | cd2 |
| scos 21.1 | E15.1 | 200 | – | – | – | |
| cos 165.1 | E76 | 99 | – | ND | ND | |
| | E84 | 341 | + | + | + | cd1 |
| | E92 | 123 | – | – | – | cd6 |
| | E93 | 118 | – | + | + | cd1 |
| | E73 | 180 | + | + | + | cd1 |
| | E86 | 173 | – | – | + | cd6 |
| scos 2.2 | E8.57 | 220 | + | – | + | cd4 |
| | E9.64 | 200 | – | – | – | |
| scos 9.1 | E1.3 | 250 | + | – | + | cd3 |
| | E1.6 | 450 | + | – | – | |
| | E3.17 | 210 | ND | ND | – | |
| | E6.42 | 175 | – | ND | – | |

Several criteria were used to distinguish bona fide exons from false positives and to group these true exons into transcription units. These included nucleotide sequencing and comparison to DNA sequence data bases (GenBank™ and EMBL™) and the capacity of discrete exons to recognize the following in hybridization experiments: the corresponding cosmid clone used to construct the pSPL1 library, genomic DNA sequences from distantly related species ("Zoo blots"), and specific mRNA transcripts or cDNA clones.

Initially, all exons were sequenced, and a homology search in the GenBank™ and EMBL™ data bases failed to detect homologous sequences, except for exon E32 (cosvi7), which was found to be part of the mouse Vil gene (89% identity to human VIL). Exons larger than 99 bp were then assessed for cross-species homology, using "Zoo blots" of genomic DNA from mouse, rat, human, pig, chicken, and fish (respectively, lanes 1, 2, 3, 4, 5 and 6 in FIG. 2). "Zoo blots" were prepared using BamHI-digested DNA (5–10 U per μg of DNA) from rat (liver), human (Epstein-Barr virus-transformed lymphoblasts), pig (liver), chicken (blood) and fish (liver), and fragmentation products were separated by electrophoresis in 1% agarose gels in TAE buffer, followed by capillary transfer to nylon membranes (Hybond) in 20×SSC (1×SSC is 0.15M NaCl, 0.015M sodium citrate). The low stringency hybridization conditions of the "zoo blot" included prehybridizations for 16 hr at 42° C. in a mixture of 35% formamide, 5×SSC, 1% SDS, 10% dextran sulfate, 0.02M Tris (ph 7.5), 1×Denhardt's solution (0.1% bovine serum albumin, 0.1% Ficoll™ 0.1% polyvinylpyrrolidone), and denatured salmon sperm DNA (200 μg/ml). Hybridizations were performed in the same solution containing the $^{32}$P-radiolabeled probe (1×10$^6$ cpm/ml). The hybridized membranes were washed to a final stringency of 0.5 ×SSC, 0.1% SDS at 60° C. for 30 min. As summarized in FIG. 2 and Table 1, eight (8) of sixteen (16) exons tested by the "Zoo blot" approach showed cross-species conservation.

Figure 1D:
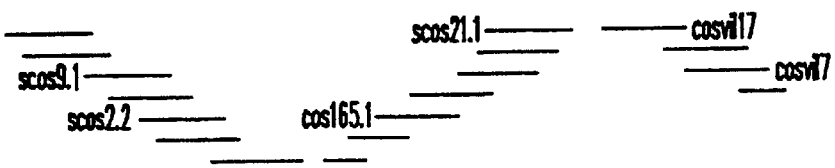
FIG. 1D shows the organization of the cosmid and bacteriophage clones contig assembled from the two YAC clones.
Figure 1D:
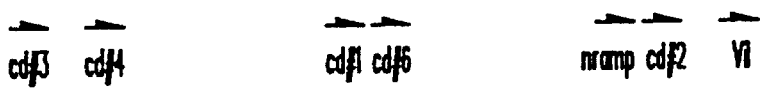

Northern blot analysis was carried out in order to identify the exons that could detect discrete mRNA transcripts. Total RNA was prepared from normal mouse tissues and cultured cells. Murine lymphoid tumor cell lines L1210 and P388, and monkey COS-7 cells were originally obtained from Dr. D. Housman (Massachusetts Institute of Technology, Cambridge, Mass.). Murine LTA and NIH 3T3 fibroblasts were given by Dr. C. P. Stanners (McGill University, Montréal). J774A macrophages (ATCC accession number TIB67), RAG renal adenocarcinoma cells (ATCC accession number CCL142), adrenal cortex tumor cell line Y1 (ATCC accession number CCL79), were obtained from American Type Culture Collection. CT26 cells were obtained from Dr. N. Beauchemin (McGill University, Montréal). Rat hepatoma cell lines H35 and HCT were a gift of Dr. R. Levenson (Yale University, New Haven, Conn.). Adherent cells were grown in alpha-minimal essential medium (α-MEM) supplemented with 10% fetal calf serum, 2 mM L-glutamine, and antibiotics (50 U/ml penicillin and 50 μg/ml steptomycin), while cells in suspension were grown in RPMI 1640 supplemented with 10% fetal calf serum, 2 mM L-glutamine, 20 μM β-mercaptoethanol, and antibiotics. Splenic macrophages were isolated from CBA/J (Bcg$^r$) and C57BL/6J (Bcg$^s$) mice. To isolate enriched populations of splenic macrophages, groups of five mice were sacrificed by cervical dislocation, and their spleens were aseptically removed. The spleens were gently teased with a scalpel and tweezers, and spleen cells were dispersed in 10 ml of cold complete RPMI 1640 (supplemented with 10% heat-inactivated fetal calf serum) using a syringe fitted with a 22 g needle. Viable cells (2.5×10$^7$) were plated in 15 ml of medium (150 mm dish) and allowed to adhere to the plastic surface by incubation at 37° C. for 4 hr in a 5% CO$_2$ atmosphere. Nonadherent cells were removed by successive washes with warm phosphate-buffered saline, and adherent cells were detached using a rubber policeman after a 10 min incubation in cold phosphate-buffered saline. Between 2×10$^6$ and 8×10$^6$ viable adherent cells per mouse spleen could be purified by this method. The RNA was extracted using 6 M guanidinium hydrochloride and purified by sequential ethanol precipitations and phenol-chloroform extractions. Total RNA (10 μg) was fractionated by electrophoresis in 1% agarose gels containing 0.66 M formaldehyde and MOPS buffer (1×MOPS is 40 mM morpholinopropanesulfonic acid, 10 mM sodium acetate, 10 mM EDTA [pH 7.2]) and blotted onto nylon membranes (GeneScreen Plus™, New England Nuclear) in 10×SSC. RNA blots were prehybridized for 2 hr at 65° C. in 1 M NaCl, 1% SDS, 10% dextran sulfate, and denatured salmon sperm DNA (100 µg/ml). Hybridization was performed for 20 hr at 65° C. in the same solution containing the $^{32}$P-radiolabeled probe ($0.5 \times 10^8$ to $1 \times 10^8$ cmp/ml), and hybridized membranes were then washed at a final stringency of 0.1×SSC, 1% SDS at 65° C. Autoradiography of all hybridized filters was performed with Kodak XAR™ film at −80° C. with an intensifying screen. All hybridization probes were labeled to high specific activity ($10^9$ cpm per pg of DNA), using [α-$^{32}$P]dATP (DuPont, NEN Research Products, Boston, Mass.) by the random priming method. In this manner, 6 exons were grouped into three independent candidate transcription units (Table 1 and FIG. 3A–J): E73, E84, and E93 detected a 1.5 kb transcript (candidate 1), E59 and E62 detected a 3.6 kb mRNA (candidate 2), and E52 detected a 2.5 kb transcript (candidate 5). However, many exons did not detect discrete mRNA transcripts by Northern blot analysis, possibly owing to low abundance or cell type-specific expression. Screening of cDNA libraries constructed in bacteriophage vectors λgt10 and λgt11 and obtained by priming mRNA (pre-B cell line 70/Z; (Gros et al., 1986, Nature 323: 728–731) with oligo(dT) or random hexamers, respectively, and inserting the cDNA inserts in the unique EcoRI site of λgt10 or λgt11, with all candidate exons, independently or as pools was also performed. In addition, probes E8.57 and E1.3 were used to screen a cDNA library constructed in vector λgt11 and obtained by priming rat brain mRNA with random hexamers (R. Dunn, McGill University, Montréal). Positive phage clones were plaque purified by routine methods, and their insert was subcloned into the unique EcoRI site of plasmid vector pBluescript II KS(+) or bacteriophage M13mp18, two examples of prokaryotic vectors. Three additional candidate transcription units were identified in these screens: exon probes E8.57 and E86 each identified, in the pre-B cell mouse library, independent sets of overlapping clones corresponding to candidates 4 and 6, respectively, while exon probe E1.3 identified, in the rat brain library, another group of cDNAs corresponding to candidate 3 (Table 1). Therefore, 11 of the 22 putative exons defined a minimum of seven independent transcription units within the Bcg gene region, which included the Vil gene and candidates 1 to 6 (FIG. 1D).

III. Characterization of Candidate Transcription Units Near Bcg

Complementary DNA clones corresponding to the six candidate genes were isolated and used to determine their pattern of tissue-specific expression. Searches were conducted for genes expressed in the RE organs, such as the spleen and liver, and in particular for genes expressed in the mature tissue macrophages populating these organs, since these cells have been shown to be responsible for the phenotypic expression of Bcg. Genes whose expression profile included one of these tissues were further characterized by nucleotide sequencing of corresponding cDNAs. Nucleotide sequencing was performed by the dideoxy chain termination method, using modified T7 DNA polymerase (Pharmacia) and denatured double-stranded DNA templates or single-stranded M13mp18 recombinant phage template. Oligonucleotide primers were derived from the known sequence of the cDNA inserts or were plasmid based and flanked the cloning site used. In the case of Nramp and candidates 1 and 2, cDNA clones were obtained and characterized by nucleotide sequencing using at least two independent clones.

The expression profile of each candidate was established by Northern blot analysis, using total cellular RNA from normal mouse tissues and a number of cultured cell lines of distinct tissue origin (FIG. 3A–J) and the exposure times were either 12 hr (E84 and E62) or 72 hr (E52, E1.3, E8.57, and E86) and reflect the relative abundance of each transcript.

Vil, originally used as an entry probe to screen the YAC genomic library, was identified by nucleotide sequencing of exon E32 (cosvil7). In Northern blots, probe E32 detected a 3.8 kb mRNA that was expressed exclusively in intestine and kidney and was absent from organs and cell types of the RE system. Villin is a cytoskeleton protein that participates in the $Ca^{2+}$-dependent assembly of actin filaments in epithelial cells of the gastrointestinal and urogenital tract.

Candidate 1 was identified by exon probe E84 (cos165.1; FIGS. 1C and 1D). E84 showed very strong cross-species conservation on the "Zoo blot" (FIG.2A) and detected 1.4 and 1.5 kb mRNA species expressed abundantly in a large number of tissues and cell types, including those of the RE system (FIGS. 3A and 3B). The highest levels of expression of this gene were detected in RNA from testis, spleen, embryo, the macrophage cell line J77A4, macrophage and lymphocyte populations of the spleen (FIG. 3A), and other cell lines of unrelated tissue origin (FIG. 3B). A set of overlapping cDNA clones were then isolated (clone frequency 1/500 in the pre-B cell library) and mapped with respect to the cloned domain. Hybridization to cosmid clones from the region showed that this gene is transcribed in the centromere to telomere direction, with its 5' end associated with CpG island 2 (FIG. 1C and 1d). Nucleotide sequence analysis revealed that the two mRNAs detected by Northern blot analysis have distinct 5' ends but share an open reading frame that could encode a protein of 244 amino acids; this protein appears highly hydrophilic and did not have homology with sequences deposited in the GenBank™, EMBL™, and SwissProt™ data bases. The EMBL™, GenBank™, and SwissProt™ data bases were searched using the GCG™ software package (Devereux, 1991, Version 7.0, Madison, Wis.: Genetics Computer Group, Inc.) on a DEC VAX™ computer (Université de Montréal, Montréal).

Candidate 2 was identified by exon probe E62 (cosvil7; FIGS. 1C and 1D). E62 also showed strong cross-species conservation on the "Zoo blot" (FIG. 2B) and detected two mRNA transcripts of 3.3 and 3.6 kb that were abundantly and ubiquitously expressed in most tissues and cell lines analyzed (FIGS. 3C and 3D). The highest levels of expression were detected in embryo, kidney, intestine, liver, and spleen, while in cultured cell lines only the P388 leukemia did not express this gene. Full-length cDNA clones for these transcripts were then isolated (frequency 1/1000 in the pre-B cell library), and hybridization experiments indicated that this gene is transcribed in the centromere to telomere direction, with the 5' end associated with CpG island 6 (FIGS. 1C and 1D). Nucleotide sequence analysis revealed that the two mRNA transcripts are generated from the same gene by the use of alternative polyadenylation signals, and both could encode a polypeptide of a minimum of 336 amino acids; like the candidate 1 gene product, this protein appears to be highly hydrophilic and does not have homology to sequences deposited in available data bases. Taken together, the ubiquitous nature and high levels of expression of candidates 1 and 2 in the panel of tissues and cell lines analyzed and their high degree of evolutionary conservation suggest that both genes may perform "housekeeping" functions.

Candidates 3, 4 and 6 were identified with exon probes E1.3, E8.57 and E86, respectively, which were amplified from three nonoverlapping cosmids (Table 1). Although evolutionary conservation was evident for some of these exons (E1.3 and E8.57; (FIGS. 2C AND 2D), all attempts to identify corresponding mRNAs by Northern blotting were unsuccessful (FIGS. 3G and 3H). Nevertheless, cDNA clones corresponding to each of these exons were successfully isolated. A 1.2 kb cDNA for candidate 3 was isolated from a rat brain cDNA library, using exon probe E1.3. Candidate 3 was found to map within cosmid scos9.1 at the proximal end of the cloned domain, distal to the locus D1Mcg105 and associated with CpG island 1 (FIGS. 1C and 1D). overlapping cDNA clones of 2.5 kb and 3 kb were identified for candidate 4 by exon probe E8.57 in the pre-B cell cDNA library. Candidate 4 was found to overlap cosmid scos2.2, mapped 50 kb distal to candidate 3, and was not associated with a CpG island (FIGS. 1C and 1D). Unfortunately, we could not position candidates 3 and 4 with respect to the single crossover detected by linkage analysis between Bcg and D1Mcg105 and delineating the proximal boundary of the Bcg interval (Vidal et al., 1993, Cell 73: 469–485). Finally, a 1.2 kb cDNA clone for candidate 6 was isolated from the pre-B cell library. This gene was found to be included in cosmid cosl65.1 and mapped near candidate 1, associated with CpG island 3 (FIGS. 1C and 1D). However, since RNA expression could not be detected for these genes in any of the normal tissues or cultures cells analyzed, they were not characterized further.

Candidate 5 was identified by exon probe E52 (cosvil17). This probe showed a high degree of evolutionary conservation on the "Zoo blot" (FIG. 2E) and was used to isolate corresponding cDNA clones from the pre-B cell library. Twenty-two positive clones were identified (frequency 1/100,000), the longest clone being 2.4 kb. Candidate 5 was found to be entirely contained within cosvil17, mapping 50 kb proximal to Vil, and transcribed in the centromere to telomere direction (FIGS. 1C and 1D). Northern blotting analyses in normal tissues indicated that candidate 5 codes for a 2.5 kb mRNA whose expression could only be detected in the spleen (FIG. 3E); however, prolonged exposure of the autoradiogram in FIG. 3E also indicated low level expression of this gene in another RE organ, the liver. Moreover, fractionation of spleen cells into macrophage-enriched (adherent) and lymphocyte-enriched (nonadherent) subpopulations showed that candidate 5 expression was restricted to and greatly enhanced in the macrophage compartment (FIG. 3E). Likewise, analysis of candidate 5 expression in cell lines from distinct tissue origins showed that expression of this gene was restricted to the murine macrophage cell line J774A (FIG. 3F). In conclusion, unlike the other candidate genes identified within the cloned domain, candidate 5 expression is restricted to RE organs and is enriched in macrophage populations derived from these tissues and in a macrophage cell line. Expression of this gene in tissues and cell types known to express Bcg phenotypically, together with its chromosomal location, makes it a strong candidate for the Bcg gene. This gene has been given the appellation natural resistance-associated macrophage protein gene, or Nramp.

Figure 4A:
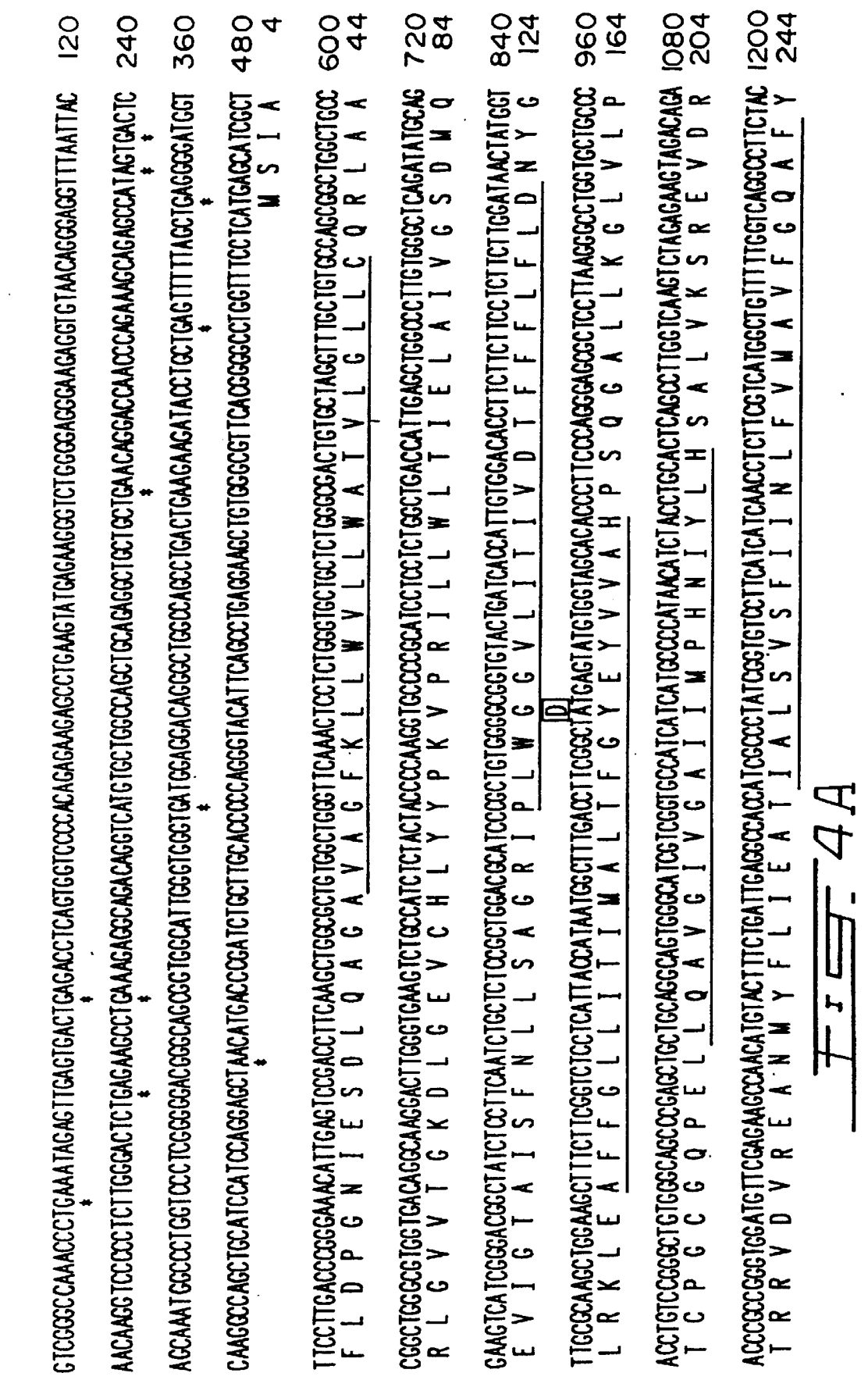

IV. Nramp Encodes a Novel Polypeptide with Characteristics of Prokaryotic and Eukaryotic Transport Proteins Several overlapping Nramp cDNA clones were isolated, and the complete nucleotide sequence of the longest Nramp clone (2.48 kb) is shown in FIG. 4 and in SEQ ID NO:1. Nucleotides are numbered positively in the 5' to 3' orientation to the right of each lane (top row), starting with the first nucleotide of the 5' untranslated region and ending with the last nucleotide, including eleven (11) adenines of the poly (dA) tail. The deduced amino acid sequence is shown below the nucleotide sequence. Amino acids are numbered to the right of each lane (bottom row), starting with the first in-frame methionine, and ending with the TGA termination codon (*), located immediately downstream of glycine 484. Predicted N-linked glycosylation sites are indicated by bracketed groups of residues corresponding to the sequence N-X-S/T, and predicted phosphorylation sites for protein kinase C (S/T-X-R/K) are circled. Highly hydrophobic segments corresponding to putative membrane-spanning (TM) domains are underlined. The binding-protein-dependent transport system inner membrane component signature (Kerppola and Ames, 1992, J. Biol. Chem. 267: 2329–2336) located between predicted TM6 and TM7 is indicated by a series of "m". The position of the glycine (G) to aspartic acid (D) substitution at position 105 within predicted TM 2, which is associated with susceptibility ($Bca^s$), is shown. The presence of several stop codons in all reading frames within the first 468 nt of the cDNA indicates that this region is untranslated. The first possible initiator ATG codon is followed by a segment of 1452 nucleotide, forming a single open reading frame that can encode a polypeptide of 484 amino acids with a predicted molecular weight of approximately 53,000 (FIG. 4 and SEQ ID NO:2). The in-frame termination codon (TGA) immediately downstream of Gly-484 is followed by 557 nucleotides of 3' untranslated region, ending with eleven (11) consecutive adenosine residues. The sequence immediately upstream of the poly(dA) tail contains an intact AATAAA polyadenylation signal. The size of the longest Nramp cDNA (2.48 kb) is compatible with the estimated size (2.5 kb) of the Nramp transcript expressed in splenic macrophages and macrophage cell lines (FIG. 3E).

A search of the GenBank™ and SwissProt™ date bases revealed that the Nramp gene encodes a polypeptide with no apparent sequence similarity to any previously identified protein. However computer-assisted analysis of the predicted amino acid sequence of the Nramp gene product using the motifs algorythm (Bairoch, 1991, Nucl. Acids Res. 19: 2241–2245) reveals a number of significant structural features. In particular, a hydropathy analysis identifies a series of strongly hydrophobic domains that are similar to the membrane-spanning regions of polytopic membrane proteins (Gros et al., 1986, Nature 323: 728–731).

The hydropathy plots were obtained by standard computer-assisted analysis, using the algorithm and hydropathy values of (Kyte and Doolittle 1982, J. Mol. Biol. 157: 105–132) for a window of eleven (11) amino acids, ten (10) potential transmembrane domains (TM) were identified. in the Nramp protein (underlined in FIG. 4), although as many as twelve (12) could be accommodated by the sequence. The Nramp gene product also contains two potential N-linked glycosylation site (N-X-S/T) at positions 257 and 271, clustered within a highly hydrophilic region between predicted TM 5 and TM 6 (FIG. 4), and two potential sites for phosphorylation by protein kinase C (S/T-X-R/K; Woodget et al., 1986, Eur. J. Biochem. 161: 177–184), one within a hydrophilic region flanked by predicted TM 4 and TM 5 (position 205) and another near the carboxyl terminus (position 466).

In addition, the Nramp protein contains a precisely conserved sequence motif known as the "binding-protein-dependent transport system inner membrane component signature", first identified in a group of bacterial transport proteins (Kerppola and Ames 1992, J. Biol. Chem. 267: 2329–2336). This twenty (20) amino acid transport motif spans positions 306 to 325 of Nramp and is located between predicted TM 6 and TM 7 (FIG. 4). Bacterial binding-protein-dependent transport systems, or periplasmic permeases, are multisubunit transporters composed of a periplasmic substrate-binding protein, one or two homologous inner membrane proteins, and one or two peripheral ATP-binding energy coupling subunits. The integral membrane subunits are highly hydrophobic and are believed to participate in substrate translocation across the membrane. Although these proteins show little primary sequence homology, they all share a similar predicted membrane organization, including a minimum of 5 TM domains and the conserved transport motif located amino-terminal to the last 2 TM domains (95 to 130 residues from their carboxyl terminus) on the cytoplasmic side of the membrane (Kerppola and Ames 1992, J. Biol. Chem. 267: 2329–2336). Alignment of the consensus transport sequence detected in bacterial and eukaryotic transporters and shared by Nramp is shown in FIG. 5. The sequence alignment of this motif is presented for the histidine (HisQ), maltose (MalF), phosphate (PstA, PstC), and molybdenum (ChlJ) bacterial transporters, together with the corresponding motifs detected in the eukaryotic nitrate transporter CrnA and in Nramp. In the alignment, the conserved residues are stippled and the degenerate consensus sequence is shown at the top. The evolutionary conservation of this motif in otherwise nonhomologous membrane components of bacterial transporters acting on different substrates probably reflects a common mechanistic aspect of transport. Indeed, it has been proposed that this protein fold may participate in physical interaction and/or functional coupling between the membrane subunits and the peripheral ATP-binding subunits (Kerppola and Ames, 1992, J. Biol. Chem 267: 2329–2336). Bacterial periplasmic permeases are members of the ATP-binding cassette superfamily of membrane transporters, which also includes homologs in lower and higher eukaryotes (Buschman et al., 1992, Int. Rev. Cytol. 137C: 169–197). These have been shown to participate in the outward translocation of specific substrates across cellular membranes. The conserved transport motif has not been retained by the eukaryotic ATP-binding cassette transporters, where the ATP-binding subunits and membrane anchors are integrated in the same polypeptide (Buschman et al., 1992, Int. Rev. Cytol. 137C: 169–197). However, a data base search revealed that a similar motif is present in certain eukaryotic transport proteins of the non-ATP-binding cassette type, including the ($Na^+,K^+$) ATPase of *Drosophila melanogaster* and the uracil permease of *Saccharomyces cerevisiae* (Vidal et al., 1993, Cell 73: 469–485). In this group, the permease for nitrate uptake encoded by the crnA gene of the eukaryote *Aspergillus nidulans* is of particular interest (Vidal et al., 1993, Cell 73: 469–485). Similarly to Nramp, the CrnA protein is composed of 483 amino acids, with 10 putative TM domains (Vidal et al., 1993, Cell 73: 469–485) and the conserved transport motif located between predicted TM 6 and TM 7 (FIGS. 4 and 5). Thus, while the Nramp protein shows little primary sequence homology to other membrane proteins, it does have structural similarities with a variety of bacterial and eukaryotic transport proteins. In particular, Nramp has similarity with the nitrate transporter CrnA, not only with respect to size and the number and distribution of hydrophobic domains, but also with respect to the presence and position of the conserved transport motif.

V. A Mutation in Predicted TM 2 of Mouse Nramp is Associated with the $Bcg^s$ Phenotype Kinetic analysis of mRNA levels in control and infected macrophages revealed that the level of Nramp gene expression was similar in $Bcg^r$ and $Bcg^s$ mice and did not fluctuate significantly during the course of infection in vivo. Therefore, to assess the candidacy of this gene further, we analyzed mRNA transcripts from $Bcg^r$ and $Bcg^s$ strains for the presence of sequence alterations in the coding portion of the Nramp gene. Two pairs of oligonucleotide primers were used to amplify Nramp-specific cDNAs by PCR from 2 $Bcg^s$ (BALB/cJ and C57BL/6J) and 3 $Bcg^r$ strains (C57L/J, C3H/HeJ, DBA/2J). The amplified products were then subcloned and fully sequenced. A single nucleotide difference was found to segregate between $Bcg^r$ and $Bcg^s$ mice: the 3 resistant strains presented a guanine at nucleotide 783 (amino acid 105), while the 2 susceptible strains presented an adenine at the same position (FIG. 6). This nucleotide variation results in a single amino acid change, a glycine to aspartic acid substitution at position 105 within the second predicted TM domain. In addition, two silent mutations were detected in the 5' portion of the Nramp transcript from C3H/HeJ mice, one at nucleotide 563 (Ala-32, GCG→GCC) and another at nucleotide 1169 (Phe-234, TTC→TTT); the other resistant and susceptible strains tested were identical at these two positions (Ala-32, GCG; Phe-234, TTC) (FIG. 6).

To confirm the segregation of the observed sequence variation between resistant and susceptible mouse strains the 5' half of the Nramp transcript has now been analyzed in a total of 20 $Bcg^r$ strains and 7 $Bcg^s$ strains. A compilation of the results is presented in FIG. 6. Among all the polymorphisms detected within Nramp in the 27 strains tested, four out of five were silent mutations. The first was a G→C transversion at nucleotide 565 (GCG→GCC, $Ala^{32}$, TM1) detected in A/J, C3H/HeJ, CBA/J. NZB/BlNJ, NOD/Lt and Mus spretus, the second was a C→A transversion at nucleotide 784 (GGC→GGA, $Gly^{105}$, TM2) specific to the SWR/J strain, the third was a C→T transition at nucleotide 1171 (TTC→TTT, $Phe^{234}$, TM5) in A/J, C3H/HeJ, NZB/BlNJ and CBA/J strains, and the fourth was a G→A transition at nucleotide 1444 (AAG→AAA, $Lys^{325}$, consensus transport sequence motif) specific to the NOD/Lt strain. The G→A transition at nucleotide 783 resulting in a Gly to Asp substitution at position 105 of Nramp within predicted TM2 was the only non-silent mutation identified in Nramp and was also the only one which segregated according to the Bcg type of all strains tested: the 20 BCG-R strains presented a guanine at nucleotide 783 ($Gly^{105}$), while the 7 BCG-S strains presented an adenine ($Asp^{105}$) at that position. Therefore, the analysis of 14 inbred strains of various ancestral origins confirmed and extended to 27 inbred strains the absolute association of the Gly vs Asp substitution at position 105 with the BCG-R and BCG-S phenotypes, respectively. Although this sequence analysis identified additional novel sequence polymorphisms within Nramp, they neither affected the predicted sequence of the protein nor were associated with the Bcg phenotype. A helical wheel representation of TM 2 reveals that this mutated residue maps on a strongly hydrophobic face of the proposed helix. Accordingly, a Gly to Asp substitution at this position would be expected to profoundly alter the physical properties of this proposed transmembrane domain. This could in turn affect the overall membrane-associated structure and/or membrane insertion of the protein in the susceptible mouse strains. These findings, together with the chromosomal location, the homology to the nitrate transporter CrnA, the role of simple oxidized nitrogen metabolites in the cytocidal response of macrophages to ingested intracellular parasites, and the macrophage-specific expression of Nramp, identify this gene as a strong candidate for Bcg.

The confirmation that Nramp indeed is Bcg has now been demonstrated in vivo in mouse by "knock out". Accordingly, it has been shown that the mutation in the transmembrane 2

(TM2) region of Nramp is sufficient to confer the sensitivity phenotype to a mouse having the proper genetic make-up for the experiment.

VI. Isolation of Two (2) Human Nramp cDNAS and an Additional Mouse Nramp cDNA

The strategy to isolate the human counterpart of mouse Nramp was based on two major findings:

1) the "Zoo blot" results showed that exon E62 (candidate 5; FIG. 2E) showed a high degree of evolutionary conservation, and identified a relatively strong human DNA band (FIG. 2E, lane 2); and 2) Northern blotting analyses indicated that E52 (candidate 5, Nramp) was expressed in liver, hence the screening of a liver cDNA library to isolate the human Nramp cDNA.

We thus reasoned that screening of a human liver cDNA library under low stringency conditions, similar to those used for the "Zoo blot", would yield the sought after human Nramp counterpart. A 1.2 kb Eco RI Sac II fragment from the mouse Nramp cDNA was used in a low stringency screen of a human liver cDNA library (Stratagene). One (1) putative human Nramp cDNA clone was isolated, sequenced and showed an approximately 75% homology to mouse Nramp. Using the same 1.2 kb Eco RI Sac II probe on a cosmid library under high stringency, a human genomic clone was isolated and sequenced. Surprisingly, however, comparison of the nucleotide sequences of the human cDNA clone and the human genomic clone indicated that they were different, suggesting that more than one gene for Nramp was present in humans. Since the genomic human Nramp clone was more closely related to the mouse Nramp cDNA clone than it was to the human cDNA clone, the former was termed human Nramp-1 (SEQ ID NO:3) and the latter human Nramp-2 (SEQ ID NO:5). Using the mouse Nramp cDNA and human Nramp-2 cDNA, gene specific probes were identified. A mouse Nramp specific probe was used at high stringency to screen a human spleen cDNA library and permitted the isolation of several human Nramp-1 cDNA clones. Similarly, a human Nramp-2 specific probe was used to re-screen the 70/Z mouse pre-B cDNA library and permitted the isolation of several cDNA clones corresponding to mouse Nramp-2 cDNA. One such cDNA clone, was sequenced and shown to comprise 2.967 kb (SEQ. ID NO:26). An AUG found at position 50 in SEQ. ID NO:26 initiates an open reading frame of 568 amino acids (SEQ. ID NO:26 and SEQ. ID NO:27) displaying substantial identity to MNramp-1 and its human counterparts. The initiator AUG has not been formerly identified since, while no upstream AUG is found upstream of the predicted initiator at position 50, the open reading frame shown in SEQ. ID NO:27 can be further extended at the N-terminus by translating from base pair position 2 in SEQ. ID NO:26, giving rise to a predicted protein of 584 amino acids (SEQ. ID NO:28).

The nucleic acid and amino acid sequences of human Nramp-1 (HNramp-1; 1.73 kb; SEQ ID NO:3) and human Nramp-2 (HNramp-2; 1.87 kb; SEQ ID NO:5) are shown in the sequence listing. A sequence mistake was identified in HNramp-2, as a C was shown to be missing between the two (2) A at positions 221 and 222, respectively (SEQ. ID NO:3). Insertion of the missing C permits a N-terminal extension of the open reading frame of HNramp-1 to yield a predicted protein of 550 amino acids (SEQ. ID NO:29 and SEQ ID NO:30) that initiates at an AUG found at position 80 of SEQ. ID NO:3. A one amino acid change at the N-terminus of HNramp-2 has been corrected in SEQ ID NO:31 and SEQ ID NO:32. The human Nramp-2 cDNA appears to be truncated at the 5' end (FIG. 7).

Mapping of the end of the MNramp-1 transcript by S1 nuclease analysis identified an unspliced intron in the DNA sequence of the MNramp-1 cDNA clone (SEQ. ID NO:1). The 3' end of this intron maps upstream of the C at position 415 in SEQ. ID NO:1, thereby interrupting an open reading frame that is predicted to initiate at an AUG in an upstream exon (not present in SEQ. ID NO:1). The sequence of a longer MNramp-1 cDNA clone of 2.276 kb, isolated by screening the 70/Z mouse pre-B library using probes from the 5'-terminal end of the partial MNramp-1 clone (SEQ. ID NO:1) is presented as SEQ. ID NO:24. A protein of 548 amino acids is predicted to be encoded by this full length ramp-1 cDNA clone (SEQ. ID NO:24).

Comparison of the human and mouse predicted NRAMP protein sequences revealed a remarkable degree of conservation between the two polypeptides, with 88% identical residues and 93% overall sequence similarity. Substitutions were not randomly distributed along the length of the protein but were clustered within discrete predicted structural domains (FIG. 7). The extreme amino (residues 1–50, 66% identity) and carboxy terminal ends (residues 517–550, 74% identity) of the two proteins were the least conserved segments, and gaps of 3 residues (positions 20–22 of mouse sequence) and 1 residue (position 546 of human sequence) had to be introduced to optimize alignments in these segments. In addition, the predicted second (TM 3–4 segment, positions 218–240; 63% identity) and third extracytoplasmic loops (TM5–6 segment, positions 310–349; 67% identity) showed significant sequence divergence. The fifth putative intracytoplasmic loop located between TM 8–9 (positions 450–468, 61% identity) and the last predicted TM10 domain (positions 496–517, 67% identity) also contained a cluster of substitutions that were mainly conservative. The rest of the amino terminal third up to and including TM3 (residues 50 to 217) and the segment overlapping TM6 to TM8 (residues 340 to 462) were the most conserved portions (97% identical, 99% similar) (FIG. 2E, 2F). The mouse Nramp protein was predicted to encode two consensus signals (S/T-X-R/K) for phosphorylation by protein kinase C, one in the predicted intracytoplasmic loop between TM 4 and 5, and another one in the extreme C-terminal domain (Vidal et al., 1993, Cell 73:469–485). These two predicted sites were not conserved in the human protein, instead a new one was found within the N-terminal region (position 54, FIG. 1A). By contrast, both proteins have retained the two predicted N-linked glycosylation sites within the third predicted extracellular loop (TM 5–6 interval). As expected, the "binding protein dependent transport system inner membrane component signature" was highly conserved in human NRAMP, including a conservative arginine to lysine substitution at the last position (position 392) of the motif. The highly hydrophobic predicted membrane associated domains of the proteins were strikingly conserved in the two species. Predicted TM 1–8 were identical in sequence (except for a single isoleucine to valine conservative substitution in TM 6), including four charged amino acids in TM 1, 2, 3 and 7. This suggests that these TM domains and residues play key structural and functional roles in this protein, and also suggests that non-conservative substitutions are not tolerated in these regions to retain function. This extremely high degree of conservation in the transmembrane domains is somewhat surprising since conservative substitution of hydrophobic amino acids are usually tolerated in TM domains without alteration or loss of function between homologs of the same proteins. This is of particular interest since the only amino acid sequence variation detected in Nramp between inbred mouse strains of opposite genotypes at Bcg is a single non-conservative glycine to aspartic acid substitution within predicted TM2 identified in innately susceptible (Bcg$^s$) strains. The observation that this TM domain in general, and glycine in particular are precisely conserved in human and mouse, strongly argues that this domain is important for function, and that non-conservative substitution in this region are likely to affect the function of this putative transporter.

The Nramp-2 mRNA transcripts were found to be ubiquitously expressed in all tissues tested. The level of Nramp-2 expression was fairly low and its detection by Northern blotting required the use poly A+RNA. This is in sharp contrast to the Nramp-1 gene which was found to be expressed in a tissue specific fashion in reticuloendothelial organs, in general, and mature tissue macrophages, in particular.

The high degree of sequence similarity between Nramp-1 and Nramp-2 strongly suggests an underlying functional homology. Both types of proteins could act on the same type of substrates but in different tissues.

Now isolated, the Nramp DNAs can be used in a variety of ways. For example, Nramp can be inserted in an expression vector. Such vectors contain all necessary regulatory signals to promote the expression of a DNA segment of interest. Expression vectors are typically either prokaryote specific, or eukaryote specific. However, vectors have been developed which can promote the expression of a DNA sequence of interest in either a prokaryotic or eukaryotic system. Such vectors are known as shuttle vectors.

The methods of subcloning cDNA inserts into vectors is well-known in the art (Sambrook et al. 1989, Molecular Cloning, A Laboratory Manual, Second Edition, Cold Spring Harbor Laboratory Press). Bluescript II KS(+) or M13mp18, mentioned above are two examples of prokaryotic vectors. Once having inserted the Nramp sequences or parts thereof, they can be transformed into a bacterial host according to well-known methods Sambrook et al. 1989, Molecular Cloning, A Laboratory Manual, Second Edition, Cold Spring Harbor Laboratory Press). An example of a prokaryotic expression vector is plasmid pT7-5 (lacY) which has been shown to functionally express the mouse multidrug resistance protein (Bibi et al., 1993, Proc. Natl. Acad. Sci. 90:9209–9213) an example of an expression vector for mammalian cells is vector pMT2 described in Wong et al., 1996, (Science 228:810–814).

Prokaryotic expression vectors are useful for the preparation of large quantities (up to milligram quantities) of the protein encoded by a DNA sequence of interest. This protein, or immunogenic peptide portions of same, can be used for example as a source of highly pure immunogen for the generation of specific antibodies. Alternatively, these proteins may be useful for therapeutic applications. The eukaryotic expression vectors are useful for expressing the DNA sequence of interest, or part thereof and can permit sophisticated analysis of the functional regions of the protein encoded therefrom. For example, Nramp having previously been mutagenised in vitro, could be introduced in macrophage cells, by well-known methods, and these macrophages could be challenged with infectious agents in order to assess the resistance/sensitivity phenotype.

The expression vectors mentioned above all contain an EcoRI site for the cloning of the insert to be expressed. Other methods of engineering of the particular insert to be inserted into the expression vector mentioned or other well-known expression vectors, are well known in the art. It should be understood that other types of vectors for specific functions could also be used, such as vectors designed for gene replacement. Thus, a number of additional elements could be present within the vectors, that would confer to same additional properties, like selection methods or designed at ensuring expression of the inserted nucleic acid.

The present invention will be more readily apparent by referring to the following examples which are given to illustrate the invention rather than to limit its scope.

EXAMPLE 1

Diagnostic Test to Identify Bcg$^r$ and Bcg$^s$ Mouse Strains

Inbred mouse strains A/J, AKR/J, BUB/BnJ, CBA/J, C3H/HeJ, C57BR/cdJ, C57L/J, C58/J, DBA/2J, L129/J, LP/J, Mus spretus, NOD/Lt, NZB/BINJ, P,J, PL/J, RIIIS/J, RF/J, SJL/J, SWR/J (all Bcg$^r$), BALB/cJ, C57BL/6J, C57BL/10J, CE/J, DBA/1J and NZW/LacJ were purchased from the Jackson Laboratory (Bar Harbor, Me.), and SWV mice were kindly provided by Dr. F. Biddle (University of Calgary, Calgary, Alberta). Total spleen RNA from A/J, AKR/J, BUB/BnJ, CBA/J, C3H/HeJ, C57BR/cdJ, C57L/J, C58/J, DBA/2J, L129/J, LP/J, Mus spretus, NOD/Lt, NZB/BINJ, P/J, PL/J, RIIIS/J, RF/J, SJL/J, SWR/J (all Bcg$^r$), BALB/cJ, C57BL/6J, C57BL/10J, CE/J, DBA/1J, NZW/LacJ and SWV (all Bcg$^s$) mouse strains was extracted and used to isolate strain-specific cDNA clones for Nramp. First-strand cDNA synthesis was carried out using 2 μg of total RNA, 100 ng of random hexamers, and 200 U of Moloney murine leukemia virus reverse transcriptase (Bethesda Research Laboratories). The primer-RNA mixture was first incubated for 5 min at 65° C., followed by addition of enzyme and further incubation at 37° C. for 90 min. The reaction conditions for cDNA synthesis were as previously described by (Epstein et al., 1991, Cell 67: 767–774). Nramp cDNA clones were obtained by PCR amplification of two contiguous fragments, A (787 bp) and B (857 bp), overlapping the entire coding region of the mRNA, using sequence-specific oligonucleotide primers 5'-TACATTCAGCCTGAGGAAGC-3'; SEQ ID NO:15 (positions 421–440 in FIG. 4) and 5'-TTGCTGGTAGAAGGCCTGAC-3' SEQ ID NO:16 (positions 1207–1198 in FIG. 4) for fragment A, and primers 5'-CTCTTCGTCATGGCTG-3' SEQ ID NO:17 (positions 1166–1181 in FIG. 4) and 5'-CGAGGTAAAGCACTTGTC-3' SEQ ID NO:18 (positions 2037–2020 in FIG. 4) for fragment B. Parameters for PCR amplification were 1 min at 94° C., 1 min at 60° C., and 2 min at 72° C. for 30 cycles, followed by a final extension period of 10 min at 72° C., under experimental conditions suggested by the supplier of Taq polymerase (BIOCAN). Amplified products were gel purified and cloned directly into a dT-tailed (Marchuk et al., 1991, Nucl. Acids Res. 19: 1154) pBluescript II KS(+) vector (Stratagene), and at least three independent clones for each fragment and each mouse strain were sequenced. As shown in FIG. 6, sequence analysis of the Nramp mRNA transcripts from 27 Bcg$^r$ and Bcg$^s$ mouse strains identified a G to A transition at nucleotide 783 in all susceptible strains, and translating in a Glycine to Aspartate mutation.

EXAMPLE 2

Strain Variations in Macrophage Activation for Tumor Toxicity (Bcg Gene Effects)

A peritoneal cell suspension was obtained from C. parvum-treated BALB/c (Bcg$^s$) or BALB/c.CD2 (Bcg$^r$) mice strains according to (Kaplan, 1981, In: Methods for studying Mononuclear Phagocytes, Acad. Press, pp775–783; Meltzer, ibid, pp785–791). The macrophages present in that suspension (8×10⁵ macrophages/0.5 ml) were allowed to adhere to bottoms of 16-mm culture wells and incubated with 5×10⁴ ³H-TdR-labeled 1023 fibrosarcoma target cells (Meltzer et al., 1975, JNCI 54: 1171–1184) for 18 hours. Labeled tumor cell monolayers, digested with 0.5% SDS in water were used to estimate total incorporated counts. Cytotoxicity was estimated by measuring release to the medium of incorporated ³H-TdR for prelabeled tumor cells in triplicate cultures and was expressed as percentage of total SDS counts. As shown in Table 2, the tumoricidal activity of the macrophages from the BALB/c.CD2 (Bcg$^r$) donor mouse is more than two (2) fold higher than that from the BALB/c (Bcg$^s$) mouse. The difference in macrophage tumor cytotoxicity between BALB/c and BALB/c.CD2 groups is statistically significant at p<0.01.

TABLE 2

Influence of Bcg on macrophage activation for tumor cytotoxicity

| Donor of Macrophages | Tumoricidal Activity (% total counts) |
|---|---|
| BALB/c (Bcg$^s$) | 31 ± 4 |
| BALB/c.CD2 (Bcg$^r$) | 63 ± 5 |
| Medium | 11 ± 2 |

EXAMPLE 3

Partial Sequence Analysis of Nramp from Distantly Related Species

To substantiate the importance of the predicted TM2 segment in Nramp-1 in which residue 105 is located, the portion of the Nramp transcript encoding the predicted TM2 from Nramp DNA or cDNA clones of rat (strains ACI, BB, Buffalo and BN), human (nine individuals) and chicken (strain C, W, 15I, N, 6$_1$ and 7$_2$) origins were cloned and sequenced. To isolate these clones, different methods were used. The rat clone for example was isolated using a mouse Nramp-1 probe selected from a well conserved region. The probe was used to screen a rat cDNA library under low stringency hybridization conditions as exemplified by the "Zoo blot" hybridization conditions mentioned above. The rabbit Nramp sequence was isolated using selected oligos and using standard RT-PCR conditions at low stringency ("PCR Protocols-A Guide to methods and applications", 1990, M. A. Innis et al., Eds., Acad. Press, Ca) to facilitate oligonucleotide annealing. Other well-known methods to isolate cDNAs or fragment thereof could be used. To obtain a full length clone, the fragment of Nramp isolated for example by low stringency hybridization, could be used at high stringency in an intra-species hybridization experiment.

As shown in FIG. 8, the sequence of TMT2 is well conserved in the four species analyzed. In fact, only two amino acid variations are detected in this domain between the chicken protein and that from the other species, a Val to Thr substitution at position 111 and a Phe to Leu substitution at position 114. These results suggest that TM2 plays an important functional role and that substitutions in codon 105 have not been tolerated during evolution in order to preserve function. Based on the conservation of the TM2 domains between distantly related animal species, and the absolute correlation between the Bcg$^r$ phenotype and the presence of Gly at position 105 in mouse Nramp1, the TM2 domain appears as a good target to identify genetic differences between animals which are resistant/susceptible to antigenically unrelated intracellular parasites, and more specifically, to identify in the human population genetic differences correlating with the susceptibility to tuberculosis and other intracellular macrophage infections such as leprosy, typhoid fever and Kala Azar.

EXAMPLE 4

Identification of Polymorphism and Sequence Variants in the Human Natural Resistant-associated Macrophage Protein (NRAMP) Gene Several methods were used to search for mutation in the Nramp-1 gene in genomic DNA of a panel of individuals which included nine members of an extended aboriginal Canadian families and twenty-four individuals from 11 Hong-Kong families. DNA samples were obtained from EBV-transformed cell lines of nine unrelated native Canadians who are members of an extended multiplex tuberculosis family, twenty-four unrelated individuals from eleven Chinese tuberculosis families, and from white blood cells of sixty unrelated Caucasian and twenty unrelated Oriental individuals. High molecular weight genomic DNA was extracted from EBV-transformed cells and white blood cells according to standard protocols Sambrook et al. (1989, Molecular Cloning: Laboratory Manual, Second Edition, Coldspring Harbor Laboratory Press), quantified by standard UV spectroscopy, and stored at 4° C. in te(pH8).

Polymorphisms have been identified within and around the human Nramp-1 gene. For example, southern blot analysis of an ApI restriction fragment length polymorphism (RFLP) was detected (allele1=5 kb, allele2=4 kb+1 kb) by using a Nramp cDNA probe. Sequencial hybridization using Nramp exon probes to DNA from individuals heterozygous for the RFLP and direct sequencing identified the polymorphism.

For southern analysis, 5 μg of genomic or 1 μg of cosmid DNA were digested with restriction enzymes using conditions and quantities recommended by the supplier (New England BioLabs). The digested DNA samples were size separated on agarose gels, transferred onto Hybond™ nylon membranes (Amersham), and hybridized with probes labelled to high specific activity (5×10⁸ cpm/pg of DNA) with α-³²P-dATP (Amersham, specific activity>3,000 Ci/mmol) under high stringency conditions. All Nramp derived probes were preannealed with 400 μg of human placental DNA in 1 ml hybridization medium for 1 hour at 65° C.

The identification of such a polymorphism can serve as the basis for the study of the association of defect in Nramp and susceptibility/resistance of individuals to tuberculosis. Furthermore, the polymorphism can be cloned by screening a genomic human library using well-known, subcloning and screening procedures. The desired clone can be followed with the ApaI- RFLP using standard conditions. Once obtained, this genomic clone can be used to obtain subclones and sequence the DNA around the Apa-1 site. Sequencing is performed by routine methods, and permits the identification of the site of the RFLP, within the coding region or within intron sequences. The sequences flanking the RFLP, can be used to derive oligonucleotide primers for PCR analysis of human DNA, and/or, if the RFLP is shown to be present within the coding region, RT-PCR can be used with oligo-nucleotide derived from the sequencing analysis. It follows that the sequencing analysis can also identify the molecular basis for the RFLP. Other methods such as single strand conformation analysis (SSCA) can be used in order to analyse whether the sequence variants are associated with human susceptibility to tuberculosis, leprosy, typhoid fever, and Kala Azar.

While the invention has been described with particular reference to the illustrated embodiment, it will be understood that numerous modifications thereto will appear to those skilled in the art. Accordingly, the above description and accompanying drawings should be taken as illustrative of the invention and not in a limiting sense.

What is claimed is:

1. A method of screening for compounds that regulate the level of Nramp, wherein Nramp is a transmembrane protein which participates in substrate translocation across a cellular membrane, and wherein Nramp confers resistance to infection to unrelated intracellular parasites, wherein said method comprises expressing a nucleic acid sequence encoding Nramp in a eukaryotic or prokaryotic host cell, and monitoring changes in Nramp level upon treatment with said compound, wherein said Nramp comprises an amino acid sequence selected from the group consisting of:
a) SEQ ID NO:2;
b) SEQ ID NO:4;
c) SEQ ID NO:6;
d) SEQ ID NO:25;
e) SEQ ID NO:27;
f) SEQ ID NO:28;
g) SEQ ID NO:30;
h) SEQ ID NO:32;
i) SEQ ID NO:33; and
j) an amino acid sequence which is at least 93% homologous to one of the amino acid sequences in a) to i);

and wherein a compound that regulates Nramp level is identified when said Nramp level is measurably different in the presence of said compound as compared to in the absence thereof.

2. The method of claim 1, wherein Nramp consists of an amino acid sequence selected from the group consisting of
a) SEQ ID NO:2;
b) SEQ ID NO:4;
c) SEQ ID NO:6;
d) SEQ ID NO:25;
e) SEQ ID NO:27;
f) SEQ ID NO:28;
g) SEQ ID NO:30;
h) SEQ ID NO:32;
i) SEQ ID NO:33; and
j) an amino acid sequence which is at least 93% homologous to one of the amino acid sequences in a) to i).

3. A method of screening for compounds that regulate the level of Nramp, wherein Nramp is a transmembrane protein which participates in substrate translocation across a cellular membrane, and wherein Nramp confers resistance to infection to unrelated intracellular parasites, wherein said method comprises expressing a polynucleotide sequence encoding Nramp in a eukaryotic or prokaryotic host cell, and monitoring changes in Nramp level upon treatment with said compound,
wherein said polynucleotide comprises a nucleotide sequence selected from the group consisting of:
a) SEQ ID NO:1;
b) SEQ ID NO:3;
c) SEQ ID NO:5;
d) SEQ ID NO:24;
e) SEQ ID NO:26;
f) SEQ ID NO:29;
g) SEQ ID NO:31;
h) a polynucleotide sequence which hybridizes under high stringency conditions to any of the polynucleotide sequences in (a) to (h);

wherein a compound that regulates Nramp level is identified when said Nramp level is measurably different in the presence of said compound as compared to in the absence thereof.

4. The method of claim 3, wherein said polynucleotide consists of a nucleotide sequence selected from the group consisting of:
a) SEQ ID NO:1;
b) SEQ ID NO:3;
c) SEQ ID NO:5;
d) SEQ ID NO:24;
e) SEQ ID NO:26;
f) SEQ ID NO:29;
g) SEQ ID NO:31;
h) a polynucleotide sequence encoding an amino acid sequence which is at least 93% homologous to an amino acid sequence encoded by any of the polynucleotide sequences in (a) to (g); and
i) a polynucleotide sequence which hybridizes under high stringency conditions to any of the polynucleotide sequences in (a) to (h).

5. A method of screening for compounds that regulate the level of Nramp, wherein Nramp is a transmembrane protein which participates in substrate translocation across a cellular membrane, and wherein Nramp confers resistance to infection to unrelated intracellular parasites, wherein said method comprises expressing a nucleic acid sequence comprising a polynucleotide sequence encoding a Nramp amino acid sequence in a eukaryotic or prokaryotic host cell, and monitoring changes in Nramp function or level upon treatment with said compound, wherein said Nramp amino acid sequence is selected from the group consisting of:
a) SEQ ID NO:2;
b) SEQ ID NO:4;
c) SEQ ID NO:6;
d) SEQ ID NO:25;
e) SEQ ID NO:27;
f) SEQ ID NO:28;
g) SEQ ID NO:30;
h) SEQ ID NO:32;
i) SEQ ID NO:33; and
j) an amino acid sequence which is at least 93% homologous to one of the amino acid sequences in a) to i);

wherein a compound that regulates Nramp level is identified when said Nramp level is measurably different in the presence of said compound as compared to in the absence thereof.

6. The method of claim 5, wherein said nucleotide sequence consists of a polynucleotide sequence encoding a Nramp amino acid sequence selected from the group consisting of:
a) SEQ ID NO:2;
b) SEQ ID NO:4;
c) SEQ ID NO:6;
d) SEQ ID NO:25;
e) SEQ ID NO:27;
f) SEQ ID NO:28;
g) SEQ ID NO:30;
h) SEQ ID NO:32;
i) SEQ ID NO:33; and
j) an amino acid sequence which is at least 93% homologous to one of the amino acid sequences in a) to i).

7. The method of claim 1, wherein said expressing is carried out with an expression vector that comprises a promoter element that is effective in initiating transcription of said nucleic acid sequence in said host cell.

8. The method of claim 7, wherein said host cell is a recombinant host cell.

9. The method of claim 8, wherein said host cell is a prokaryotic cell.

10. The method of claim 1, wherein said nucleic acid sequence is obtained from a mammalian cell.

11. The method of claim 1, wherein said amino acid sequence sequence is at least 97% identical at the amino acid level to any one of the amino acid sequences in (a) to (i).

12. The method of claim 11, wherein said amino acid sequence sequence is at least 99% similar at the amino acid level to any one of the amino acid sequences in (a) to (i).

13. The method of claim 1, wherein a mutant of SEQ ID NO:2 that comprises an aspartate in place of a glycine at position 105, is used as a control for a reduced function of Nramp.

14. The method of claim 1, wherein said nucleic acid sequence encodes SEQ ID NO:27.

15. The method of claim 1, wherein said nucleic acid sequence encodes SEQ ID NO:28.

16. The method of claim 1, wherein said nucleic acid sequence encodes SEQ ID NO:32.

17. The method of claim 1, wherein said nucleic acid sequence encodes SEQ ID NO:33.

18. A method of screening for compounds that regulate the level of Nramp, wherein Nramp is a transmembrane protein which participates in substrate translocation across a cellular membrane,
wherein said method comprises expressing a nucleic acid sequence encoding Nramp in a eukaryotic or prokaryotic host cell, and monitoring changes in Nramp level upon treatment with the compound, wherein Nramp comprises an amino acid sequence selected from the group consisting of:
a) SEQ ID NO:2;
b) SEQ ID NO:4;
c) SEQ ID NO:6;
d) SEQ ID NO:25;
e) SEQ ID NO:27;
f) SEQ ID NO:28;
g) SEQ ID NO:30;
h) SEQ ID NO:32; and
i) SEQ ID NO:33;
and wherein a compound that regulates Nramp level is identified when the Nramp level is measurably different in the presence of the compound as compared to in the absence thereof.

19. A method of screening for compounds that regulate the level of Nramp, wherein Nramp is a transmembrane protein which participates in substrate translocation across a cellular membrane,
wherein said method comprises expressing a polynucleotide sequence encoding Nramp in a eukaryotic or prokaryotic host cell, and monitoring changes in Nramp level upon treatment with said compound,
wherein said polynucleotide comprises a nucleotide sequence selected from the group consisting of:
a) SEQ ID NO:1;
b) SEQ ID NO:3;
c) SEQ ID NO:5;
d) SEQ ID NO:24;
e) SEQ ID NO:26;
f) SEQ ID NO:29; and
g) SEQ ID NO:31;
wherein a compound that regulates Nramp level is identified when the Nramp level is measurably different in the presence of said compound as compared to in the absence thereof.

20. A method of screening for compounds that regulate the level of Nramp, wherein Nramp is a transmembrane protein which participates in substrate translocation across a cellular membrane,
wherein said method comprises expressing a nucleic acid sequence comprising a polynucleotide sequence encoding a Nramp amino acid sequence in a eukaryotic or prokaryotic host cell, and monitoring changes in Nramp function or level upon treatment with the compound, wherein the Nramp amino acid sequence is selected from the group consisting of:
a) SEQ ID NO:2;
b) SEQ ID NO:4;
c) SEQ ID NO:6;
d) SEQ ID NO:25;
e) SEQ ID NO:27;
f) SEQ ID NO:28;
g) SEQ ID NO:30;
h) SEQ ID NO:32; and
i) SEQ ID NO:33;
wherein a compound that regulates Nramp level is identified when said Nramp level is measurably different in the presence of the compound as compared to in the absence thereof.

21. A method of screening for compounds that regulate the level of Nramp, wherein Nramp is a transmembrane protein which participates in substrate translocation across a cellular membrane,
wherein said method comprises expressing a nucleic acid sequence comprising a polynucleotide sequence encoding a Nramp amino acid sequence in a eukaryotic or prokaryotic host cell, and monitoring changes in Nramp function or level upon treatment with said compound, wherein said Nramp amino acid sequence is selected from the group consisting of:
a) SEQ ID NO:2;
b) SEQ ID NO:4;
c) SEQ ID NO:6;
d) SEQ ID NO:25;
e) SEQ ID NO:27;
f) SEQ ID NO:28;
g) SEQ ID NO:30;
h) SEQ ID NO:32; and
i) SEQ ID NO:33;
wherein a compound that regulates Nramp level is identified when the Nramp level is measurably different in the presence of said compound as compared to in the absence thereof.

* * * * *

SEQUENCE LISTING

<160> NUMBER OF SEQ ID NOS: 33

<210> SEQ ID NO 1
<211> LENGTH: 2485
<212> TYPE: DNA
<213> ORGANISM: Mus musculus
<220> FEATURE:
<221> NAME/KEY: CDS
<222> LOCATION: (469)..(1923)
<223> OTHER INFORMATION: Clone: MNramp-1

<400> SEQUENCE: 1

```
gtcgggccaa accctgaaat agagttgagt gactgagacc tcagtggtcc ccagagagaa      60
gagcctgaag tatgagaagg gtctgggag ggaagagctg taacagggag gtttaattac     120
aacaaggtcc ccctcttggg actctgagaa gcctgaaaga ggcagacagg tcatgtgctg     180
gccagctgca gaggctgctg ctgaacagga ccaacccaga aagcagagcc atagtgactc     240
agcaaatggc cctggtccct cggggacgg gcagcggtgg cattgggtgg gtgatggagg     300
acagggctgg ccagcctgac tgaagaagat acctgctgag tttttagctg aggggatggt     360
caaggccagc tgcatccatc caggagctaa catgacccga tctgcttgca cccccagggt     420
acattcagcc tgaggaagct gtgggcgttc acggggcctg gtttcctc atg agc atc      477
                                                      Met Ser Ile
                                                        1
```

```
gct ttc ctt gac ccg gga aac att gag tcc gac ctt caa gct ggc gct      525
Ala Phe Leu Asp Pro Gly Asn Ile Glu Ser Asp Leu Gln Ala Gly Ala
      5                   10                  15 gtg gct ggg ttc aaa ctc ctc tgg gtg ctg ctc tgg gcg act gtg cta      573
Val Ala Gly Phe Lys Leu Leu Trp Val Leu Leu Trp Ala Thr Val Leu
 20                  25                  30                  35 ggt ttg ctg tgc cag cgg ctg gct gcc cgg ctg ggc gtg gtg aca ggc      621
Gly Leu Leu Cys Gln Arg Leu Ala Ala Arg Leu Gly Val Val Thr Gly
                 40                  45                  50 aag gac ttg ggt gaa gtc tgc cat ctc tac tac ccc aag gtg ccc cgc      669
Lys Asp Leu Gly Glu Val Cys His Leu Tyr Tyr Pro Lys Val Pro Arg
             55                  60                  65 atc ctc ctc tgg ctg acc att gag ctg gcc att gtg ggc tca gat atg      717
Ile Leu Leu Trp Leu Thr Ile Glu Leu Ala Ile Val Gly Ser Asp Met
         70                  75                  80 cag gaa gtc atc ggg acg gct atc tcc ttc aat ctg ctc tcc gct gga      765
Gln Glu Val Ile Gly Thr Ala Ile Ser Phe Asn Leu Leu Ser Ala Gly
     85                  90                  95 cgc atc ccg ctg tgg ggc ggt gta ctg atc acc att gtg gac acc ttc      813
Arg Ile Pro Leu Trp Gly Gly Val Leu Ile Thr Ile Val Asp Thr Phe
100                 105                 110                 115 ttc ttc ctc ttc ttg gat aac tat ggt ttg cgc aag ctg gaa gct ttc      861
Phe Phe Leu Phe Leu Asp Asn Tyr Gly Leu Arg Lys Leu Glu Ala Phe
                120                 125                 130 ttc ggt ctc ctc att acc ata atg gct ttg acc ttc ggc tat gag tat      909
Phe Gly Leu Leu Ile Thr Ile Met Ala Leu Thr Phe Gly Tyr Glu Tyr
            135                 140                 145
```

-continued

| | | |
|---|---|---|
| gtg gta gca cac cct tcc cag gga gcg ctc ctt aag ggc ctg gtg ctg<br>Val Val Ala His Pro Ser Gln Gly Ala Leu Leu Lys Gly Leu Val Leu<br>                150                       155                     160 | 957 |
| ccc acc tgt ccg ggc tgt ggg cag ccc gag ctg ctg cag gca gtg ggc<br>Pro Thr Cys Pro Gly Cys Gly Gln Pro Glu Leu Leu Gln Ala Val Gly<br>   165                     170                       175 | 1005 |
| atc gtc ggt gcc atc atc atg ccc cat aac atc tac ctg cac tca gcc<br>Ile Val Gly Ala Ile Ile Met Pro His Asn Ile Tyr Leu His Ser Ala<br>180                     185                     190                  195 | 1053 |
| ttg gtc aag tct aga gaa gta gac aga acc cgc cgg gtg gat gtt cga<br>Leu Val Lys Ser Arg Glu Val Asp Arg Thr Arg Arg Val Asp Val Arg<br>                200                     205                     210 | 1101 |
| gaa gcc aac atg tac ttc ctg att gag gcc acc atc gcc cta tcg gtg<br>Glu Ala Asn Met Tyr Phe Leu Ile Glu Ala Thr Ile Ala Leu Ser Val<br>            215                     220                     225 | 1149 |
| tcc ttc atc atc aac ctc ttc gtc atg gct gtt ttt ggt cag gcc ttc<br>Ser Phe Ile Ile Asn Leu Phe Val Met Ala Val Phe Gly Gln Ala Phe<br>       230                     235                     240 | 1197 |
| tac cag caa acc aat gag gaa gcg ttc aac atc tgt gcc aac agc agc<br>Tyr Gln Gln Thr Asn Glu Glu Ala Phe Asn Ile Cys Ala Asn Ser Ser<br>      245                     250                     255 | 1245 |
| ctc cag aac tat gct aag atc ttc ccc agg gac aat aac act gtg tca<br>Leu Gln Asn Tyr Ala Lys Ile Phe Pro Arg Asp Asn Asn Thr Val Ser<br>260                     265                     270                  275 | 1293 |
| gtg gat att tat caa gga ggt gtg atc cta ggc tgt ctc ttt ggc cct<br>Val Asp Ile Tyr Gln Gly Gly Val Ile Leu Gly Cys Leu Phe Gly Pro<br>                280                     285                     290 | 1341 |
| gcg gcc ctc tac atc tgg gca gta ggt ctc ctg gca gcg ggg cag agt<br>Ala Ala Leu Tyr Ile Trp Ala Val Gly Leu Leu Ala Ala Gly Gln Ser<br>            295                     300                     305 | 1389 |
| tct act atg acc ggc acc tat gca gga cag ttc gtg atg gag ggt ttc<br>Ser Thr Met Thr Gly Thr Tyr Ala Gly Gln Phe Val Met Glu Gly Phe<br>                310                     315                     320 | 1437 |
| ctt aag ctg cgg tgg tcc cgc ttc gct cgg gtc ctt ctc acg cgc tct<br>Leu Lys Leu Arg Trp Ser Arg Phe Ala Arg Val Leu Leu Thr Arg Ser<br>   325                     330                     335 | 1485 |
| tgc gcc atc ctg ccc act gtg ttg gtg gct gtc ttc cga gac ctg aag<br>Cys Ala Ile Leu Pro Thr Val Leu Val Ala Val Phe Arg Asp Leu Lys<br>340                     345                     350                  355 | 1533 |
| gac ctg tcc ggc ctc aac gat cta ctc aat gtt ctg cag agt cta ctg<br>Asp Leu Ser Gly Leu Asn Asp Leu Leu Asn Val Leu Gln Ser Leu Leu<br>                360                     365                     370 | 1581 |
| ctg ccc ttc gct gta ctg ccc att ttg act ttc acc agc atg cca gct<br>Leu Pro Phe Ala Val Leu Pro Ile Leu Thr Phe Thr Ser Met Pro Ala<br>            375                     380                     385 | 1629 |
| gtc atg cag gag ttt gcc aac ggc cgg atg agc aaa gcc atc act tcg<br>Val Met Gln Glu Phe Ala Asn Gly Arg Met Ser Lys Ala Ile Thr Ser<br>       390                     395                     400 | 1677 |
| tgc atc atg gcg cta gtc tgc gcc atc aac ctg tac ttt gtg atc agc<br>Cys Ile Met Ala Leu Val Cys Ala Ile Asn Leu Tyr Phe Val Ile Ser<br>405                     410                     415 | 1725 |
| tac ctg ccc agc ctc ccg cac cct gcc tac ttt ggc ctt gtg gct ctg<br>Tyr Leu Pro Ser Leu Pro His Pro Ala Tyr Phe Gly Leu Val Ala Leu<br>420                     425                     430                  435 | 1773 |
| ttc gca ata ggt tac ttg ggc ctg act gct tat ctg gcc tgg acc tgt<br>Phe Ala Ile Gly Tyr Leu Gly Leu Thr Ala Tyr Leu Ala Trp Thr Cys<br>                440                     445                     450 | 1821 |
| tgc atc gcc cac gga gcc acc ttc ctg acc cac agc tcc cac aag cac<br>Cys Ile Ala His Gly Ala Thr Phe Leu Thr His Ser Ser His Lys His<br>            455                     460                     465 | 1869 |

-continued

```
ttc tta tat ggg ctc cct aac gag gag cag gga ggc gtg cag ggt tcc      1917
Phe Leu Tyr Gly Leu Pro Asn Glu Glu Gln Gly Gly Val Gln Gly Ser
        470                 475                 480 ggg tga ccgcggcatc cagcaagcaa agaggcaaca gggcagacac agcagagcaa        1973
Gly
    485 ttggaggtcc cctactggct ttctggatta ccggtttcca gtttggacaa gtgctttacc    2033 tcggaataat gacaccattc ttatcaccac aacctaagag acttaaaaaa cacagtgcct    2093 ggggcgagag atggctcagg tgtgagaaca ctagccacca ccctttcaga agatggggat    2153 tcaattccca gcatcaacgt ggtggctttc aactgaaggt gactccagtt cccagaacac    2213 ctcaaacaga actgccacaa ctccattgtc tcactccagc tcgtggaaga tgaagggagg    2273 agtcctaaag agttctaggt cgggtctctg gagagacggc tcagctgtta agagcaccgg    2333 actgctcttc cagaggtcct gagttcaatt cccagcaacc acatggtggc tcacaaccat    2393 ccataatggg atccctcttc tggtgtgtct gaagacaaca acagtgtcct cacatatata    2453 aaataaataa atcttaaaaa aaaaaaaaaa aa                                  2485
```

<210> SEQ ID NO 2
<211> LENGTH: 484
<212> TYPE: PRT
<213> ORGANISM: Mus musculus

<400> SEQUENCE: 2

```
Met Ser Ile Ala Phe Leu Asp Pro Gly Asn Ile Glu Ser Asp Leu Gln
 1               5                  10                  15

Ala Gly Ala Val Ala Gly Phe Lys Leu Leu Trp Val Leu Leu Trp Ala
            20                  25                  30

Thr Val Leu Gly Leu Leu Cys Gln Arg Leu Ala Ala Arg Leu Gly Val
        35                  40                  45

Val Thr Gly Lys Asp Leu Gly Glu Val Cys His Leu Tyr Tyr Pro Lys
    50                  55                  60

Val Pro Arg Ile Leu Leu Trp Leu Thr Ile Glu Leu Ala Ile Val Gly
65                  70                  75                  80

Ser Asp Met Gln Glu Val Ile Gly Thr Ala Ile Ser Phe Asn Leu Leu
                85                  90                  95

Ser Ala Gly Arg Ile Pro Leu Trp Gly Gly Val Leu Ile Thr Ile Val
            100                 105                 110

Asp Thr Phe Phe Phe Leu Phe Leu Asp Asn Tyr Gly Leu Arg Lys Leu
        115                 120                 125

Glu Ala Phe Phe Gly Leu Leu Ile Thr Ile Met Ala Leu Thr Phe Gly
    130                 135                 140

Tyr Glu Tyr Val Val Ala His Pro Ser Gln Gly Ala Leu Leu Lys Gly
145                 150                 155                 160

Leu Val Leu Pro Thr Cys Pro Gly Cys Gly Gln Pro Glu Leu Leu Gln
                165                 170                 175

Ala Val Gly Ile Val Gly Ala Ile Ile Met Pro His Asn Ile Tyr Leu
            180                 185                 190

His Ser Ala Leu Val Lys Ser Arg Glu Val Asp Arg Thr Arg Arg Val
        195                 200                 205

Asp Val Arg Glu Ala Asn Met Tyr Phe Leu Ile Glu Ala Thr Ile Ala
    210                 215                 220

Leu Ser Val Ser Phe Ile Ile Asn Leu Phe Val Met Ala Val Phe Gly
225                 230                 235                 240
```

```
Gln Ala Phe Tyr Gln Gln Thr Asn Glu Glu Ala Phe Asn Ile Cys Ala
                245                 250                 255
Asn Ser Ser Leu Gln Asn Tyr Ala Lys Ile Phe Pro Arg Asp Asn Asn
                260                 265                 270
Thr Val Ser Val Asp Ile Tyr Gln Gly Val Ile Leu Gly Cys Leu
                275                 280                 285
Phe Gly Pro Ala Ala Leu Tyr Ile Trp Ala Val Gly Leu Leu Ala Ala
                290                 295                 300
Gly Gln Ser Ser Thr Met Thr Gly Thr Tyr Ala Gly Gln Phe Val Met
305                 310                 315                 320
Glu Gly Phe Leu Lys Leu Arg Trp Ser Arg Phe Ala Arg Val Leu Leu
                325                 330                 335
Thr Arg Ser Cys Ala Ile Leu Pro Thr Val Leu Val Ala Val Phe Arg
                340                 345                 350
Asp Leu Lys Asp Leu Ser Gly Leu Asn Asp Leu Leu Asn Val Leu Gln
                355                 360                 365
Ser Leu Leu Leu Pro Phe Ala Val Leu Pro Ile Leu Thr Phe Thr Ser
                370                 375                 380
Met Pro Ala Val Met Gln Glu Phe Ala Asn Gly Arg Met Ser Lys Ala
385                 390                 395                 400
Ile Thr Ser Cys Ile Met Ala Leu Val Cys Ala Ile Asn Leu Tyr Phe
                405                 410                 415
Val Ile Ser Tyr Leu Pro Ser Leu Pro His Pro Ala Tyr Phe Gly Leu
                420                 425                 430
Val Ala Leu Phe Ala Ile Gly Tyr Leu Gly Leu Thr Ala Tyr Leu Ala
                435                 440                 445
Trp Thr Cys Cys Ile Ala His Gly Ala Thr Phe Leu Thr His Ser Ser
                450                 455                 460
His Lys His Phe Leu Tyr Gly Leu Pro Asn Glu Glu Gln Gly Gly Val
465                 470                 475                 480
Gln Gly Ser Gly
```

<210> SEQ ID NO 3
<211> LENGTH: 2008
<212> TYPE: DNA
<213> ORGANISM: Homo sapiens
<220> FEATURE:
<221> NAME/KEY: CDS
<222> LOCATION: (278)..(1729)
<223> OTHER INFORMATION: Clone: HNramp-1

<400> SEQUENCE: 3

```
cggtctgggc acgggtgcag gctgaggagc tgcccagagc accgctcaca ctcccagagt    60
acctgaagtc ggcatttcaa tgacaggtga caagggtccc caaaggctaa gcgggtccag   120
ctatggttcc atctccagcc cgaccagccc gaccagccca gggccacagc aagcacctcc   180
cagagagacc tacctgagtg agaagatccc catcccagac acaaaccggg caccttcagc   240
ctgcgaacgt atgggccttc acggggctgg cttcctc atg agc att gct ttc ctg   295
                                         Met Ser Ile Ala Phe Leu
                                         1               5 gac cca gga aac atc gag tca gat ctt cag gct ggc gcc gtg gcg gga   343
Asp Pro Gly Asn Ile Glu Ser Asp Leu Gln Ala Gly Ala Val Ala Gly
            10                  15                  20 ttc aaa ctt ctc tgg gtg ctg ctc tgg gcc acc gtg ttg ggc ttg ctc   391
Phe Lys Leu Leu Trp Val Leu Leu Trp Ala Thr Val Leu Gly Leu Leu
        25                  30                  35
```

-continued

| | | |
|---|---|---|
| tgc cag cga ctg gct gca cgt ctg ggc gtg gtg aca ggc aag gac ttg<br>Cys Gln Arg Leu Ala Ala Arg Leu Gly Val Val Thr Gly Lys Asp Leu<br>40 45 50 | 439 | |
| ggc gag gtc tgc cat ctc tac tac ccc cag gtg ccc cgc acc gtc ctg<br>Gly Glu Val Cys His Leu Tyr Tyr Pro Gln Val Pro Arg Thr Val Leu<br>55 60 65 70 | 487 | |
| tgg ctg acc atc gag cta gcc att gtg ggc tcc gac atg cag gaa gtc<br>Trp Leu Thr Ile Glu Leu Ala Ile Val Gly Ser Asp Met Gln Glu Val<br>75 80 85 | 535 | |
| atc ggc acg gcc att gca ttc aat ctg ctc tca gct gga cga atc cca<br>Ile Gly Thr Ala Ile Ala Phe Asn Leu Leu Ser Ala Gly Arg Ile Pro<br>90 95 100 | 583 | |
| ctc tgg ggt ggc gtc ctc atc acc atc gtg gac acc ttc ttc ttc ctc<br>Leu Trp Gly Gly Val Leu Ile Thr Ile Val Asp Thr Phe Phe Phe Leu<br>105 110 115 | 631 | |
| ttc ctc gat aac tac ggg ctg cgg aag ctg gaa gct ttt ttt gga ctc<br>Phe Leu Asp Asn Tyr Gly Leu Arg Lys Leu Glu Ala Phe Phe Gly Leu<br>120 125 130 | 679 | |
| ctt ata acc att atg gcc ttg acc ttt ggc tat gag tat gtg gtg gcg<br>Leu Ile Thr Ile Met Ala Leu Thr Phe Gly Tyr Glu Tyr Val Val Ala<br>135 140 145 150 | 727 | |
| cgt cct gag cag gga gcg ctt ctt cgg ggc ctg ttc ctg ccc tcg tgc<br>Arg Pro Glu Gln Gly Ala Leu Leu Arg Gly Leu Phe Leu Pro Ser Cys<br>155 160 165 | 775 | |
| ccg ggc tgc ggc cac ccc gag ctg ctg cag gcg gtg ggc att gtt ggc<br>Pro Gly Cys Gly His Pro Glu Leu Leu Gln Ala Val Gly Ile Val Gly<br>170 175 180 | 823 | |
| gcc atc atc atg ccc cac aac atc tac ctg cac tcg gcc ctg gtc aag<br>Ala Ile Ile Met Pro His Asn Ile Tyr Leu His Ser Ala Leu Val Lys<br>185 190 195 | 871 | |
| tct cga gag ata gac cgg gcc cgc cga gcg gac atc aga gaa gcc aac<br>Ser Arg Glu Ile Asp Arg Ala Arg Arg Ala Asp Ile Arg Glu Ala Asn<br>200 205 210 | 919 | |
| atg tac ttc ctg att gag gcc acc atc gcc ctg tcc gtc tcc ttt atc<br>Met Tyr Phe Leu Ile Glu Ala Thr Ile Ala Leu Ser Val Ser Phe Ile<br>215 220 225 230 | 967 | |
| atc aac ctc ttt gtc atg gct gtc ttt ggg cag gcc ttc tac cag aaa<br>Ile Asn Leu Phe Val Met Ala Val Phe Gly Gln Ala Phe Tyr Gln Lys<br>235 240 245 | 1015 | |
| acc aac cag gct gcg ttc aac atc tgt gcc aac agc agc ctc cac gac<br>Thr Asn Gln Ala Ala Phe Asn Ile Cys Ala Asn Ser Ser Leu His Asp<br>250 255 260 | 1063 | |
| tac gcc aag atc ttc ccc atg aac aac gcc acc gtg gcc gtg gac att<br>Tyr Ala Lys Ile Phe Pro Met Asn Asn Ala Thr Val Ala Val Asp Ile<br>265 270 275 | 1111 | |
| tac cag ggg ggc gtg atc ctg ggc tgc ctg ttc ggc ccc gcg gcc ctc<br>Tyr Gln Gly Gly Val Ile Leu Gly Cys Leu Phe Gly Pro Ala Ala Leu<br>280 285 290 | 1159 | |
| tac atc tgg gcc ata ggt ctc ctg gcg gct ggg cag agc tcc acc atg<br>Tyr Ile Trp Ala Ile Gly Leu Leu Ala Ala Gly Gln Ser Ser Thr Met<br>295 300 305 310 | 1207 | |
| acg ggc acc tac gcg gga cag ttc gtg atg gag ggc ttc ctg agg ctg<br>Thr Gly Thr Tyr Ala Gly Gln Phe Val Met Glu Gly Phe Leu Arg Leu<br>315 320 325 | 1255 | |
| cgg tgg tca cgc ttc gcc cgt gtc ctc ctc acc cgc tcc tgc acc atc<br>Arg Trp Ser Arg Phe Ala Arg Val Leu Leu Thr Arg Ser Cys Thr Ile<br>330 335 340 | 1303 | |
| ctg ccc acc gtg ctc gtg gct gtc ttc cgg gac ctg agg gac ttg tcg<br>Leu Pro Thr Val Leu Val Ala Val Phe Arg Asp Leu Arg Asp Leu Ser | 1351 | |

-continued

```
                345                 350                 355
ggc ctc aat gat cta ctc aac gtg ctg cag agc ctg ctg ctc ccg ttc      1399
Gly Leu Asn Asp Leu Leu Asn Val Leu Gln Ser Leu Leu Leu Pro Phe
        360                 365                 370 gcc gtg ctg ccc atc ctc acg ttc acc agc atg ccc acc ctc atg cag      1447
Ala Val Leu Pro Ile Leu Thr Phe Thr Ser Met Pro Thr Leu Met Gln
375                 380                 385                 390 gag ttt gcc aat ggc ctg ctg aac aag gtc gtc acc tct tcc atc atg      1495
Glu Phe Ala Asn Gly Leu Leu Asn Lys Val Val Thr Ser Ser Ile Met
                395                 400                 405 gtg cta gtc tgc gcc atc aac ctc tac ttc gtg gtc agc tat ctg ccc      1543
Val Leu Val Cys Ala Ile Asn Leu Tyr Phe Val Val Ser Tyr Leu Pro
            410                 415                 420 agc ctg ccc cac cct gcc tac ttc ggc ctt gca gcc ttg ctg gcc gca      1591
Ser Leu Pro His Pro Ala Tyr Phe Gly Leu Ala Ala Leu Leu Ala Ala
        425                 430                 435 gcc tac ctg ggc ctc agc acc tac ctg gtc tgg acc tgt tgc ctt gcc      1639
Ala Tyr Leu Gly Leu Ser Thr Tyr Leu Val Trp Thr Cys Cys Leu Ala
    440                 445                 450 cac gga gcc acc ttt ctg gcc cac agc tcc cac cac cac ttc ctg tat      1687
His Gly Ala Thr Phe Leu Ala His Ser Ser His His His Phe Leu Tyr
455                 460                 465                 470 ggg ctc ctt gaa gag gac cag aaa ggg gag acc tct ggc tag              1729
Gly Leu Leu Glu Glu Asp Gln Lys Gly Glu Thr Ser Gly
                475                 480 gcccacacca gggcctggct gggagtggca tgtatgacgt gactggcctg ctggatgtgg    1789 aggggcgcg tgcaggcagc aggatagagt ggacagttcc tgagaccagc caacctgggg    1849
gctttaggga cctgctgttt cctagcgcag ccatgtgatt acctctgggt ctcagtgtcc    1909
tcatctgtaa aatggagaca ccaccaccct tgccatggag gttaagcact ttaacacagt    1969
gtctggcact tgggacaaaa acaaacaaac gaaaaaccg                           2008
```

<210> SEQ ID NO 4
<211> LENGTH: 483
<212> TYPE: PRT
<213> ORGANISM: Homo sapiens

<400> SEQUENCE: 4

```
Met Ser Ile Ala Phe Leu Asp Pro Gly Asn Ile Glu Ser Asp Leu Gln
1               5                   10                  15

Ala Gly Ala Val Ala Gly Phe Lys Leu Leu Trp Val Leu Leu Trp Ala
                20                  25                  30

Thr Val Leu Gly Leu Leu Cys Gln Arg Leu Ala Ala Arg Leu Gly Val
            35                  40                  45

Val Thr Gly Lys Asp Leu Gly Glu Val Cys His Leu Tyr Tyr Pro Gln
        50                  55                  60

Val Pro Arg Thr Val Leu Trp Leu Thr Ile Glu Leu Ala Ile Val Gly
65                  70                  75                  80

Ser Asp Met Gln Glu Val Ile Gly Thr Ala Ile Ala Phe Asn Leu Leu
                85                  90                  95

Ser Ala Gly Arg Ile Pro Leu Trp Gly Gly Val Leu Ile Thr Ile Val
                100                 105                 110

Asp Thr Phe Phe Phe Leu Phe Leu Asp Asn Tyr Gly Leu Arg Lys Leu
            115                 120                 125

Glu Ala Phe Phe Gly Leu Leu Ile Thr Ile Met Ala Leu Thr Phe Gly
        130                 135                 140
```

-continued

```
Tyr Glu Tyr Val Val Ala Arg Pro Glu Gln Gly Ala Leu Leu Arg Gly
145                 150                 155                 160

Leu Phe Leu Pro Ser Cys Pro Gly Cys Gly His Pro Glu Leu Leu Gln
                165                 170                 175

Ala Val Gly Ile Val Gly Ala Ile Ile Met Pro His Asn Ile Tyr Leu
            180                 185                 190

His Ser Ala Leu Val Lys Ser Arg Glu Ile Asp Arg Ala Arg Arg Ala
        195                 200                 205

Asp Ile Arg Glu Ala Asn Met Tyr Phe Leu Ile Glu Ala Thr Ile Ala
210                 215                 220

Leu Ser Val Ser Phe Ile Ile Asn Leu Phe Val Met Ala Val Phe Gly
225                 230                 235                 240

Gln Ala Phe Tyr Gln Lys Thr Asn Gln Ala Ala Phe Asn Ile Cys Ala
                245                 250                 255

Asn Ser Ser Leu His Asp Tyr Ala Lys Ile Phe Pro Met Asn Asn Ala
                260                 265                 270

Thr Val Ala Val Asp Ile Tyr Gln Gly Gly Val Ile Leu Gly Cys Leu
            275                 280                 285

Phe Gly Pro Ala Ala Leu Tyr Ile Trp Ala Ile Gly Leu Leu Ala Ala
290                 295                 300

Gly Gln Ser Ser Thr Met Thr Gly Thr Tyr Ala Gly Gln Phe Val Met
305                 310                 315                 320

Glu Gly Phe Leu Arg Leu Arg Trp Ser Arg Phe Ala Arg Val Leu Leu
                325                 330                 335

Thr Arg Ser Cys Thr Ile Leu Pro Thr Val Leu Val Ala Val Phe Arg
                340                 345                 350

Asp Leu Arg Asp Leu Ser Gly Leu Asn Asp Leu Leu Asn Val Leu Gln
            355                 360                 365

Ser Leu Leu Leu Pro Phe Ala Val Leu Pro Ile Leu Thr Phe Thr Ser
370                 375                 380

Met Pro Thr Leu Met Gln Glu Phe Ala Asn Gly Leu Leu Asn Lys Val
385                 390                 395                 400

Val Thr Ser Ser Ile Met Val Leu Val Cys Ala Ile Asn Leu Tyr Phe
                405                 410                 415

Val Val Ser Tyr Leu Pro Ser Leu Pro His Pro Ala Tyr Phe Gly Leu
            420                 425                 430

Ala Ala Leu Leu Ala Ala Ala Tyr Leu Gly Leu Ser Thr Tyr Leu Val
        435                 440                 445

Trp Thr Cys Cys Leu Ala His Gly Ala Thr Phe Leu Ala His Ser Ser
450                 455                 460

His His His Phe Leu Tyr Gly Leu Leu Glu Glu Asp Gln Lys Gly Glu
465                 470                 475                 480

Thr Ser Gly
```

<210> SEQ ID NO 5
<211> LENGTH: 1874
<212> TYPE: DNA
<213> ORGANISM: Homo sapiens
<220> FEATURE:
<221> NAME/KEY: CDS
<222> LOCATION: (76)..(1524)
<223> OTHER INFORMATION: Clone: HNramp-2

<400> SEQUENCE: 5
aattccggag gaatggagga gtactcttgt tttagctttc gtaaactctg ggctttcacc    60

```
ggaccaggtt ttctt atg acg att gcc tac ctg gat cca gga aat att gaa    111
             Met Thr Ile Ala Tyr Leu Asp Pro Gly Asn Ile Glu
               1               5                  10 tcc gat ttg cag tct gga gca gtg gct gga ttt aag ttg ctc tgg atc    159
Ser Asp Leu Gln Ser Gly Ala Val Ala Gly Phe Lys Leu Leu Trp Ile
         15                  20                  25 ctt ctg ttg gcc acc ctt gtg ggg ctg ctc cag cgg ctt gca gct        207
Leu Leu Leu Ala Thr Leu Val Gly Leu Leu Gln Arg Leu Ala Ala
     30                  35                  40 aag ctg gga gtg gtt act ggg ctg cat ctt gct gaa gta tgt cac cgt    255
Lys Leu Gly Val Val Thr Gly Leu His Leu Ala Glu Val Cys His Arg
 45                  50                  55                  60 cag tat ccc aag gtc cca cga gtc atc ctg tgg ctg atg gtg gag ttg    303
Gln Tyr Pro Lys Val Pro Arg Val Ile Leu Trp Leu Met Val Glu Leu
                 65                  70                  75 gct atc atc ggc tca gac atg caa gaa gtc att gga tca gcc att gct    351
Ala Ile Ile Gly Ser Asp Met Gln Glu Val Ile Gly Ser Ala Ile Ala
             80                  85                  90 atc aat ctt ctg tct gta gga aga att cct ctg tgg ggt ggc gtt ctc    399
Ile Asn Leu Leu Ser Val Gly Arg Ile Pro Leu Trp Gly Gly Val Leu
         95                  100                 105 atc acc att gca gat act ttt gta ttt ctc ttc ttg gac aaa tat ggc    447
Ile Thr Ile Ala Asp Thr Phe Val Phe Leu Phe Leu Asp Lys Tyr Gly
     110                 115                 120 ttg cgg aag cta gaa gca ttt ttt ggc ttt ctc atc act att atg gcc    495
Leu Arg Lys Leu Glu Ala Phe Phe Gly Phe Leu Ile Thr Ile Met Ala
125                 130                 135                 140 ctc aca ttt gga tat gag tat gtt aca gtg aaa ccc agc cag agc cag   543
Leu Thr Phe Gly Tyr Glu Tyr Val Thr Val Lys Pro Ser Gln Ser Gln
                 145                 150                 155 gta ctc aag ggc atg ttc gta cca tcc tgt tca ggc tgt cgc act cca    591
Val Leu Lys Gly Met Phe Val Pro Ser Cys Ser Gly Cys Arg Thr Pro
             160                 165                 170 cag att gaa cag gct gtg ggc atc gtg gga gct gtc atc atg cca cac    639
Gln Ile Glu Gln Ala Val Gly Ile Val Gly Ala Val Ile Met Pro His
         175                 180                 185 aac atg tac ctg cat tct gcc tta gtc aag tct aga cag gta aac cgg    687
Asn Met Tyr Leu His Ser Ala Leu Val Lys Ser Arg Gln Val Asn Arg
     190                 195                 200 aac aat aag cag gaa gtt cga gaa gcc aat aag tac ttc ttc att gaa    735
Asn Asn Lys Gln Glu Val Arg Glu Ala Asn Lys Tyr Phe Phe Ile Glu
205                 210                 215                 220 tcc tgc att gca ctc ttt gtt tcc ttc atc atc aat gtc ttt gtt gtc    783
Ser Cys Ile Ala Leu Phe Val Ser Phe Ile Ile Asn Val Phe Val Val
                 225                 230                 235 tca gtc ttt gct gaa gca ttt ttt ggg aaa acc aac gag cag gtg gtt    831
Ser Val Phe Ala Glu Ala Phe Phe Gly Lys Thr Asn Glu Gln Val Val
             240                 245                 250 gaa gtc tgt aca aat acc agc agt cct cat gct ggc ctc ttt cct aaa    879
Glu Val Cys Thr Asn Thr Ser Ser Pro His Ala Gly Leu Phe Pro Lys
         255                 260                 265 gat aac tcg aca ctg gct gtg gac atc tac aaa ggg ggt gtt gtg ctg    927
Asp Asn Ser Thr Leu Ala Val Asp Ile Tyr Lys Gly Gly Val Val Leu
     270                 275                 280 gga tgt tac ttt ggg cct gct gca ctc tac att tgg gca gtg ggg atc    975
Gly Cys Tyr Phe Gly Pro Ala Ala Leu Tyr Ile Trp Ala Val Gly Ile
285                 290                 295                 300 ctg gct gca gga cag agc tcc acc atg aca gga acc tat tct ggc cag    1023
Leu Ala Ala Gly Gln Ser Ser Thr Met Thr Gly Thr Tyr Ser Gly Gln
                 305                 310                 315
```

```
ttt gtc atg gag gga ttc ctg aac cta aag tgg tca cgc ttt gcc cga    1071
Phe Val Met Glu Gly Phe Leu Asn Leu Lys Trp Ser Arg Phe Ala Arg
            320                 325                 330 gtg gtt ctg act cgc tct atc gcc atc atc ccc act ctg ctt gtt gct    1119
Val Val Leu Thr Arg Ser Ile Ala Ile Ile Pro Thr Leu Leu Val Ala
        335                 340                 345 gtc ttc caa gat gta gag cat cta aca ggg atg aat gac ttt ctg aat    1167
Val Phe Gln Asp Val Glu His Leu Thr Gly Met Asn Asp Phe Leu Asn
    350                 355                 360 gtt cta cag agc tta cag ctt ccc ttt gct ctc ata ccc atc ctc aca    1215
Val Leu Gln Ser Leu Gln Leu Pro Phe Ala Leu Ile Pro Ile Leu Thr
365                 370                 375                 380 ttt acg tac gtg cgg cca gta atg agt gac ttt gcc aat gga cta ggc    1263
Phe Thr Tyr Val Arg Pro Val Met Ser Asp Phe Ala Asn Gly Leu Gly
            385                 390                 395 tgc cgg att gca gga gga atc ttg gtc ctt atc atc tgt tcc atc aat    1311
Cys Arg Ile Ala Gly Gly Ile Leu Val Leu Ile Ile Cys Ser Ile Asn
        400                 405                 410 atg tac ttt gta gtg gtt tat gtc cgg gac cta ggg cat gtg gca tta    1359
Met Tyr Phe Val Val Val Tyr Val Arg Asp Leu Gly His Val Ala Leu
    415                 420                 425 tat gtg gtg gct gct gtg gtc agc gtg gct tat ctg ggc ttt gtg ttc    1407
Tyr Val Val Ala Ala Val Val Ser Val Ala Tyr Leu Gly Phe Val Phe
430                 435                 440 tac ttg ggt tgg caa tgt ttg att gca ctg ggc atg tcc ttc ctg gac    1455
Tyr Leu Gly Trp Gln Cys Leu Ile Ala Leu Gly Met Ser Phe Leu Asp
445                 450                 455                 460 tgt ggg cat acg gta agc atc tct aaa ggc ctg ctg aca gaa gaa gcc    1503
Cys Gly His Thr Val Ser Ile Ser Lys Gly Leu Leu Thr Glu Glu Ala
            465                 470                 475 acc cgt ggc tac gtt aaa taa cactggatta gtctgtcttc tgcaggtagc       1554
Thr Arg Gly Tyr Val Lys
            480 catcagagcc agtgtgtttc tatggtttac tgtgtgaaca tagccaaaag tatgtgccgt   1614 tgcacagact gtgtttatga ctcaaccgtt ggttggaaaa gactttgttt catgtgtatt   1674 tgaaagatgg aattattttt tccttcctga cctaacctta gaactggatt agggtgggat   1734 cttttgaaaag ctgacatttg ctgctatcat tccaacacta aattcttaag tagttgccca   1794 agggccagct cagtttatcc ttcggagaga caaggatatg catgattctt aaccaggcta   1854 tatgttaaaa aaaaaaaaa                                               1874

<210> SEQ ID NO 6
<211> LENGTH: 482
<212> TYPE: PRT
<213> ORGANISM: Homo sapiens

<400> SEQUENCE: 6

Met Thr Ile Ala Tyr Leu Asp Pro Gly Asn Ile Glu Ser Asp Leu Gln
 1               5                  10                  15

Ser Gly Ala Val Ala Gly Phe Lys Leu Leu Trp Ile Leu Leu Leu Ala
                20                  25                  30

Thr Leu Val Gly Leu Leu Gln Arg Leu Ala Ala Lys Leu Gly Val
            35                  40                  45

Val Thr Gly Leu His Leu Ala Glu Val Cys His Arg Gln Tyr Pro Lys
        50                  55                  60

Val Pro Arg Val Ile Leu Trp Leu Met Val Glu Leu Ala Ile Ile Gly
65                  70                  75                  80
```

```
Ser Asp Met Gln Glu Val Ile Gly Ser Ala Ile Ala Ile Asn Leu Leu
                85                  90                  95

Ser Val Gly Arg Ile Pro Leu Trp Gly Gly Val Leu Ile Thr Ile Ala
            100                 105                 110

Asp Thr Phe Val Phe Leu Phe Leu Asp Lys Tyr Gly Leu Arg Lys Leu
        115                 120                 125

Glu Ala Phe Phe Gly Phe Leu Ile Thr Ile Met Ala Leu Thr Phe Gly
    130                 135                 140

Tyr Glu Tyr Val Thr Val Lys Pro Ser Gln Ser Gln Val Leu Lys Gly
145                 150                 155                 160

Met Phe Val Pro Ser Cys Ser Gly Cys Arg Thr Pro Gln Ile Glu Gln
                165                 170                 175

Ala Val Gly Ile Val Gly Ala Val Ile Met Pro His Asn Met Tyr Leu
                180                 185                 190

His Ser Ala Leu Val Lys Ser Arg Gln Val Asn Arg Asn Lys Gln
                195                 200                 205

Glu Val Arg Glu Ala Asn Lys Tyr Phe Phe Ile Glu Ser Cys Ile Ala
            210                 215                 220

Leu Phe Val Ser Phe Ile Ile Asn Val Phe Val Ser Val Phe Ala
225                 230                 235                 240

Glu Ala Phe Phe Gly Lys Thr Asn Glu Gln Val Val Glu Val Cys Thr
                245                 250                 255

Asn Thr Ser Ser Pro His Ala Gly Leu Phe Pro Lys Asp Asn Ser Thr
                260                 265                 270

Leu Ala Val Asp Ile Tyr Lys Gly Gly Val Val Leu Gly Cys Tyr Phe
            275                 280                 285

Gly Pro Ala Ala Leu Tyr Ile Trp Ala Val Gly Ile Leu Ala Ala Gly
    290                 295                 300

Gln Ser Ser Thr Met Thr Gly Thr Tyr Ser Gly Gln Phe Val Met Glu
305                 310                 315                 320

Gly Phe Leu Asn Leu Lys Trp Ser Arg Phe Ala Arg Val Val Leu Thr
                325                 330                 335

Arg Ser Ile Ala Ile Ile Pro Thr Leu Leu Val Ala Val Phe Gln Asp
                340                 345                 350

Val Glu His Leu Thr Gly Met Asn Asp Phe Leu Asn Val Leu Gln Ser
            355                 360                 365

Leu Gln Leu Pro Phe Ala Leu Ile Pro Ile Leu Thr Phe Thr Tyr Val
    370                 375                 380

Arg Pro Val Met Ser Asp Phe Ala Asn Gly Leu Gly Cys Arg Ile Ala
385                 390                 395                 400

Gly Gly Ile Leu Val Leu Ile Ile Cys Ser Ile Asn Met Tyr Phe Val
                405                 410                 415

Val Val Tyr Val Arg Asp Leu Gly His Val Ala Leu Tyr Val Val Ala
                420                 425                 430

Ala Val Val Ser Val Ala Tyr Leu Gly Phe Val Phe Tyr Leu Gly Trp
            435                 440                 445

Gln Cys Leu Ile Ala Leu Gly Met Ser Phe Leu Asp Cys Gly His Thr
    450                 455                 460

Val Ser Ile Ser Lys Gly Leu Leu Thr Glu Glu Ala Thr Arg Gly Tyr
465                 470                 475                 480

Val Lys
```

```
<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 7
taggaggtta tgagcccgaa agtg                                          24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 8
ctcagggaga tcctctacag actt                                          24

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 9
tggtgccctg agcatagaga ctg                                           23

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 10
gtggtatttc gtggttgtca gccg                                          24

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 11
cccgtcgacc acctgaggag tgaattggtc g                                  31

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 12
gtgaactgca ctgtgacaag ctgc                                          24

<210> SEQ ID NO 13
```

```
<211> LENGTH: 30
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 13
cccgtcgacg tcgggtcccc tcgggattgg                                    30

<210> SEQ ID NO 14
<211> LENGTH: 31
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 14
cccggatccg cgacgaagac ctcctcaagg c                                  31

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 15
tacattcagc ctgaggaagc                                               20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 16
ttgctggtag aaggcctgac                                               20

<210> SEQ ID NO 17
<211> LENGTH: 16
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 17
ctcttcgtca tggctg                                                   16

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 18
cgaggtaaag cacttgtc                                                 18

<210> SEQ ID NO 19
<211> LENGTH: 33
```

```
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 19
cgcatcccgc tgtggggcgg tgtactgatc acc                          33

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 20
ccgggcacct tcagcctgcg                                         20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 21
gcccccaggt tggctggtct                                         20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 22
aggagtactc ttgttttagc                                         20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 23
ttccaaccaa cggttgagtc                                         20

<210> SEQ ID NO 24
<211> LENGTH: 2276
<212> TYPE: DNA
<213> ORGANISM: Mus musculus
<220> FEATURE:
<221> NAME/KEY: CDS
<222> LOCATION: (63)..(1709)
<223> OTHER INFORMATION: Clone: MNramp-1

<400> SEQUENCE: 24
attgaggagc tagttgccag gcctggtgac cacacacaga gtatcctgcc gcctgcgtcc    60 tc atg att agt gac aag agc ccc ccg agg ctg agc agg ccc agt tat     107
   Met Ile Ser Asp Lys Ser Pro Pro Arg Leu Ser Arg Pro Ser Tyr
   1               5                  10                  15
```

-continued

```
ggc tcc att tcc agc ctg cct ggc cca gca cct cag cca gcg cct tgc       155
Gly Ser Ile Ser Ser Leu Pro Gly Pro Ala Pro Gln Pro Ala Pro Cys
                 20                  25                  30 cgg gag acc tac ctg agt gag aag atc ccc att ccc agc gca gac cag       203
Arg Glu Thr Tyr Leu Ser Glu Lys Ile Pro Ile Pro Ser Ala Asp Gln
             35                  40                  45 ggt aca ttc agc ctg agg aag ctg tgg gcg ttc acg ggg cct ggt ttc       251
Gly Thr Phe Ser Leu Arg Lys Leu Trp Ala Phe Thr Gly Pro Gly Phe
         50                  55                  60 ctc atg agc atc gct ttc ctt gac ccg gga aac att gag tcc gac ctt       299
Leu Met Ser Ile Ala Phe Leu Asp Pro Gly Asn Ile Glu Ser Asp Leu
     65                  70                  75 caa gct ggc gct gtg gct ggg ttc aaa ctc ctc tgg gtg ctc ctc tgg       347
Gln Ala Gly Ala Val Ala Gly Phe Lys Leu Leu Trp Val Leu Leu Trp
 80                  85                  90                  95 gcg act gtg cta ggt ttg ctg tgc cag cgg ctg gct gcc cgg ctg ggc       395
Ala Thr Val Leu Gly Leu Leu Cys Gln Arg Leu Ala Ala Arg Leu Gly
                100                 105                 110 gtg gtg aca ggc aag gac ttg ggt gaa gtc tgc cat ctc tac tac ccc       443
Val Val Thr Gly Lys Asp Leu Gly Glu Val Cys His Leu Tyr Tyr Pro
            115                 120                 125 aag gtg ccc cgc atc ctc ctc tgg ctg acc att gag ctg gcc att gtg       491
Lys Val Pro Arg Ile Leu Leu Trp Leu Thr Ile Glu Leu Ala Ile Val
        130                 135                 140 ggc tca gat atg cag gaa gtc atc ggg acg gct atc tcc ttc aat ctg       539
Gly Ser Asp Met Gln Glu Val Ile Gly Thr Ala Ile Ser Phe Asn Leu
    145                 150                 155 ctc tcc gct gga cgc atc ccg ctg tgg ggc ggt gta ctg atc acc att       587
Leu Ser Ala Gly Arg Ile Pro Leu Trp Gly Gly Val Leu Ile Thr Ile
160                 165                 170                 175 gtg gac acc ttc ttc ttc ctc ttc ttg gat aac tat ggt ttg cgc aag       635
Val Asp Thr Phe Phe Phe Leu Phe Leu Asp Asn Tyr Gly Leu Arg Lys
                180                 185                 190 ctg gaa gct ttc ttc ggt ctc ctc att acc ata atg gct ttg acc ttc       683
Leu Glu Ala Phe Phe Gly Leu Leu Ile Thr Ile Met Ala Leu Thr Phe
            195                 200                 205 ggc tat gag tat gtg gta gca cac cct tcc cag gga gcg ctc ctt aag       731
Gly Tyr Glu Tyr Val Val Ala His Pro Ser Gln Gly Ala Leu Leu Lys
        210                 215                 220 ggc ctg gtg ctg ccc acc tgt ccg ggc tgt ggg cag ccc gag ctg ctg       779
Gly Leu Val Leu Pro Thr Cys Pro Gly Cys Gly Gln Pro Glu Leu Leu
    225                 230                 235 cag gca gtg ggc atc gtc ggt gcc atc atc atg ccc cat aac atc tac       827
Gln Ala Val Gly Ile Val Gly Ala Ile Ile Met Pro His Asn Ile Tyr
240                 245                 250                 255 ctg cac tca gcc ttg gtc aag tct aga gaa gta gac aga acc cgc cgg       875
Leu His Ser Ala Leu Val Lys Ser Arg Glu Val Asp Arg Thr Arg Arg
                260                 265                 270 gtg gat gtt cga gaa gcc aac atg tac ttc ctg att gag gcc acc atc       923
Val Asp Val Arg Glu Ala Asn Met Tyr Phe Leu Ile Glu Ala Thr Ile
            275                 280                 285 gcc cta tcg gtg tcc ttc atc atc aac ctc ttc gtc atg gct gtt ttt       971
Ala Leu Ser Val Ser Phe Ile Ile Asn Leu Phe Val Met Ala Val Phe
        290                 295                 300 ggt cag gcc ttc tac cag caa acc aat gag gaa gcg ttc aac atc tgt      1019
Gly Gln Ala Phe Tyr Gln Gln Thr Asn Glu Glu Ala Phe Asn Ile Cys
    305                 310                 315 gcc aac agc agc ctc cag aac tat gct aag atc ttc ccc agg gac aat      1067
Ala Asn Ser Ser Leu Gln Asn Tyr Ala Lys Ile Phe Pro Arg Asp Asn
```

-continued

```
              320                 325                 330                 335
aac act gtg tca gtg gat att tat caa gga ggt gtg atc cta ggc tgt          1115
Asn Thr Val Ser Val Asp Ile Tyr Gln Gly Gly Val Ile Leu Gly Cys
                340                 345                 350 ctc ttt ggc cct gcg gcc ctc tac atc tgg gca gta ggt ctc ctg gca          1163
Leu Phe Gly Pro Ala Ala Leu Tyr Ile Trp Ala Val Gly Leu Leu Ala
                355                 360                 365 gcg ggg cag agt tct act atg acc ggc acc tat gca gga cag ttc gtg          1211
Ala Gly Gln Ser Ser Thr Met Thr Gly Thr Tyr Ala Gly Gln Phe Val
            370                 375                 380 atg gag ggt ttc ctt aag ctg cgg tgg tcc cgc ttc gct cgg gtc ctt          1259
Met Glu Gly Phe Leu Lys Leu Arg Trp Ser Arg Phe Ala Arg Val Leu
            385                 390                 395 ctc acg cgc tct tgc gcc atc ctg ccc act gtg ttg gtg gct gtc ttc          1307
Leu Thr Arg Ser Cys Ala Ile Leu Pro Thr Val Leu Val Ala Val Phe
400                 405                 410                 415 cga gac ctg aag gac ctg tcc ggc ctc aac gat cta ctc aat gtt ctg          1355
Arg Asp Leu Lys Asp Leu Ser Gly Leu Asn Asp Leu Leu Asn Val Leu
                420                 425                 430 cag agt cta ctg ctg ccc ttc gct gta ctg ccc att ttg act ttc acc          1403
Gln Ser Leu Leu Leu Pro Phe Ala Val Leu Pro Ile Leu Thr Phe Thr
                435                 440                 445 agc atg cca gct gtc atg cag gag ttt gcc aac ggc cgg atg agc aaa          1451
Ser Met Pro Ala Val Met Gln Glu Phe Ala Asn Gly Arg Met Ser Lys
                450                 455                 460 gcc atc act tcg tgc atc atg gcg cta gtc tgc gcc atc aac ctg tac          1499
Ala Ile Thr Ser Cys Ile Met Ala Leu Val Cys Ala Ile Asn Leu Tyr
465                 470                 475 ttt gtg atc agc tac ctg ccc agc ctc ccg cac cct gcc tac ttt ggc          1547
Phe Val Ile Ser Tyr Leu Pro Ser Leu Pro His Pro Ala Tyr Phe Gly
480                 485                 490                 495 ctt gtg gct ctg ttc gca ata ggt tac ttg ggc ctg act gct tat ctg          1595
Leu Val Ala Leu Phe Ala Ile Gly Tyr Leu Gly Leu Thr Ala Tyr Leu
                500                 505                 510 gcc tgg acc tgt tgc atc gcc cac gga gcc acc ttc ctg acc cac agc          1643
Ala Trp Thr Cys Cys Ile Ala His Gly Ala Thr Phe Leu Thr His Ser
                515                 520                 525 tcc cac aag cac ttc tta tat ggg ctc cct aac gag gag cag gga ggc          1691
Ser His Lys His Phe Leu Tyr Gly Leu Pro Asn Glu Glu Gln Gly Gly
                530                 535                 540 gtg cag ggt tcc ggg tga ccgcggcatc agcaagcaa agaggcaaca                  1739
Val Gln Gly Ser Gly
            545 gggcagacac agcagagcaa ttggaggtcc cctactggct ttctggatta ccggtttcca        1799 gtttggacaa gtgctttacc tcggaataat gacaccattc ttatcaccac aacctaagag        1859 acttaaaaaa cacagtgcct ggggcgagag atggctcagg tgtgagaaca ctagccacca        1919 cccttttcaga agatggggat tcaattccca gcatcaacgt ggtggctttc aactgaaggt      1979 gactccagtt cccagaacac ctcaaacaga actgccacaa ctccattgtc tcactccagc        2039 tcgtggaaga tgaagggagg agtcctaaag agttctaggt cgggtctctg gagagacggc        2099 tcagctgtta agagcaccgg actgctcttc cagaggtcct gagttcaatt cccagcaacc        2159 acatggtggc tcacaaccat ccataatggg atccctcttc tggtgtgtct gaagacaaca        2219 acagtgtcct cacatatata aaataaataa atcttaaaaa aaaaaaaaaa aataaac           2276
```

<210> SEQ ID NO 25
<211> LENGTH: 548

-continued

```
<212> TYPE: PRT
<213> ORGANISM: Mus musculus

<400> SEQUENCE: 25

Met Ile Ser Asp Lys Ser Pro Arg Leu Ser Arg Pro Ser Tyr Gly
 1               5                  10                  15

Ser Ile Ser Ser Leu Pro Gly Pro Ala Pro Gln Pro Ala Pro Cys Arg
                20                  25                  30

Glu Thr Tyr Leu Ser Glu Lys Ile Pro Ile Pro Ser Ala Asp Gln Gly
                35                  40                  45

Thr Phe Ser Leu Arg Lys Leu Trp Ala Phe Thr Gly Pro Gly Phe Leu
            50                  55                  60

Met Ser Ile Ala Phe Leu Asp Pro Gly Asn Ile Glu Ser Asp Leu Gln
 65                  70                  75                  80

Ala Gly Ala Val Ala Gly Phe Lys Leu Leu Trp Val Leu Leu Trp Ala
                85                  90                  95

Thr Val Leu Gly Leu Leu Cys Gln Arg Leu Ala Ala Arg Leu Gly Val
                100                 105                 110

Val Thr Gly Lys Asp Leu Gly Glu Val Cys His Leu Tyr Tyr Pro Lys
                115                 120                 125

Val Pro Arg Ile Leu Leu Trp Leu Thr Ile Glu Leu Ala Ile Val Gly
        130                 135                 140

Ser Asp Met Gln Glu Val Ile Gly Thr Ala Ile Ser Phe Asn Leu Leu
145                 150                 155                 160

Ser Ala Gly Arg Ile Pro Leu Trp Gly Gly Val Leu Ile Thr Ile Val
                165                 170                 175

Asp Thr Phe Phe Phe Leu Phe Leu Asp Asn Tyr Gly Leu Arg Lys Leu
            180                 185                 190

Glu Ala Phe Phe Gly Leu Leu Ile Thr Ile Met Ala Leu Thr Phe Gly
        195                 200                 205

Tyr Glu Tyr Val Val Ala His Pro Ser Gln Gly Ala Leu Leu Lys Gly
    210                 215                 220

Leu Val Leu Pro Thr Cys Pro Gly Cys Gly Gln Pro Glu Leu Leu Gln
225                 230                 235                 240

Ala Val Gly Ile Val Gly Ala Ile Ile Met Pro His Asn Ile Tyr Leu
                245                 250                 255

His Ser Ala Leu Val Lys Ser Arg Glu Val Asp Arg Thr Arg Arg Val
            260                 265                 270

Asp Val Arg Glu Ala Asn Met Tyr Phe Leu Ile Glu Ala Thr Ile Ala
        275                 280                 285

Leu Ser Val Ser Phe Ile Ile Asn Leu Phe Val Met Ala Val Phe Gly
    290                 295                 300

Gln Ala Phe Tyr Gln Gln Thr Asn Glu Glu Ala Phe Asn Ile Cys Ala
305                 310                 315                 320

Asn Ser Ser Leu Gln Asn Tyr Ala Lys Ile Phe Pro Arg Asp Asn Asn
                325                 330                 335

Thr Val Ser Val Asp Ile Tyr Gln Gly Gly Val Ile Leu Gly Cys Leu
            340                 345                 350

Phe Gly Pro Ala Ala Leu Tyr Ile Trp Ala Val Gly Leu Leu Ala Ala
        355                 360                 365

Gly Gln Ser Ser Thr Met Thr Gly Thr Tyr Ala Gly Gln Phe Val Met
    370                 375                 380

Glu Gly Phe Leu Lys Leu Arg Trp Ser Arg Phe Ala Arg Val Leu Leu
385                 390                 395                 400
```

```
Thr Arg Ser Cys Ala Ile Leu Pro Thr Val Leu Val Ala Val Phe Arg
            405                 410                 415
Asp Leu Lys Asp Leu Ser Gly Leu Asn Asp Leu Leu Asn Val Leu Gln
            420                 425                 430
Ser Leu Leu Leu Pro Phe Ala Val Leu Pro Ile Leu Thr Phe Thr Ser
            435                 440                 445
Met Pro Ala Val Met Gln Glu Phe Ala Asn Gly Arg Met Ser Lys Ala
            450                 455                 460
Ile Thr Ser Cys Ile Met Ala Leu Val Cys Ala Ile Asn Leu Tyr Phe
465                 470                 475                 480
Val Ile Ser Tyr Leu Pro Ser Leu Pro His Pro Ala Tyr Phe Gly Leu
            485                 490                 495
Val Ala Leu Phe Ala Ile Gly Tyr Leu Gly Leu Thr Ala Tyr Leu Ala
            500                 505                 510
Trp Thr Cys Cys Ile Ala His Gly Ala Thr Phe Leu Thr His Ser Ser
            515                 520                 525
His Lys His Phe Leu Tyr Gly Leu Pro Asn Glu Glu Gln Gly Gly Val
            530                 535                 540
Gln Gly Ser Gly
545

<210> SEQ ID NO 26
<211> LENGTH: 2967
<212> TYPE: DNA
<213> ORGANISM: Mus musculus
<220> FEATURE:
<221> NAME/KEY: CDS
<222> LOCATION: (50)..(1756)
<223> OTHER INFORMATION: Clone: MNramp-2

<400> SEQUENCE: 26
tggcggagcc gaatcctatt ctaagagcac agaccctcag gtatctacc atg gtg ttg    58
                                                    Met Val Leu
                                                      1 gat cct aaa gaa aag atg cca gac gat ggc gct tct ggg gac cat gga   106
Asp Pro Lys Glu Lys Met Pro Asp Asp Gly Ala Ser Gly Asp His Gly
  5                  10                  15 gac tct gcc agc ctt ggc gcc atc aac cct gcc tac agc aac tca tcc   154
Asp Ser Ala Ser Leu Gly Ala Ile Asn Pro Ala Tyr Ser Asn Ser Ser
 20                  25                  30                  35 ctc cca cat tcc act gga gac tct gag gag ccc ttc acc acc tac ttt   202
Leu Pro His Ser Thr Gly Asp Ser Glu Glu Pro Phe Thr Thr Tyr Phe
                 40                  45                  50 gat gag aaa atc ccc att cct gag gag gag tac tct tgt ttt agc ttt   250
Asp Glu Lys Ile Pro Ile Pro Glu Glu Glu Tyr Ser Cys Phe Ser Phe
             55                  60                  65 cgt aaa ctc tgg gcg ttc acg ggg cct ggc ttt ctt atg agc att gcc   298
Arg Lys Leu Trp Ala Phe Thr Gly Pro Gly Phe Leu Met Ser Ile Ala
         70                  75                  80 tac cta gac cca gga aac atc gaa tct gat ttg cag tct gga gca gtg   346
Tyr Leu Asp Pro Gly Asn Ile Glu Ser Asp Leu Gln Ser Gly Ala Val
     85                  90                  95 gct gga ttt aag ctg ctc tgg gtg ctc ctc ttg gcc acc att gtg ggg   394
Ala Gly Phe Lys Leu Leu Trp Val Leu Leu Leu Ala Thr Ile Val Gly
100                 105                 110                 115 ctg ctg ctc cag cgc ctt gca gcg aga ctt gga gtg gtc acc ggc ttg   442
Leu Leu Leu Gln Arg Leu Ala Ala Arg Leu Gly Val Val Thr Gly Leu
                120                 125                 130
```

```
cat ctt gct gaa gta tgt cac cgt cag tat ccc aag gtc cca cgg atc     490
His Leu Ala Glu Val Cys His Arg Gln Tyr Pro Lys Val Pro Arg Ile
            135                 140                 145 atc ctg tgg ctg atg gtg gag ttg gca atc att ggt tct gac atg cag     538
Ile Leu Trp Leu Met Val Glu Leu Ala Ile Ile Gly Ser Asp Met Gln
        150                 155                 160 gaa gtc att ggc tca gcc atc gcc atc aat ctc ctg tct gca gga agg     586
Glu Val Ile Gly Ser Ala Ile Ala Ile Asn Leu Leu Ser Ala Gly Arg
    165                 170                 175 gtc cct gtg tgg ggc gga gtc ctc atc acc atc gca gac act ttt gtg     634
Val Pro Val Trp Gly Gly Val Leu Ile Thr Ile Ala Asp Thr Phe Val
180                 185                 190                 195 ttt ctt ttt ttg gac aaa tat ggc ttg cgg aag ctg gaa gcg ttt ttt     682
Phe Leu Phe Leu Asp Lys Tyr Gly Leu Arg Lys Leu Glu Ala Phe Phe
            200                 205                 210 ggc ttt ctc atc act atc atg gcc ctc acg ttt gga tat gag tac att     730
Gly Phe Leu Ile Thr Ile Met Ala Leu Thr Phe Gly Tyr Glu Tyr Ile
        215                 220                 225 aca gtg aag ccc agc cag agc caa gta ctc agg ggc atg ttc gtg ccg     778
Thr Val Lys Pro Ser Gln Ser Gln Val Leu Arg Gly Met Phe Val Pro
    230                 235                 240 tcc tgt cca ggg tgc cgc acc cct cag gtg gag cag gcg gtg ggc atc     826
Ser Cys Pro Gly Cys Arg Thr Pro Gln Val Glu Gln Ala Val Gly Ile
245                 250                 255 gtg gga gct gtg atc atg ccg cac aac atg tac ctg cat tct gcc tta     874
Val Gly Ala Val Ile Met Pro His Asn Met Tyr Leu His Ser Ala Leu
260                 265                 270                 275 gtc aag tct aga cag gtg aat cgg gcc aat aag cag gaa gtg cgg gaa     922
Val Lys Ser Arg Gln Val Asn Arg Ala Asn Lys Gln Glu Val Arg Glu
            280                 285                 290 gcc aat aag tac ttc ttc atc gag tcc tgc atc gcg ctc ttt gtt tcc     970
Ala Asn Lys Tyr Phe Phe Ile Glu Ser Cys Ile Ala Leu Phe Val Ser
        295                 300                 305 ttc atc atc aat gtc ttt gtc gtg tcc gtc ttt gct gaa gca ttt ttt    1018
Phe Ile Ile Asn Val Phe Val Val Ser Val Phe Ala Glu Ala Phe Phe
    310                 315                 320 gag aaa acc aac aag cag gtg gtt gaa gtc tgc aaa aat aac agc agc    1066
Glu Lys Thr Asn Lys Gln Val Val Glu Val Cys Lys Asn Asn Ser Ser
325                 330                 335 ccc cat gct gac ctc ttt ccc agt gac aac tct act ctg gct gtg gac    1114
Pro His Ala Asp Leu Phe Pro Ser Asp Asn Ser Thr Leu Ala Val Asp
340                 345                 350                 355 atc tac aaa ggg ggt gtt gtg ctt gga tgt tac ttc ggg cct gca gct    1162
Ile Tyr Lys Gly Gly Val Val Leu Gly Cys Tyr Phe Gly Pro Ala Ala
            360                 365                 370 ctc tac atc tgg gca gtg ggg atc ctg gct gcc ggt cag agc tcc acc    1210
Leu Tyr Ile Trp Ala Val Gly Ile Leu Ala Ala Gly Gln Ser Ser Thr
        375                 380                 385 atg act gga acc tat tct ggc cag ttt gtc atg gag gga ttc ctg aac    1258
Met Thr Gly Thr Tyr Ser Gly Gln Phe Val Met Glu Gly Phe Leu Asn
    390                 395                 400 cta aaa tgg tcg cgc ttt gcc cga gtg atc ctg acc cgg tct atc gcc    1306
Leu Lys Trp Ser Arg Phe Ala Arg Val Ile Leu Thr Arg Ser Ile Ala
405                 410                 415 atc atc ccc acc ctc ctc gtc gct gtc ttc cag gat gtg gag cac cta    1354
Ile Ile Pro Thr Leu Leu Val Ala Val Phe Gln Asp Val Glu His Leu
420                 425                 430                 435 acg ggg atg aat gac ttc ctg aat gtc ctg cag agc tta cag ctc ccc    1402
Thr Gly Met Asn Asp Phe Leu Asn Val Leu Gln Ser Leu Gln Leu Pro
            440                 445                 450
```

-continued

```
ttt gct ctc ata ccc atc ctc acg ttc aca agc ctg cgg cca gtg atg      1450
Phe Ala Leu Ile Pro Ile Leu Thr Phe Thr Ser Leu Arg Pro Val Met
            455                 460                 465 agt gag ttt tcc aat gga ata ggc tgg agg att gcc ggt ggc atc ctg      1498
Ser Glu Phe Ser Asn Gly Ile Gly Trp Arg Ile Ala Gly Gly Ile Leu
        470                 475                 480 gtc ctg atc gtc tgc tcc atc aac atg tac ttt gta gtg gtt tat gtc      1546
Val Leu Ile Val Cys Ser Ile Asn Met Tyr Phe Val Val Val Tyr Val
    485                 490                 495 cag gag cta ggg cat gtg gca ctc tat gtg gtg gct gca gtg gtt agc      1594
Gln Glu Leu Gly His Val Ala Leu Tyr Val Val Ala Val Val Ser
500                 505                 510                 515 gtg gct tat ttg acc ttt gtg ttc tac ttg ggt tgg cag tgt ttg att      1642
Val Ala Tyr Leu Thr Phe Val Phe Tyr Leu Gly Trp Gln Cys Leu Ile
                520                 525                 530 gca ttg ggt ctg tct ttc ctg gac tgt gga cgc tcg tac cgc ctg gga      1690
Ala Leu Gly Leu Ser Phe Leu Asp Cys Gly Arg Ser Tyr Arg Leu Gly
            535                 540                 545 ctg acc gct cag cct gaa ctc tat ctt ctg aac acc gtg gat gct gac      1738
Leu Thr Ala Gln Pro Glu Leu Tyr Leu Leu Asn Thr Val Asp Ala Asp
        550                 555                 560 tca gtg gtg tcc aga tga ctaacagccc aggagacctt aagaacactt             1786
Ser Val Val Ser Arg
    565 tctctaagcc ctttcgggcc aagtgcctgt tagcaaatcc cttagttcgg aggtgagctt    1846 gttcaaaggt ttttgaacaa aggagaagtt ctcctcacgg actcagggta aaagctgaca    1906 gttgcgtatg ggtcagagac ccttcggagg cagtgggcct gtggcagctg tgcagtccct    1966 caggcttgtg tctgcacttc tggggtttaa agtgtatcga tatgtattta tgtgaaccca    2026 aacgtgccag tttgggtaag atttttaaggt tataaaactt gatagatttt tacaaatgcc   2086 tttcaggtga gttaggtctt tgttctatttt gggtaacaaa tgagaaaggg acctttctga   2146 cgatgaactt ccccaaaata actcttgaag cgctgcttta ccacagtgtg tgtgtgtgtg    2206 tgtgtgtgtg tgtgtgtgcg cgcgcgcgtg cctgcctgct tctgcttgtg ggggccacgg    2266 gttggcatca ggtgtctcca gtctctacca cagtgtgtgt gtgtgtgtgt gtgtgtgtgt    2326 gtgtgtgtgt gtgtgtgtgt gtgtgcgtgc gcgagtgcct gcctgcttct gcttgtgggg    2386 gccacgggtt ggcatcaggt gtctccagtc tctctgaa catggagttc agtgtgtgac      2446 tgagctagcc agccagtaag ttcaaggatc ctcctggcct cgcgcccaa cactgtggtc     2506 ccagatcagc tgctacgccc agattttaca cagtgctggg gacccaaact caggtcttcc    2566 tggacagcag gtactttacc aactttcccc ctttgtctct acatcaagtg tgtctgtggc    2626 tgttgttccg ttggtgtctg tccacctgcc cttttcttccc actctacgcg ctgacactcc   2686 acacactgtc ctcaccctgt ctctaagggc cgcccgtatg tgtaccgctg agtgttcctg    2746 aggaatttaa gcattttaag gtgtgtgtta gcagaggtct gaggctcgca ctcgatggga    2806 acacagacca tcagtttcac tttaagcacc gacactccaa acgcgcgtgt gcaggtagtg    2866 aagcttttttg gttttttgctt taatcccaac cagaaataat catccttgtt ataataaagt  2926 tcatgcttaa tagctaaaaa aaaaaaaaaa aaaaattaaa c                        2967
```

<210> SEQ ID NO 27
<211> LENGTH: 568
<212> TYPE: PRT
<213> ORGANISM: Mus musculus -continued

```
<400> SEQUENCE: 27

Met Val Leu Asp Pro Lys Glu Lys Met Pro Asp Asp Gly Ala Ser Gly
 1               5                  10                  15

Asp His Gly Asp Ser Ala Ser Leu Gly Ala Ile Asn Pro Ala Tyr Ser
                20                  25                  30

Asn Ser Ser Leu Pro His Ser Thr Gly Asp Ser Glu Glu Pro Phe Thr
            35                  40                  45

Thr Tyr Phe Asp Glu Lys Ile Pro Ile Pro Glu Glu Tyr Ser Cys
 50                  55                  60

Phe Ser Phe Arg Lys Leu Trp Ala Phe Thr Gly Pro Gly Phe Leu Met
 65                  70                  75                  80

Ser Ile Ala Tyr Leu Asp Pro Gly Asn Ile Glu Ser Asp Leu Gln Ser
                85                  90                  95

Gly Ala Val Ala Gly Phe Lys Leu Leu Trp Val Leu Leu Leu Ala Thr
                100                 105                 110

Ile Val Gly Leu Leu Leu Gln Arg Leu Ala Ala Arg Leu Gly Val Val
            115                 120                 125

Thr Gly Leu His Leu Ala Glu Val Cys His Arg Gln Tyr Pro Lys Val
130                 135                 140

Pro Arg Ile Ile Leu Trp Leu Met Val Glu Leu Ala Ile Ile Gly Ser
145                 150                 155                 160

Asp Met Gln Glu Val Ile Gly Ser Ala Ile Ala Ile Asn Leu Leu Ser
                165                 170                 175

Ala Gly Arg Val Pro Val Trp Gly Gly Val Leu Ile Thr Ile Ala Asp
                180                 185                 190

Thr Phe Val Phe Leu Phe Leu Asp Lys Tyr Gly Leu Arg Lys Leu Glu
            195                 200                 205

Ala Phe Phe Gly Phe Leu Ile Thr Ile Met Ala Leu Thr Phe Gly Tyr
210                 215                 220

Glu Tyr Ile Thr Val Lys Pro Ser Gln Ser Gln Val Leu Arg Gly Met
225                 230                 235                 240

Phe Val Pro Ser Cys Pro Gly Cys Arg Thr Pro Gln Val Glu Gln Ala
                245                 250                 255

Val Gly Ile Val Gly Ala Val Ile Met Pro His Asn Met Tyr Leu His
                260                 265                 270

Ser Ala Leu Val Lys Ser Arg Gln Val Asn Arg Ala Asn Lys Gln Glu
            275                 280                 285

Val Arg Glu Ala Asn Lys Tyr Phe Phe Ile Glu Ser Cys Ile Ala Leu
290                 295                 300

Phe Val Ser Phe Ile Ile Asn Val Phe Val Ser Val Phe Ala Glu
305                 310                 315                 320

Ala Phe Phe Glu Lys Thr Asn Lys Gln Val Val Glu Val Cys Lys Asn
                325                 330                 335

Asn Ser Ser Pro His Ala Asp Leu Phe Pro Ser Asp Asn Ser Thr Leu
                340                 345                 350

Ala Val Asp Ile Tyr Lys Gly Gly Val Leu Gly Cys Tyr Phe Gly
            355                 360                 365

Pro Ala Ala Leu Tyr Ile Trp Ala Val Gly Ile Leu Ala Ala Gly Gln
370                 375                 380

Ser Ser Thr Met Thr Gly Thr Tyr Ser Gly Gln Phe Val Met Glu Gly
385                 390                 395                 400

Phe Leu Asn Leu Lys Trp Ser Arg Phe Ala Arg Val Ile Leu Thr Arg
                405                 410                 415
```

```
Ser Ile Ala Ile Ile Pro Thr Leu Leu Val Ala Val Phe Gln Asp Val
            420                 425                 430

Glu His Leu Thr Gly Met Asn Asp Phe Leu Asn Val Leu Gln Ser Leu
            435                 440                 445

Gln Leu Pro Phe Ala Leu Ile Pro Ile Leu Thr Phe Thr Ser Leu Arg
        450                 455                 460

Pro Val Met Ser Glu Phe Ser Asn Gly Ile Gly Trp Arg Ile Ala Gly
465                 470                 475                 480

Gly Ile Leu Val Leu Ile Val Cys Ser Ile Asn Met Tyr Phe Val Val
                485                 490                 495

Val Tyr Val Gln Glu Leu Gly His Val Ala Leu Tyr Val Val Ala Ala
            500                 505                 510

Val Val Ser Val Ala Tyr Leu Thr Phe Val Phe Tyr Leu Gly Trp Gln
            515                 520                 525

Cys Leu Ile Ala Leu Gly Leu Ser Phe Leu Asp Cys Gly Arg Ser Tyr
        530                 535                 540

Arg Leu Gly Leu Thr Ala Gln Pro Glu Leu Tyr Leu Leu Asn Thr Val
545                 550                 555                 560

Asp Ala Asp Ser Val Val Ser Arg
                565

<210> SEQ ID NO 28
<211> LENGTH: 584
<212> TYPE: PRT
<213> ORGANISM: Mus musculus

<400> SEQUENCE: 28

Gly Gly Ala Glu Ser Tyr Ser Lys Ser Thr Asp Pro Gln Val Ser Thr
  1               5                  10                  15

Met Val Leu Asp Pro Lys Glu Lys Met Pro Asp Asp Gly Ala Ser Gly
                20                  25                  30

Asp His Gly Asp Ser Ala Ser Leu Gly Ala Ile Asn Pro Ala Tyr Ser
            35                  40                  45

Asn Ser Ser Leu Pro His Ser Thr Gly Asp Ser Glu Glu Pro Phe Thr
        50                  55                  60

Thr Tyr Phe Asp Glu Lys Ile Pro Ile Pro Glu Glu Tyr Ser Cys
 65                 70                  75                  80

Phe Ser Phe Arg Lys Leu Trp Ala Phe Thr Gly Pro Gly Phe Leu Met
                85                  90                  95

Ser Ile Ala Tyr Leu Asp Pro Gly Asn Ile Glu Ser Asp Leu Gln Ser
                100                 105                 110

Gly Ala Val Ala Gly Phe Lys Leu Leu Trp Val Leu Leu Leu Ala Thr
            115                 120                 125

Ile Val Gly Leu Leu Gln Arg Leu Ala Ala Arg Leu Gly Val Val
            130                 135                 140

Thr Gly Leu His Leu Ala Glu Val Cys His Arg Gln Tyr Pro Lys Val
145                 150                 155                 160

Pro Arg Ile Ile Leu Trp Leu Met Val Glu Leu Ala Ile Ile Gly Ser
                165                 170                 175

Asp Met Gln Glu Val Ile Gly Ser Ala Ile Ala Ile Asn Leu Leu Ser
                180                 185                 190

Ala Gly Arg Val Pro Val Trp Gly Gly Val Leu Ile Thr Ile Ala Asp
            195                 200                 205

Thr Phe Val Phe Leu Phe Leu Asp Lys Tyr Gly Leu Arg Lys Leu Glu
```

```
            210                 215                 220
Ala Phe Gly Phe Leu Ile Thr Ile Met Ala Leu Thr Phe Gly Tyr
225                 230                 235                 240

Glu Tyr Ile Thr Val Lys Pro Ser Gln Ser Gln Val Leu Arg Gly Met
                245                 250                 255

Phe Val Pro Ser Cys Pro Gly Cys Arg Thr Pro Gln Val Glu Gln Ala
                260                 265                 270

Val Gly Ile Val Gly Ala Val Ile Met Pro His Asn Met Tyr Leu His
                275                 280                 285

Ser Ala Leu Val Lys Ser Arg Gln Val Asn Arg Ala Asn Lys Gln Glu
290                 295                 300

Val Arg Glu Ala Asn Lys Tyr Phe Phe Ile Glu Ser Cys Ile Ala Leu
305                 310                 315                 320

Phe Val Ser Phe Ile Ile Asn Val Phe Val Ser Val Phe Ala Glu
                325                 330                 335

Ala Phe Phe Glu Lys Thr Asn Lys Gln Val Glu Val Cys Lys Asn
                340                 345                 350

Asn Ser Ser Pro His Ala Asp Leu Phe Pro Ser Asp Asn Ser Thr Leu
                355                 360                 365

Ala Val Asp Ile Tyr Lys Gly Gly Val Val Leu Gly Cys Tyr Phe Gly
370                 375                 380

Pro Ala Leu Tyr Ile Trp Ala Val Gly Ile Leu Ala Ala Gly Gln
385                 390                 395                 400

Ser Ser Thr Met Thr Gly Thr Tyr Ser Gly Gln Phe Val Met Glu Gly
                405                 410                 415

Phe Leu Asn Leu Lys Trp Ser Arg Phe Ala Arg Val Ile Leu Thr Arg
                420                 425                 430

Ser Ile Ala Ile Ile Pro Thr Leu Leu Val Ala Val Phe Gln Asp Val
                435                 440                 445

Glu His Leu Thr Gly Met Asn Asp Phe Leu Asn Val Leu Gln Ser Leu
                450                 455                 460

Gln Leu Pro Phe Ala Leu Ile Pro Ile Leu Thr Phe Thr Ser Leu Arg
465                 470                 475                 480

Pro Val Met Ser Glu Phe Ser Asn Gly Ile Gly Trp Arg Ile Ala Gly
                485                 490                 495

Gly Ile Leu Val Leu Ile Val Cys Ser Ile Asn Met Tyr Phe Val Val
                500                 505                 510

Val Tyr Val Gln Glu Leu Gly His Val Ala Leu Tyr Val Val Ala Ala
                515                 520                 525

Val Val Ser Val Ala Tyr Leu Thr Phe Val Phe Tyr Leu Gly Trp Gln
                530                 535                 540

Cys Leu Ile Ala Leu Gly Leu Ser Phe Leu Asp Cys Gly Arg Ser Tyr
545                 550                 555                 560

Arg Leu Gly Leu Thr Ala Gln Pro Glu Leu Tyr Leu Leu Asn Thr Val
                565                 570                 575

Asp Ala Asp Ser Val Val Ser Arg
                580

<210> SEQ ID NO 29
<211> LENGTH: 2007
<212> TYPE: DNA
<213> ORGANISM: Homo sapiens
<220> FEATURE:
<221> NAME/KEY: CDS
<222> LOCATION: (77)..(1729)
```

-continued

<223> OTHER INFORMATION: Clone: HNramp-1

<400> SEQUENCE: 29

```
tctgggcacg ggtgcaggct gaggagctgc ccagagcacc gctcacactc ccagagtacc    60
tgaagtcggc atttca atg aca ggt gac aag ggt ccc caa agg cta agc ggg   112
               Met Thr Gly Asp Lys Gly Pro Gln Arg Leu Ser Gly
                 1               5                  10 tcc agc tat ggt tcc atc tcc agc ccg acc agc ccg acc agc cca ggg     160
Ser Ser Tyr Gly Ser Ile Ser Ser Pro Thr Ser Pro Thr Ser Pro Gly
         15                  20                  25 cca cag caa gca cct ccc aga gag acc tac ctg agt gag aag atc ccc     208
Pro Gln Gln Ala Pro Pro Arg Glu Thr Tyr Leu Ser Glu Lys Ile Pro
     30                  35                  40 atc cca gac aca aaa ccg ggc acc ttc agc ctg cgg aag cta tgg gcc     256
Ile Pro Asp Thr Lys Pro Gly Thr Phe Ser Leu Arg Lys Leu Trp Ala
 45                  50                  55                  60 ttc acg ggg cct ggc ttc ctc atg agc att gct ttc ctg gac cca gga     304
Phe Thr Gly Pro Gly Phe Leu Met Ser Ile Ala Phe Leu Asp Pro Gly
                 65                  70                  75 aac atc gag tca gat ctt cag gct ggc gcc gtg gcg gga ttc aaa ctt     352
Asn Ile Glu Ser Asp Leu Gln Ala Gly Ala Val Ala Gly Phe Lys Leu
             80                  85                  90 ctc tgg gtg ctg ctc tgg gcc acc gtg ttg ggc ttg ctc tgc cag cga     400
Leu Trp Val Leu Leu Trp Ala Thr Val Leu Gly Leu Leu Cys Gln Arg
         95                 100                 105 ctg gct gca cgt ctg ggc gtg gtg aca ggc aag gac ttg ggc gag gtc     448
Leu Ala Ala Arg Leu Gly Val Val Thr Gly Lys Asp Leu Gly Glu Val
    110                 115                 120 tgc cat ctc tac tac cct aag gtg ccc cgc acc gtc ctc tgg ctg acc     496
Cys His Leu Tyr Tyr Pro Lys Val Pro Arg Thr Val Leu Trp Leu Thr
125                 130                 135                 140 atc gag cta gcc att gtg ggc tcc gac atg cag gaa gtc atc ggc acg     544
Ile Glu Leu Ala Ile Val Gly Ser Asp Met Gln Glu Val Ile Gly Thr
                145                 150                 155 gcc att gca ttc aat ctg ctc tca gct gga cga atc cca ctc tgg ggt     592
Ala Ile Ala Phe Asn Leu Leu Ser Ala Gly Arg Ile Pro Leu Trp Gly
            160                 165                 170 ggc gtc ctc atc acc atc gtg gac acc ttc ttc ttc ctc ttc ctc gat     640
Gly Val Leu Ile Thr Ile Val Asp Thr Phe Phe Phe Leu Phe Leu Asp
        175                 180                 185 aac tac ggg ctg cgg aag ctg gaa gct ttt ttt gga ctc ctt ata acc     688
Asn Tyr Gly Leu Arg Lys Leu Glu Ala Phe Phe Gly Leu Leu Ile Thr
    190                 195                 200 att atg gcc ttg acc ttt ggc tat gag tat gtg gtg gcg cgt cct gag     736
Ile Met Ala Leu Thr Phe Gly Tyr Glu Tyr Val Val Ala Arg Pro Glu
205                 210                 215                 220 cag gga gcg ctt ctt cgg ggc ctg ttc ctg ccc tcg tgc ccg ggc tgc     784
Gln Gly Ala Leu Leu Arg Gly Leu Phe Leu Pro Ser Cys Pro Gly Cys
                225                 230                 235 ggc cac ccc gag ctg ctg cag gcg gtg ggc att gtt ggc gcc atc atc     832
Gly His Pro Glu Leu Leu Gln Ala Val Gly Ile Val Gly Ala Ile Ile
            240                 245                 250 atg ccc cac aac atc tac ctg cac tcg gcc ctg gtc aag tct cga gag     880
Met Pro His Asn Ile Tyr Leu His Ser Ala Leu Val Lys Ser Arg Glu
        255                 260                 265 ata gac cgg gcc cgc cga gcg gac atc aga gaa gcc aac atg tac ttc     928
Ile Asp Arg Ala Arg Arg Ala Asp Ile Arg Glu Ala Asn Met Tyr Phe
    270                 275                 280 ctg att gag gcc acc atc gcc ctg tcc gtc tcc ttt atc atc aac ctc     976
```

```
Leu Ile Glu Ala Thr Ile Ala Leu Ser Val Ser Phe Ile Ile Asn Leu
285                 290                 295                 300 ttt gtc atg gct gtc ttt ggg cag gcc ttc tac cag aaa acc aac cag      1024
Phe Val Met Ala Val Phe Gly Gln Ala Phe Tyr Gln Lys Thr Asn Gln
                    305                 310                 315 gct gcg ttc aac atc tgt gcc aac agc agc ctc cac gac tac gcc aag      1072
Ala Ala Phe Asn Ile Cys Ala Asn Ser Ser Leu His Asp Tyr Ala Lys
                320                 325                 330 atc ttc ccc atg aac aac gcc acc gtg gcc gtg gac att tac cag ggg      1120
Ile Phe Pro Met Asn Asn Ala Thr Val Ala Val Asp Ile Tyr Gln Gly
            335                 340                 345 ggc gtg atc ctg ggc tgc ctg ttc ggc ccc gcg gcc ctc tac atc tgg      1168
Gly Val Ile Leu Gly Cys Leu Phe Gly Pro Ala Ala Leu Tyr Ile Trp
350                 355                 360 gcc ata ggt ctc ctg gcg gct ggg cag agc tcc acc atg acg ggc acc      1216
Ala Ile Gly Leu Leu Ala Ala Gly Gln Ser Ser Thr Met Thr Gly Thr
365                 370                 375                 380 tac gcg gga cag ttc gtg atg gag ggc ttc ctg agg ctg cgg tgg tca      1264
Tyr Ala Gly Gln Phe Val Met Glu Gly Phe Leu Arg Leu Arg Trp Ser
                385                 390                 395 cgc ttc gcc cgt gtc ctc ctc acc cgc tcc tgc gcc atc ctg ccc acc      1312
Arg Phe Ala Arg Val Leu Leu Thr Arg Ser Cys Ala Ile Leu Pro Thr
                400                 405                 410 gtg ctc gtg gct gtc ttc cgg gac ctg agg gac ttg tcg ggc ctc aat      1360
Val Leu Val Ala Val Phe Arg Asp Leu Arg Asp Leu Ser Gly Leu Asn
            415                 420                 425 gat ctg ctc aac gtg ctg cag agc ctg ctc ccg ttc gcc gtg ctg           1408
Asp Leu Leu Asn Val Leu Gln Ser Leu Leu Leu Pro Phe Ala Val Leu
430                 435                 440 ccc atc ctc acg ttc acc agc atg ccc acc ctc atg cag gag ttt gcc      1456
Pro Ile Leu Thr Phe Thr Ser Met Pro Thr Leu Met Gln Glu Phe Ala
445                 450                 455                 460 aat ggc ctg ctg aac aag gtc gtc acc tct tcc atc atg gtg cta gtc      1504
Asn Gly Leu Leu Asn Lys Val Val Thr Ser Ser Ile Met Val Leu Val
                465                 470                 475 tgc gcc atc aac ctc tac ttc gtg gtc agc tat ctg ccc agc ctg ccc      1552
Cys Ala Ile Asn Leu Tyr Phe Val Val Ser Tyr Leu Pro Ser Leu Pro
                480                 485                 490 cac cct gcc tac ttc ggc ctt gca gcc ttg ctg gcc gca gcc tac ctg      1600
His Pro Ala Tyr Phe Gly Leu Ala Ala Leu Leu Ala Ala Ala Tyr Leu
            495                 500                 505 ggc ctc agc acc tac ctg gtc tgg acc tgt tgc ctt gcc cac gga gcc      1648
Gly Leu Ser Thr Tyr Leu Val Trp Thr Cys Cys Leu Ala His Gly Ala
510                 515                 520 acc ttt ctg gcc cac agc tcc cac cac cac ttc ctg tat ggg ctc ctt      1696
Thr Phe Leu Ala His Ser Ser His His His Phe Leu Tyr Gly Leu Leu
525                 530                 535                 540 gaa gag gac cag aaa ggg gag acc tct ggc tag gcccacacca gggcctggct    1749
Glu Glu Asp Gln Lys Gly Glu Thr Ser Gly
                545                 550 gggagtggca tgtatgacgt gactggcctg ctggatgtgg aggggcgcg tgcaggcagc     1809 aggatagagt gggacagttc ctgagaccag ccaacctggg ggctttaggg acctgctgtt    1869
tcctagcgca gccatgtgat taccctctgg gtctcagtgt cctcatctgt aaaatggaga    1929
caccaccacc cttgccatgg aggttaagca ctttaacaca gtgtctggca cttgggacaa    1989
aaacaaacaa acgaaaaa                                                  2007

<210> SEQ ID NO 30
```

```
<211> LENGTH: 550
<212> TYPE: PRT
<213> ORGANISM: Homo sapiens

<400> SEQUENCE: 30

Met Thr Gly Asp Lys Gly Pro Gln Arg Leu Ser Gly Ser Ser Tyr Gly
 1               5                  10                  15

Ser Ile Ser Ser Pro Thr Ser Pro Thr Ser Pro Gly Pro Gln Gln Ala
            20                  25                  30

Pro Pro Arg Glu Thr Tyr Leu Ser Glu Lys Ile Pro Ile Pro Asp Thr
        35                  40                  45

Lys Pro Gly Thr Phe Ser Leu Arg Lys Leu Trp Ala Phe Thr Gly Pro
    50                  55                  60

Gly Phe Leu Met Ser Ile Ala Phe Leu Asp Pro Gly Asn Ile Glu Ser
65                  70                  75                  80

Asp Leu Gln Ala Gly Ala Val Ala Gly Phe Lys Leu Leu Trp Val Leu
                85                  90                  95

Leu Trp Ala Thr Val Leu Gly Leu Leu Cys Gln Arg Leu Ala Ala Arg
            100                 105                 110

Leu Gly Val Val Thr Gly Lys Asp Leu Gly Glu Val Cys His Leu Tyr
        115                 120                 125

Tyr Pro Lys Val Pro Arg Thr Val Leu Trp Leu Thr Ile Glu Leu Ala
    130                 135                 140

Ile Val Gly Ser Asp Met Gln Glu Val Ile Gly Thr Ala Ile Ala Phe
145                 150                 155                 160

Asn Leu Leu Ser Ala Gly Arg Ile Pro Leu Trp Gly Gly Val Leu Ile
                165                 170                 175

Thr Ile Val Asp Thr Phe Phe Phe Leu Phe Asp Asn Tyr Gly Leu
            180                 185                 190

Arg Lys Leu Glu Ala Phe Phe Gly Leu Leu Ile Thr Ile Met Ala Leu
    195                 200                 205

Thr Phe Gly Tyr Glu Tyr Val Val Ala Arg Pro Glu Gln Gly Ala Leu
    210                 215                 220

Leu Arg Gly Leu Phe Leu Pro Ser Cys Pro Gly Cys Gly His Pro Glu
225                 230                 235                 240

Leu Leu Gln Ala Val Gly Ile Val Gly Ala Ile Ile Met Pro His Asn
                245                 250                 255

Ile Tyr Leu His Ser Ala Leu Val Lys Ser Arg Glu Ile Asp Arg Ala
                260                 265                 270

Arg Arg Ala Asp Ile Arg Glu Ala Asn Met Tyr Phe Leu Ile Glu Ala
        275                 280                 285

Thr Ile Ala Leu Ser Val Ser Phe Ile Ile Asn Leu Phe Val Met Ala
    290                 295                 300

Val Phe Gly Gln Ala Phe Tyr Gln Lys Thr Asn Gln Ala Ala Phe Asn
305                 310                 315                 320

Ile Cys Ala Asn Ser Ser Leu His Asp Tyr Ala Lys Ile Phe Pro Met
                325                 330                 335

Asn Asn Ala Thr Val Ala Val Asp Ile Tyr Gln Gly Gly Val Ile Leu
            340                 345                 350

Gly Cys Leu Phe Gly Pro Ala Ala Leu Tyr Ile Trp Ala Ile Gly Leu
        355                 360                 365

Leu Ala Ala Gly Gln Ser Ser Thr Met Thr Gly Thr Tyr Ala Gly Gln
    370                 375                 380

Phe Val Met Glu Gly Phe Leu Arg Leu Arg Trp Ser Arg Phe Ala Arg
```

```
385                390                395                400
Val Leu Leu Thr Arg Ser Cys Ala Ile Leu Pro Thr Val Leu Val Ala
                405                410                415

Val Phe Arg Asp Leu Arg Asp Leu Ser Gly Leu Asn Asp Leu Leu Asn
            420                425                430

Val Leu Gln Ser Leu Leu Leu Pro Phe Ala Val Leu Pro Ile Leu Thr
        435                440                445

Phe Thr Ser Met Pro Thr Leu Met Gln Glu Phe Ala Asn Gly Leu Leu
    450                455                460

Asn Lys Val Val Thr Ser Ile Met Val Leu Val Cys Ala Ile Asn
465                470                475                480

Leu Tyr Phe Val Val Ser Tyr Leu Pro Ser Leu Pro His Pro Ala Tyr
                485                490                495

Phe Gly Leu Ala Ala Leu Leu Ala Ala Ala Tyr Leu Gly Leu Ser Thr
            500                505                510

Tyr Leu Val Trp Thr Cys Cys Leu Ala His Gly Ala Thr Phe Leu Ala
        515                520                525

His Ser Ser His His His Phe Leu Tyr Gly Leu Leu Glu Glu Asp Gln
    530                535                540

Lys Gly Glu Thr Ser Gly
545                550

<210> SEQ ID NO 31
<211> LENGTH: 1866
<212> TYPE: DNA
<213> ORGANISM: Homo sapiens
<220> FEATURE:
<221> NAME/KEY: CDS
<222> LOCATION: (68)..(1516)
<223> OTHER INFORMATION: Clone: HNramp-2
<220> FEATURE:
<221> NAME/KEY: CDS
<222> LOCATION: (2)..(1516)
<223> OTHER INFORMATION: Clone: HNramp-2

<400> SEQUENCE: 31 a gga atg gag gag tac tct tgt ttt agc ttt cgt aaa ctc tgg gct ttc      49
  Gly Met Glu Glu Tyr Ser Cys Phe Ser Phe Arg Lys Leu Trp Ala Phe
  1               5                  10                  15 acc gga cca ggt ttt ctt atg agc att gcc tac ctg gat cca gga aat      97
Thr Gly Pro Gly Phe Leu Met Ser Ile Ala Tyr Leu Asp Pro Gly Asn
             20                  25                  30 att gaa tcc gat ttg cag tct gga gca gtg gct gga ttt aag ttg ctc     145
Ile Glu Ser Asp Leu Gln Ser Gly Ala Val Ala Gly Phe Lys Leu Leu
         35                  40                  45 tgg atc ctt ctg ttg gcc acc ctt gtg ggg ctg ctc cag cgg ctt         193
Trp Ile Leu Leu Leu Ala Thr Leu Val Gly Leu Leu Gln Arg Leu
     50                  55                  60 gca gct aga ctg gga gtg gtt act ggg ctg cat ctt gct gaa gta tgt     241
Ala Ala Arg Leu Gly Val Val Thr Gly Leu His Leu Ala Glu Val Cys
 65                  70                  75                  80 cac cgt cag tat ccc aag gtc cca cga gtc atc ctg tgg ctg atg gtg     289
His Arg Gln Tyr Pro Lys Val Pro Arg Val Ile Leu Trp Leu Met Val
                 85                  90                  95 gag ttg gct atc atc ggc tca gac atg caa gaa gtc att ggc tca gcc     337
Glu Leu Ala Ile Ile Gly Ser Asp Met Gln Glu Val Ile Gly Ser Ala
            100                 105                 110 att gct atc aat ctt ctg tct gta gga aga att cct ctg tgg ggt ggc     385
Ile Ala Ile Asn Leu Leu Ser Val Gly Arg Ile Pro Leu Trp Gly Gly
        115                 120                 125
```

-continued

```
gtt ctc atc acc att gca gat act ttt gta ttt ctc ttc ttg gac aaa    433
Val Leu Ile Thr Ile Ala Asp Thr Phe Val Phe Leu Phe Leu Asp Lys
        130                 135                 140 tat ggc ttg cgg aag cta gaa gca ttt ttt ggc ttt ctc atc act att    481
Tyr Gly Leu Arg Lys Leu Glu Ala Phe Phe Gly Phe Leu Ile Thr Ile
145                 150                 155                 160 atg gcc ctc aca ttt gga tat gag tat gtt aca gtg aaa ccc agc cag   529
Met Ala Leu Thr Phe Gly Tyr Glu Tyr Val Thr Val Lys Pro Ser Gln
                165                 170                 175 agc cag gta ctc aag ggc atg ttc gta cca tcc tgt tca ggc tgt cgc   577
Ser Gln Val Leu Lys Gly Met Phe Val Pro Ser Cys Ser Gly Cys Arg
        180                 185                 190 act cca cag att gaa cag gct gtg ggc atc gtg gga gct gtc atc atg   625
Thr Pro Gln Ile Glu Gln Ala Val Gly Ile Val Gly Ala Val Ile Met
        195                 200                 205 cca cac aac atg tac ctg cat tct gcc tta gtc aag tct aga cag gta   673
Pro His Asn Met Tyr Leu His Ser Ala Leu Val Lys Ser Arg Gln Val
        210                 215                 220 aac cgg aac aat aag cag gaa gtt cga gaa gcc aat aag tac ttt ttc   721
Asn Arg Asn Asn Lys Gln Glu Val Arg Glu Ala Asn Lys Tyr Phe Phe
225                 230                 235                 240 att gaa tcc tgc att gca ctc ttt gtt tcc ttc atc atc aat gtc ttt   769
Ile Glu Ser Cys Ile Ala Leu Phe Val Ser Phe Ile Ile Asn Val Phe
                245                 250                 255 gtc gtc tca gtc ttt gct gaa gca ttt ttt ggg aaa acc aac gag cag   817
Val Val Ser Val Phe Ala Glu Ala Phe Phe Gly Lys Thr Asn Glu Gln
                260                 265                 270 gtg gtt gaa gtc tgt aca aat acc agc agt cct cat gct ggc ctc ttt   865
Val Val Glu Val Cys Thr Asn Thr Ser Ser Pro His Ala Gly Leu Phe
        275                 280                 285 cct aaa gat aac tcg aca ctg gct gtg gac atc tac aaa ggg ggt gtt   913
Pro Lys Asp Asn Ser Thr Leu Ala Val Asp Ile Tyr Lys Gly Gly Val
        290                 295                 300 gtg ctg gga tgt tac ttt ggg cct gct gca ctc tac att tgg gca gtg   961
Val Leu Gly Cys Tyr Phe Gly Pro Ala Ala Leu Tyr Ile Trp Ala Val
305                 310                 315                 320 ggg atc ctg gct gca gga cag agc tcc acc atg aca gga acc tat tct  1009
Gly Ile Leu Ala Ala Gly Gln Ser Ser Thr Met Thr Gly Thr Tyr Ser
                325                 330                 335 ggc cag ttt gtc atg gag gga ttc ctg aac cta aag tgg tca cgc ttt  1057
Gly Gln Phe Val Met Glu Gly Phe Leu Asn Leu Lys Trp Ser Arg Phe
                340                 345                 350 gcc cga gtg gtt ctg act cgc tct atc gcc atc atc ccc act ctg ctt  1105
Ala Arg Val Val Leu Thr Arg Ser Ile Ala Ile Ile Pro Thr Leu Leu
        355                 360                 365 gtt gct gtc ttc caa gat gta gag cat cta aca ggg atg aat gac ttt  1153
Val Ala Val Phe Gln Asp Val Glu His Leu Thr Gly Met Asn Asp Phe
370                 375                 380 ctg aat gtt cta cag agc tta cag ctt ccc ttt gct ctc ata ccc atc  1201
Leu Asn Val Leu Gln Ser Leu Gln Leu Pro Phe Ala Leu Ile Pro Ile
385                 390                 395                 400 ctc aca ttt acg tac gtg cgg cca gta atg agt gac ttt gcc aat gga  1249
Leu Thr Phe Thr Tyr Val Arg Pro Val Met Ser Asp Phe Ala Asn Gly
                405                 410                 415 cta ggc tgg cgg att gca gga gga atc ttg gtc ctt atc atc tgt tcc  1297
Leu Gly Trp Arg Ile Ala Gly Gly Ile Leu Val Leu Ile Ile Cys Ser
        420                 425                 430 atc aat atg tac ttt gta gtg gtt tat gtc cgg gac cta ggg cat gtg  1345
Ile Asn Met Tyr Phe Val Val Val Tyr Val Arg Asp Leu Gly His Val
```

-continued

```
                435                 440                 445
gca tta tat gtg gtg gct gct gtg gtc agc gtg gct tat ctg ggc ttt    1393
Ala Leu Tyr Val Val Ala Ala Val Val Ser Val Ala Tyr Leu Gly Phe
        450                 455                 460 gtg ttc tac ttg ggt tgg caa tgt ttg att gca ctg ggc atg tcc ttc    1441
Val Phe Tyr Leu Gly Trp Gln Cys Leu Ile Ala Leu Gly Met Ser Phe
465                 470                 475                 480 ctg gac tgt ggg cat acg gta agc atc tct aaa ggc ctg ctg aca gaa    1489
Leu Asp Cys Gly His Thr Val Ser Ile Ser Lys Gly Leu Leu Thr Glu
                485                 490                 495 gaa gcc acc cgt ggc tac gtt aaa taa   cactggatta gtctgtcttc        1536
Glu Ala Thr Arg Gly Tyr Val Lys
                500                 505 tgcaggtagc catcagagcc agtgtgtttc tatggtttac tgtgtgaaca tagccaaaag  1596
tatgtgccgt tgcacagact gtgtttatga ctcaaccgtt ggttggaaaa gactttgttt  1656
catgtgtatt tgaaagatgg aattattttt tccttcctga cctaaccttt gaactggatt  1716
agggtgggat ctttgaaaag ctgacatttg ctgctatcat ccaacacta aattcttaag   1776 tagttgccca agggccagct cagtttatcc ttcggagaga caaggatatg catgattctt  1836
aaccaggcta tatgttaaaa aaaaaaaaaa                                   1866
```

<210> SEQ ID NO 32
<211> LENGTH: 504
<212> TYPE: PRT
<213> ORGANISM: Homo sapiens

<400> SEQUENCE: 32

```
Gly Met Glu Glu Tyr Ser Cys Phe Ser Phe Arg Lys Leu Trp Ala Phe
 1               5                  10                  15

Thr Gly Pro Gly Phe Leu Met Ser Ile Ala Tyr Leu Asp Pro Gly Asn
                20                  25                  30

Ile Glu Ser Asp Leu Gln Ser Gly Ala Val Ala Gly Phe Lys Leu Leu
            35                  40                  45

Trp Ile Leu Leu Leu Ala Thr Leu Val Gly Leu Leu Gln Arg Leu
    50                  55                  60

Ala Ala Arg Leu Gly Val Val Thr Gly Leu His Leu Ala Glu Val Cys
65                  70                  75                  80

His Arg Gln Tyr Pro Lys Val Pro Arg Val Ile Leu Trp Leu Met Val
                85                  90                  95

Glu Leu Ala Ile Ile Gly Ser Asp Met Gln Glu Val Ile Gly Ser Ala
            100                 105                 110

Ile Ala Ile Asn Leu Leu Ser Val Gly Arg Ile Pro Leu Trp Gly Gly
        115                 120                 125

Val Leu Ile Thr Ile Ala Asp Thr Phe Val Phe Leu Phe Leu Asp Lys
    130                 135                 140

Tyr Gly Leu Arg Lys Leu Glu Ala Phe Phe Gly Phe Leu Ile Thr Ile
145                 150                 155                 160

Met Ala Leu Thr Phe Gly Tyr Glu Tyr Val Thr Val Lys Pro Ser Gln
                165                 170                 175

Ser Gln Val Leu Lys Gly Met Phe Val Pro Ser Cys Ser Gly Cys Arg
            180                 185                 190

Thr Pro Gln Ile Glu Gln Ala Val Gly Ile Val Gly Ala Val Ile Met
        195                 200                 205

Pro His Asn Met Tyr Leu His Ser Ala Leu Val Lys Ser Arg Gln Val
    210                 215                 220
```

Asn Arg Asn Asn Lys Gln Glu Val Arg Glu Ala Asn Lys Tyr Phe Phe
225                 230                 235                 240

Ile Glu Ser Cys Ile Ala Leu Phe Val Ser Phe Ile Ile Asn Val Phe
            245                 250                 255

Val Val Ser Val Phe Ala Glu Ala Phe Phe Gly Lys Thr Asn Glu Gln
        260                 265                 270

Val Val Glu Val Cys Thr Asn Thr Ser Ser Pro His Ala Gly Leu Phe
    275                 280                 285

Pro Lys Asp Asn Ser Thr Leu Ala Val Asp Ile Tyr Lys Gly Gly Val
290                 295                 300

Val Leu Gly Cys Tyr Phe Gly Pro Ala Ala Leu Tyr Ile Trp Ala Val
305                 310                 315                 320

Gly Ile Leu Ala Ala Gly Gln Ser Ser Thr Met Thr Gly Thr Tyr Ser
            325                 330                 335

Gly Gln Phe Val Met Glu Gly Phe Leu Asn Leu Lys Trp Ser Arg Phe
        340                 345                 350

Ala Arg Val Val Leu Thr Arg Ser Ile Ala Ile Ile Pro Thr Leu Leu
    355                 360                 365

Val Ala Val Phe Gln Asp Val Glu His Leu Thr Gly Met Asn Asp Phe
370                 375                 380

Leu Asn Val Leu Gln Ser Leu Gln Leu Pro Phe Ala Leu Ile Pro Ile
385                 390                 395                 400

Leu Thr Phe Thr Tyr Val Arg Pro Val Met Ser Asp Phe Ala Asn Gly
            405                 410                 415

Leu Gly Trp Arg Ile Ala Gly Gly Ile Leu Val Leu Ile Ile Cys Ser
        420                 425                 430

Ile Asn Met Tyr Phe Val Val Tyr Val Arg Asp Leu Gly His Val
    435                 440                 445

Ala Leu Tyr Val Val Ala Val Val Ser Val Ala Tyr Leu Gly Phe
    450                 455                 460

Val Phe Tyr Leu Gly Trp Gln Cys Leu Ile Ala Leu Gly Met Ser Phe
465                 470                 475                 480

Leu Asp Cys Gly His Thr Val Ser Ile Ser Lys Gly Leu Leu Thr Glu
            485                 490                 495

Glu Ala Thr Arg Gly Tyr Val Lys
            500

<210> SEQ ID NO 33
<211> LENGTH: 482
<212> TYPE: PRT
<213> ORGANISM: Homo sapiens

<400> SEQUENCE: 33

Met Ser Ile Ala Tyr Leu Asp Pro Gly Asn Ile Glu Ser Asp Leu Gln
1               5                   10                  15

Ser Gly Ala Val Ala Gly Phe Lys Leu Leu Trp Ile Leu Leu Leu Ala
            20                  25                  30

Thr Leu Val Gly Leu Leu Leu Gln Arg Leu Ala Ala Arg Leu Gly Val
        35                  40                  45

Val Thr Gly Leu His Leu Ala Glu Val Cys His Arg Gln Tyr Pro Lys
    50                  55                  60

Val Pro Arg Val Ile Leu Trp Leu Met Val Glu Leu Ala Ile Ile Gly
65                  70                  75                  80

Ser Asp Met Gln Glu Val Ile Gly Ser Ala Ile Ala Ile Asn Leu Leu

-continued

```
                85                  90                  95
Ser Val Gly Arg Ile Pro Leu Trp Gly Gly Val Leu Ile Thr Ile Ala
                    100                 105                 110
Asp Thr Phe Val Phe Leu Phe Leu Asp Lys Tyr Gly Leu Arg Lys Leu
            115                 120                 125
Glu Ala Phe Phe Gly Phe Leu Ile Thr Ile Met Ala Leu Thr Phe Gly
        130                 135                 140
Tyr Glu Tyr Val Thr Val Lys Pro Ser Gln Ser Gln Val Leu Lys Gly
145                 150                 155                 160
Met Phe Val Pro Ser Cys Ser Cys Arg Thr Pro Gln Ile Glu Gln
                165                 170                 175
Ala Val Gly Ile Val Gly Ala Val Ile Met Pro His Asn Met Tyr Leu
            180                 185                 190
His Ser Ala Leu Val Lys Ser Arg Gln Val Asn Arg Asn Asn Lys Gln
        195                 200                 205
Glu Val Arg Glu Ala Asn Lys Tyr Phe Phe Ile Glu Ser Cys Ile Ala
    210                 215                 220
Leu Phe Val Ser Phe Ile Ile Asn Val Phe Val Ser Val Phe Ala
225                 230                 235                 240
Glu Ala Phe Phe Gly Lys Thr Asn Glu Gln Val Val Glu Val Cys Thr
                245                 250                 255
Asn Thr Ser Ser Pro His Ala Gly Leu Phe Pro Lys Asp Asn Ser Thr
            260                 265                 270
Leu Ala Val Asp Ile Tyr Lys Gly Gly Val Val Leu Gly Cys Tyr Phe
        275                 280                 285
Gly Pro Ala Ala Leu Tyr Ile Trp Ala Val Gly Ile Leu Ala Ala Gly
    290                 295                 300
Gln Ser Ser Thr Met Thr Gly Thr Tyr Ser Gly Gln Phe Val Met Glu
305                 310                 315                 320
Gly Phe Leu Asn Leu Lys Trp Ser Arg Phe Ala Arg Val Val Leu Thr
                325                 330                 335
Arg Ser Ile Ala Ile Ile Pro Thr Leu Leu Val Ala Val Phe Gln Asp
            340                 345                 350
Val Glu His Leu Thr Gly Met Asn Asp Phe Leu Asn Val Leu Gln Ser
        355                 360                 365
Leu Gln Leu Pro Phe Ala Leu Ile Pro Ile Leu Thr Phe Thr Tyr Val
    370                 375                 380
Arg Pro Val Met Ser Asp Phe Ala Asn Gly Leu Gly Trp Arg Ile Ala
385                 390                 395                 400
Gly Gly Ile Leu Val Leu Ile Ile Cys Ser Ile Asn Met Tyr Phe Val
                405                 410                 415
Val Val Tyr Val Arg Asp Leu Gly His Val Ala Leu Tyr Val Val Ala
            420                 425                 430
Ala Val Val Ser Val Ala Tyr Leu Gly Phe Val Phe Tyr Leu Gly Trp
        435                 440                 445
Gln Cys Leu Ile Ala Leu Gly Met Ser Phe Leu Asp Cys Gly His Thr
    450                 455                 460
Val Ser Ile Ser Lys Gly Leu Leu Thr Glu Glu Ala Thr Arg Gly Tyr
465                 470                 475                 480
Val Lys
```